(12) United States Patent
Uthgenannt et al.

(10) Patent No.: US 10,159,498 B2
(45) Date of Patent: *Dec. 25, 2018

(54) METHOD AND APPARATUS FOR MANUFACTURING AN IMPLANT

(71) Applicant: Biomet Manufacturing, LLC, Warsaw, IN (US)

(72) Inventors: Brian A. Uthgenannt, Cricklade (GB); Robert Metzger, Wakarusa, IN (US); Nathan E. Belcher, Ferguson, MO (US); Joshua B. Catanzarite, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 603 days.

This patent is subject to a terminal disclaimer.

(21) Appl. No.: 14/739,160

(22) Filed: Jun. 15, 2015

(65) Prior Publication Data

US 2015/0351778 A1    Dec. 10, 2015

Related U.S. Application Data

(60) Continuation of application No. 13/766,419, filed on Feb. 13, 2013, now abandoned, which is a division of
(Continued)

(51) Int. Cl.
*A61F 2/38* (2006.01)
*A61B 17/16* (2006.01)
(Continued)

(52) U.S. Cl.
CPC ...... *A61B 17/1675* (2013.01); *A61B 17/1764* (2013.01); *A61B 90/96* (2016.02);
(Continued)

(58) Field of Classification Search
CPC . A61B 17/1675; A61B 17/1617; A61B 90/96; A61F 2/38
(Continued)

(56) References Cited

U.S. PATENT DOCUMENTS 1,480,285 A   1/1924   Moore
1,763,730 A   6/1930   Lackum
(Continued)

FOREIGN PATENT DOCUMENTS

CA   2447694 A1   12/2002
CA   2501041 A1   4/2004
(Continued)

OTHER PUBLICATIONS

"U.S. Appl. No. 12/255,945, Appeal Decision mailed Feb. 27, 2017", 12 pgs.
(Continued)

*Primary Examiner* — Hiep V Nguyen
(74) *Attorney, Agent, or Firm* — Schwegman Lundberg & Woessner, P.A.

(57) ABSTRACT

An orthopedic device includes a femoral implant having a non-custom internal bone engagement surface. The femoral implant includes at least nine parameters adjusted preoperatively to correspond to a specific patient. The parameters can include patient-specific lengths, such as, for example, medial and lateral condyle widths and notch height, and patient-specific medial and lateral angles.

16 Claims, 17 Drawing Sheets

Related U.S. Application Data application No. 12/872,663, filed on Aug. 31, 2010, now Pat. No. 8,407,067.

(60) Provisional application No. 61/310,752, filed on Mar. 5, 2010.

(51) Int. Cl.

| | |
|---|---|
| *A61B 17/17* | (2006.01) |
| *B33Y 80/00* | (2015.01) |
| *B33Y 50/00* | (2015.01) |
| *A61F 2/30* | (2006.01) |
| *A61B 90/96* | (2016.01) |
| *A61B 90/98* | (2016.01) |
| *G16H 50/50* | (2018.01) |
| *G06F 19/00* | (2018.01) |
| *A61B 17/15* | (2006.01) |
| *A61B 17/00* | (2006.01) |
| *A61F 2/46* | (2006.01) |
| *A61B 34/10* | (2016.01) |

(52) U.S. Cl.
CPC .......... *A61B 90/98* (2016.02); *A61F 2/30942* (2013.01); *A61F 2/38* (2013.01); *A61F 2/3859* (2013.01); *B33Y 50/00* (2014.12); *B33Y 80/00* (2014.12); *G06F 19/00* (2013.01); *G16H 50/50* (2018.01); *A61B 17/155* (2013.01); *A61B 34/10* (2016.02); *A61B 2017/00526* (2013.01); *A61F 2002/3071* (2013.01); *A61F 2002/3096* (2013.01); *A61F 2002/30616* (2013.01); *A61F 2002/30617* (2013.01); *A61F 2002/30708* (2013.01); *A61F 2002/30884* (2013.01); *A61F 2002/30948* (2013.01); *A61F 2002/30952* (2013.01); *A61F 2002/30953* (2013.01); *A61F 2002/30962* (2013.01); *A61F 2002/3863* (2013.01); *A61F 2002/4633* (2013.01); *A61F 2250/0084* (2013.01); *A61F 2250/0085* (2013.01); *A61F 2250/0097* (2013.01); *Y10T 29/49* (2015.01)

(58) Field of Classification Search
USPC .......................................................... 705/2
See application file for complete search history.

(56) References Cited

U.S. PATENT DOCUMENTS

| | | |
|---|---|---|
| 1,959,615 A | 5/1934 | Derrah |
| 2,181,746 A | 11/1939 | Siebrandt |
| 2,407,845 A | 9/1946 | Nemeyer |
| 2,416,228 A | 2/1947 | Sheppard |
| 2,433,815 A | 12/1947 | Nicephore |
| 2,455,655 A | 12/1948 | Carroll |
| 2,618,913 A | 11/1952 | Plancon et al. |
| 2,702,550 A | 2/1955 | Rowe |
| 2,724,326 A | 11/1955 | Long |
| 2,910,978 A | 11/1959 | Urist |
| 2,955,530 A | 10/1960 | Nilo |
| 3,048,522 A | 8/1962 | Valley |
| 3,229,006 A | 1/1966 | Egon |
| 3,229,372 A | 1/1966 | Quashnock et al. |
| 3,330,611 A | 7/1967 | Heifetz |
| 3,514,791 A | 6/1970 | Sparks |
| 3,554,197 A | 1/1971 | Dobbie |
| 3,624,747 A | 11/1971 | McKnight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,840,904 A | 10/1974 | Tronzo |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon et al. |
| 3,975,858 A | 8/1976 | Much |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,246,895 A | 1/1981 | Rehder |
| 4,299,224 A | 11/1981 | Noiles |
| 4,304,178 A | 12/1981 | Haberle |
| 4,306,866 A | 12/1981 | Weissman |
| 4,311,145 A | 1/1982 | Esty et al. |
| 4,324,006 A | 4/1982 | Charnley |
| 4,344,193 A | 8/1982 | Kenny |
| 4,349,018 A | 9/1982 | Chamber |
| 4,373,709 A | 2/1983 | Whitt et al. |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| 4,421,112 A | 12/1983 | Mains et al. |
| 4,428,571 A | 1/1984 | Sugarman |
| 4,436,684 A | 3/1984 | White |
| D273,895 S | 5/1984 | Kenna et al. |
| D274,091 S | 5/1984 | Kenna |
| 4,453,421 A | 6/1984 | Umano |
| 4,457,306 A | 7/1984 | Borzone |
| 4,475,549 A | 10/1984 | Oh |
| 4,501,269 A | 2/1985 | Bagby |
| 4,506,393 A | 3/1985 | Murphy |
| 4,509,518 A | 4/1985 | Mcgarry et al. |
| 4,516,276 A | 5/1985 | Mittelmeier |
| 4,524,766 A | 6/1985 | Petersen |
| 4,528,980 A | 7/1985 | Kenna |
| 4,534,365 A | 8/1985 | Bonetta et al. |
| 4,535,773 A | 8/1985 | Yoon |
| 4,545,375 A | 10/1985 | Cline |
| 4,554,686 A | 11/1985 | Baker |
| 4,562,598 A | 1/1986 | Kranz |
| 4,565,191 A | 1/1986 | Slocum |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,619,658 A | 10/1986 | Pappas et al. |
| 4,621,630 A | 11/1986 | Kenna |
| 4,624,254 A | 11/1986 | Mcgarry et al. |
| 4,632,111 A | 12/1986 | Roche |
| 4,633,862 A | 1/1987 | Petersen |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,663,720 A | 5/1987 | Duret et al. |
| 4,678,470 A | 7/1987 | Nashef et al. |
| 4,682,598 A | 7/1987 | Beraha |
| 4,685,460 A | 8/1987 | Thornton |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,711,233 A | 12/1987 | Brown |

(56) References Cited

U.S. PATENT DOCUMENTS

| | | |
|---|---|---|
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,722,330 A | 2/1988 | Russell et al. |
| 4,739,751 A | 4/1988 | Sapega et al. |
| 4,759,350 A | 7/1988 | Dunn et al. |
| 4,778,474 A | 10/1988 | Homsy |
| 4,794,854 A | 1/1989 | Swaim |
| 4,800,874 A | 1/1989 | David et al. |
| 4,817,602 A | 4/1989 | Beraha |
| 4,821,213 A | 4/1989 | Cline et al. |
| 4,822,365 A | 4/1989 | Walker et al. |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,863,472 A | 9/1989 | Tormala et al. |
| 4,871,975 A | 10/1989 | Nawata et al. |
| 4,888,022 A | 12/1989 | Huebsch |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,911,721 A | 3/1990 | Andergaten |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,950,296 A | 8/1990 | McIntyre |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | hodorek |
| 4,985,037 A | 1/1991 | Petersen |
| 4,985,038 A | 1/1991 | Lyell |
| 4,994,064 A | 2/1991 | Aboczky |
| 5,002,579 A | 3/1991 | Copf et al. |
| 5,006,121 A | 4/1991 | Hafeli |
| 5,007,912 A | 4/1991 | Albrektsson et al. |
| 5,007,936 A | 4/1991 | Woolson |
| 5,015,247 A | 5/1991 | Michelson |
| 5,019,105 A | 5/1991 | Wiley |
| 5,030,219 A | 7/1991 | Matsen, III et al. |
| 5,030,221 A | 7/1991 | Buechel et al. |
| 5,032,132 A | 7/1991 | Matsen, III et al. |
| 5,035,700 A | 7/1991 | Kenna |
| 5,037,424 A | 8/1991 | Aboczsky |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,060,678 A | 10/1991 | Bauman et al. |
| 5,061,270 A | 10/1991 | Aboczky |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,425 A | 4/1992 | Hwang |
| 5,108,441 A | 4/1992 | Mcdowell |
| 5,111,987 A | 5/1992 | Moeinzadeh et al. |
| 5,122,144 A | 6/1992 | Bert et al. |
| 5,123,906 A | 6/1992 | Kelman |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,141,512 A | 8/1992 | Farmer et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,176,711 A | 1/1993 | Grimes |
| 5,178,622 A | 1/1993 | Lehner, II |
| 5,183,053 A | 2/1993 | Yeh |
| 5,183,464 A | 2/1993 | Dubrul et al. |
| 5,186,178 A | 2/1993 | Yeh |
| 5,192,327 A | 3/1993 | Brantigan |
| 5,194,066 A | 3/1993 | Van Zile |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,222,984 A | 6/1993 | Forte |
| 5,228,459 A | 7/1993 | Caspari et al. |
| 5,234,433 A | 8/1993 | Bert et al. |
| 5,242,448 A | 9/1993 | Pettine et al. |
| 5,246,444 A | 9/1993 | Schreiber |
| 5,253,506 A | 10/1993 | Davis et al. |
| 5,258,004 A | 11/1993 | Bales et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| D343,247 S | 1/1994 | Walen |
| 5,275,166 A | 1/1994 | Vaitekunas et al. |
| 5,275,603 A | 1/1994 | Ferrante et al. |
| 5,282,802 A | 2/1994 | Mahony, III |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,299,288 A | 3/1994 | Glassman et al. |
| 5,300,077 A | 4/1994 | Howell |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,323,697 A | 6/1994 | Schrock |
| 5,329,845 A | 7/1994 | Bichel |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Bonutti |
| 5,360,446 A | 11/1994 | Kennedy |
| 5,364,402 A | 11/1994 | Mumme et al. |
| 5,368,599 A | 11/1994 | Hirsch et al. |
| 5,368,858 A | 11/1994 | Hunziker |

(56) References Cited

U.S. PATENT DOCUMENTS

| | | |
|---|---|---|
| 5,370,692 A | 12/1994 | Fink et al. |
| 5,370,699 A | 12/1994 | Hood et al. |
| 5,379,133 A | 1/1995 | Kirk |
| 5,382,249 A | 1/1995 | Fletcher et al. |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |
| D358,647 S | 5/1995 | Cohen et al. |
| 5,411,521 A | 5/1995 | Putnam et al. |
| 5,415,662 A | 5/1995 | Ferrante et al. |
| 5,417,694 A | 5/1995 | Marik et al. |
| 5,423,827 A | 6/1995 | Mumme et al. |
| 5,425,355 A | 6/1995 | Kulick |
| 5,425,745 A | 6/1995 | Green et al. |
| 5,438,263 A | 8/1995 | Dworkin et al. |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,449,360 A | 9/1995 | Schreiber |
| 5,452,407 A | 9/1995 | Crook |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,462,550 A | 10/1995 | Dietz et al. |
| 5,472,415 A | 12/1995 | King et al. |
| 5,474,559 A | 12/1995 | Bertin et al. |
| 5,484,095 A | 1/1996 | Green et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | Defonzo et al. |
| 5,507,763 A | 4/1996 | Petersen et al. |
| 5,507,833 A | 4/1996 | Bohn |
| 5,514,139 A | 5/1996 | Goldstein et al. |
| 5,514,143 A | 5/1996 | Bonutti et al. |
| 5,514,519 A | 5/1996 | Neckers |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,546,720 A | 8/1996 | Labruzza |
| 5,549,683 A | 8/1996 | Bonutti |
| 5,549,688 A * | 8/1996 | Ries ............... A61F 2/3859 623/20.35 |
| 5,554,169 A | 9/1996 | Green et al. |
| 5,554,190 A | 9/1996 | Draenert |
| 5,560,096 A | 10/1996 | Stephens |
| 5,560,728 A | 10/1996 | Mcfadden |
| 5,562,675 A | 10/1996 | Mcnulty et al. |
| 5,569,163 A | 10/1996 | Francis et al. |
| 5,569,261 A | 10/1996 | Marik et al. |
| 5,570,700 A | 11/1996 | Vogeler |
| 5,571,110 A | 11/1996 | Matsen, III et al. |
| 5,571,111 A | 11/1996 | Aboczky |
| 5,578,037 A | 11/1996 | Sanders et al. |
| 5,578,039 A | 11/1996 | Vendrely et al. |
| 5,586,558 A | 12/1996 | Riley |
| 5,593,411 A | 1/1997 | Stalcup et al. |
| 5,593,448 A | 1/1997 | Dong |
| 5,595,703 A | 1/1997 | Swaelens et al. |
| 5,597,379 A | 1/1997 | Haines et al. |
| 5,601,565 A | 2/1997 | Huebner |
| 5,607,431 A | 3/1997 | Dudasik et al. |
| 5,608,052 A | 3/1997 | Zmitek et al. |
| 5,609,603 A | 3/1997 | Linden |
| 5,611,802 A | 3/1997 | Samuelson et al. |
| 5,613,969 A | 3/1997 | Jenkins, Jr. |
| 5,616,147 A | 4/1997 | Gadelius |
| 5,620,448 A | 4/1997 | Puddu |
| 5,624,444 A | 4/1997 | Wixon et al. |
| 5,624,463 A | 4/1997 | Stone et al. |
| 5,632,745 A | 5/1997 | Schwartz |
| 5,634,927 A | 6/1997 | Houston et al. |
| 5,641,323 A | 6/1997 | Caldarise |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,658,294 A | 8/1997 | Sederholm |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| 5,671,018 A | 9/1997 | Ohara et al. |
| D385,163 S | 10/1997 | Hutchins et al. |
| 5,676,668 A | 10/1997 | McCue et al. |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,398 A | 11/1997 | Carls et al. |
| 5,683,469 A | 11/1997 | Johnson et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,694,693 A | 12/1997 | Hutchins et al. |
| 5,697,933 A | 12/1997 | Gundlapalli et al. |
| 5,702,447 A | 12/1997 | Walch et al. |
| 5,702,460 A | 12/1997 | Carls et al. |
| 5,702,464 A | 12/1997 | Lackey et al. |
| 5,702,475 A | 12/1997 | Zahedi |
| 5,704,941 A | 1/1998 | Jacober et al. |
| 5,707,350 A | 1/1998 | Krause et al. |
| 5,709,689 A | 1/1998 | Ferrante et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliott et al. |
| 5,722,978 A | 3/1998 | Jenkins, Jr. |
| 5,723,331 A | 3/1998 | Tubo et al. |
| 5,725,376 A | 3/1998 | Poirier |
| 5,725,593 A | 3/1998 | Caracciolo |
| 5,728,128 A | 3/1998 | Crickenberger et al. |
| 5,733,292 A | 3/1998 | Gustilo et al. |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,762,125 A | 6/1998 | Mastrorio |
| 5,766,251 A | 6/1998 | Koshino et al. |
| 5,768,134 A | 6/1998 | Swaelens et al. |
| 5,769,092 A | 6/1998 | Williamson, Jr. |
| 5,769,855 A | 6/1998 | Bertin et al. |
| 5,769,899 A | 6/1998 | Schwartz et al. |
| 5,772,594 A | 6/1998 | Barrick |
| 5,776,200 A | 7/1998 | Johnson |
| 5,786,217 A | 7/1998 | Tubo et al. |
| 5,788,700 A | 8/1998 | Morawa et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | Mcgarry et al. |
| 5,824,083 A | 10/1998 | Draenert |
| 5,835,619 A | 11/1998 | Morimoto et al. |
| 5,842,477 A | 12/1998 | Naughton et al. |

(56) References Cited

U.S. PATENT DOCUMENTS

| | | |
|---|---|---|
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,899,914 A | 5/1999 | Zirps et al. |
| 5,901,060 A | 5/1999 | Schall et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,921,988 A | 7/1999 | Legrand |
| 5,921,990 A | 7/1999 | Webb |
| 5,925,049 A | 7/1999 | Gustilo et al. |
| 5,925,077 A | 7/1999 | Williamson et al. |
| 5,942,370 A | 8/1999 | Neckers |
| 5,961,499 A | 10/1999 | Bonutti et al. |
| 5,967,777 A | 10/1999 | Klein et al. |
| 5,976,149 A | 11/1999 | Masini |
| 5,980,526 A | 11/1999 | Johnson et al. |
| 5,997,566 A | 12/1999 | Tobin |
| 6,007,537 A | 12/1999 | Burkinshaw et al. |
| 6,008,433 A | 12/1999 | Stone |
| 6,012,456 A | 1/2000 | Schuerch |
| 6,013,081 A | 1/2000 | Burkinshaw et al. |
| 6,015,419 A | 1/2000 | Strome et al. |
| 6,019,767 A | 2/2000 | Howell |
| 6,022,350 A | 2/2000 | Ganem |
| 6,024,746 A | 2/2000 | Katz |
| 6,033,415 A | 3/2000 | Mittelstadt et al. |
| 6,042,612 A | 3/2000 | Voydeville |
| 6,056,754 A | 5/2000 | Haines et al. |
| 6,056,756 A | 5/2000 | Eng et al. |
| 6,059,789 A | 5/2000 | Dinger et al. |
| 6,059,817 A | 5/2000 | Bonutti et al. |
| 6,059,831 A | 5/2000 | Braslow et al. |
| 6,059,833 A | 5/2000 | Doets |
| 6,063,095 A | 5/2000 | Wang et al. |
| 6,066,175 A | 5/2000 | Henderson et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,132,469 A | 10/2000 | Schroeder |
| 6,132,472 A | 10/2000 | Bonutti |
| 6,136,033 A | 10/2000 | Suemer |
| 6,156,069 A | 12/2000 | Amstutz |
| 6,156,070 A | 12/2000 | Incavo et al. |
| 6,159,217 A | 12/2000 | Robie et al. |
| 6,159,246 A | 12/2000 | Mendes et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,171,340 B1 | 1/2001 | Mcdowell et al. |
| 6,174,321 B1 | 1/2001 | Webb |
| 6,185,315 B1 | 2/2001 | Schmucker et al. |
| 6,187,010 B1 | 2/2001 | Masini |
| 6,187,023 B1 | 2/2001 | Bonutti |
| 6,195,158 B1 | 2/2001 | Cadell et al. |
| 6,195,615 B1 | 2/2001 | Lysen |
| 6,197,064 B1 | 3/2001 | Haines et al. |
| 6,198,794 B1 | 3/2001 | Peshkin et al. |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,211,976 B1 | 4/2001 | Popovich et al. |
| 6,214,051 B1 | 4/2001 | Badorf et al. |
| 6,228,121 B1 | 5/2001 | Khalili |
| 6,238,435 B1 | 5/2001 | Meulink et al. |
| 6,254,604 B1 | 7/2001 | Howell |
| 6,258,097 B1 | 7/2001 | Cook et al. |
| 6,258,127 B1 | 7/2001 | Schmotzer |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,277,136 B1 | 8/2001 | Bonutti et al. |
| 6,290,703 B1 | 9/2001 | Ganem |
| 6,290,704 B1 | 9/2001 | Burkinshaw et al. |
| 6,290,727 B1 | 9/2001 | Otto et al. |
| 6,293,971 B1 | 9/2001 | Nelson et al. |
| 6,301,495 B1 | 10/2001 | Gueziec et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,806 B1 | 12/2001 | Fox |
| 6,325,829 B1 | 12/2001 | Schmotzer |
| 6,327,491 B1 | 12/2001 | Franklin et al. |
| 6,328,572 B1 | 12/2001 | Higashida et al. |
| 6,338,737 B1 | 1/2002 | Toledano |
| 6,338,738 B1 | 1/2002 | Bellotti et al. |
| 6,343,987 B2 | 2/2002 | Hayama et al. |
| 6,354,011 B1 | 3/2002 | Albrecht |
| 6,358,266 B1 | 3/2002 | Bonutti |
| 6,361,506 B1 | 3/2002 | Saenger et al. |
| 6,361,563 B2 | 3/2002 | Terrill-Grisoni et al. |
| 6,361,565 B1 | 3/2002 | Bonutti |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,040 B1 | 5/2002 | Christoudias |
| 6,391,251 B1 | 5/2002 | Keicher et al. |
| 6,395,005 B1 | 5/2002 | Lovell |
| 6,406,495 B1 | 6/2002 | Schoch |
| 6,409,722 B1 | 6/2002 | Hoey et al. |
| 6,413,279 B1 | 7/2002 | Metzger et al. |
| 6,416,553 B1 | 7/2002 | White et al. |
| 6,423,063 B1 | 7/2002 | Bonutti |
| 6,423,068 B1 | 7/2002 | Reisberg et al. |
| 6,424,332 B1 | 7/2002 | Powell |
| 6,427,698 B1 | 8/2002 | Yoon |
| 6,428,541 B1 | 8/2002 | Boyd et al. |
| 6,431,743 B1 | 8/2002 | Mizutani et al. |
| D462,767 S | 9/2002 | Meyer et al. |
| 6,458,135 B1 | 10/2002 | Harwin et al. |
| 6,459,948 B1 | 10/2002 | Ateshian et al. |
| 6,463,351 B1 | 10/2002 | Clynch |
| 6,468,280 B1 | 10/2002 | Saenger et al. |
| 6,468,289 B1 | 10/2002 | Bonutti |
| 6,475,243 B1 | 11/2002 | Sheldon et al. |
| 6,478,799 B1 | 11/2002 | Williamson |
| 6,482,209 B1 | 11/2002 | Engh et al. |
| 6,482,236 B2 | 11/2002 | Habecker |
| 6,488,715 B1 | 12/2002 | Pope et al. |
| 6,500,181 B1 | 12/2002 | Portney |
| 6,503,255 B1 | 1/2003 | Albrektsson et al. |
| 6,503,267 B2 | 1/2003 | Bonutti et al. |

(56) References Cited

U.S. PATENT DOCUMENTS

| | | |
|---|---|---|
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,554,838 B2 | 4/2003 | McGovern et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,589,283 B1 | 7/2003 | Metzger et al. |
| 6,591,581 B2 | 7/2003 | Schmieding |
| 6,602,259 B1 | 8/2003 | Masini |
| 6,605,293 B1 | 8/2003 | Giordano et al. |
| 6,610,067 B2 | 8/2003 | Tallarida et al. |
| 6,620,181 B1 | 9/2003 | Bonutti |
| 6,622,567 B1 | 9/2003 | Hamel et al. |
| 6,629,999 B1 | 10/2003 | Serafin, Jr. |
| 6,632,225 B2 | 10/2003 | Sanford et al. |
| 6,635,073 B2 | 10/2003 | Bonutti |
| 6,641,617 B1 | 11/2003 | Merrill et al. |
| 6,673,077 B1 | 1/2004 | Katz |
| 6,676,662 B1 | 1/2004 | Bagga et al. |
| 6,676,892 B2 | 1/2004 | Das et al. |
| 6,682,566 B2 | 1/2004 | Draenert |
| 6,682,567 B1 | 1/2004 | Schroeder |
| 6,695,848 B2 | 2/2004 | Haines |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,743,235 B2 | 6/2004 | Subba Rao |
| 6,749,638 B1 | 6/2004 | Saladino |
| 6,750,653 B1 | 6/2004 | Zou et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,975,755 B1 | 12/2005 | Baumberg |
| 6,979,299 B2 | 12/2005 | Peabody et al. |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,022,141 B2 | 4/2006 | Dwyer et al. |
| 7,029,477 B2 | 4/2006 | Grimm |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,995 B2 | 9/2006 | Crofford |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,172,599 B2 | 2/2007 | Steffensmeier et al. |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,291,117 B2 | 11/2007 | Boecker et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,207 B1 | 2/2008 | Smith |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,419,492 B2 | 9/2008 | Yoon et al. |
| 7,427,200 B2 * | 9/2008 | Noble ............ G09B 23/28 345/581 |
| 7,427,272 B2 | 9/2008 | Richard et al. |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,324 B1 | 2/2009 | Metzger et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'Neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,674,100 B2 | 3/2010 | Hayes-Pankhurst et al. |
| 7,682,398 B2 | 3/2010 | Croxton et al. |

(56) References Cited

U.S. PATENT DOCUMENTS

| | | |
|---|---|---|
| 7,695,477 B2 | 4/2010 | Creger et al. |
| 7,695,521 B2 | 4/2010 | Ely et al. |
| 7,699,847 B2 | 4/2010 | Sheldon et al. |
| 7,702,380 B1 | 4/2010 | Dean |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kees et al. |
| 7,837,040 B2 | 11/2010 | Ward et al. |
| 7,837,690 B2 | 11/2010 | Metzger |
| 7,846,382 B2 | 12/2010 | Strand et al. |
| 7,850,698 B2 | 12/2010 | Straszheim-Morley et al. |
| 7,854,737 B2 | 12/2010 | Daniels et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Rossner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,823 B2 | 5/2012 | Nycz et al. |
| 8,167,951 B2 | 5/2012 | Ammann et al. |
| 8,170,641 B2 | 5/2012 | Belcher |
| 8,172,850 B2 | 5/2012 | Mcminn |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'Neill et al. |
| 8,268,100 B2 | 9/2012 | O'Neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,426 B2 | 12/2012 | Nycz |
| 8,337,501 B2 | 12/2012 | Fitz et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,529,578 B2 | 9/2013 | Daniels et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,551,099 B2 | 10/2013 | Lang et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,781,557 B2 | 7/2014 | Dean et al. |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite et al. |
| 8,979,936 B2 | 3/2015 | White et al. |
| 8,986,309 B1 | 3/2015 | Murphy |
| 9,005,297 B2 | 4/2015 | Katrana et al. |
| 9,060,788 B2 | 6/2015 | Bollinger |
| 9,066,734 B2 | 6/2015 | Schoenefeld et al. |
| 9,107,139 B2 | 8/2015 | Sirotkin et al. |
| 9,113,971 B2 | 8/2015 | Metzger et al. |
| 9,173,661 B2 | 11/2015 | Metzger et al. |
| 9,186,254 B2 | 11/2015 | Fitz et al. |
| 9,208,558 B2 | 12/2015 | Dean et al. |
| 9,241,745 B2 | 1/2016 | Smith et al. |
| 9,275,191 B2 | 3/2016 | Dean et al. |

(56) References Cited

U.S. PATENT DOCUMENTS

| | | |
|---|---|---|
| 9,289,253 B2 | 3/2016 | Vanasse et al. |
| 9,292,920 B2 | 3/2016 | Dean et al. |
| 9,330,206 B2 | 5/2016 | Dean et al. |
| 9,339,278 B2 | 5/2016 | Meridew et al. |
| 9,345,548 B2 | 5/2016 | Schoenefeld et al. |
| 9,445,907 B2 | 5/2016 | Meridew et al. |
| 9,480,490 B2 | 11/2016 | Metzger et al. |
| 9,480,580 B2 | 11/2016 | White et al. |
| 9,522,010 B2 | 12/2016 | Metzger et al. |
| 9,539,013 B2 | 1/2017 | Katrana et al. |
| 9,662,127 B2 | 5/2017 | Meridew et al. |
| 9,662,216 B2 | 5/2017 | Witt et al. |
| 9,700,329 B2 | 7/2017 | Metzger et al. |
| 9,730,616 B2 | 8/2017 | Hershberger |
| 9,743,935 B2 | 8/2017 | Smith et al. |
| 9,795,399 B2 | 10/2017 | Metzger et al. |
| 9,861,387 B2 | 1/2018 | Metzger et al. |
| 9,907,659 B2 | 3/2018 | Belcher et al. |
| 9,913,734 B2 | 3/2018 | White et al. |
| 9,918,740 B2 | 3/2018 | Uthgenannt et al. |
| 9,968,376 B2 | 5/2018 | Metzger et al. |
| 9,993,344 B2 | 6/2018 | White et al. |
| 2001/0005797 A1 | 6/2001 | Barlow et al. |
| 2001/0011190 A1 | 8/2001 | Park |
| 2001/0018589 A1 | 8/2001 | Muller |
| 2001/0021876 A1 | 9/2001 | Terrill-Grisoni et al. |
| 2001/0034554 A1 | 10/2001 | Pappas |
| 2001/0037155 A1 | 11/2001 | Merchant |
| 2001/0054478 A1 | 12/2001 | Watanabe et al. |
| 2002/0007294 A1 | 1/2002 | Bradbury et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0062127 A1 | 5/2002 | Schumacher et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0116023 A1 | 8/2002 | Fletcher et al. |
| 2002/0120342 A1 | 8/2002 | Gibbs |
| 2002/0128872 A1 | 9/2002 | Giammattei |
| 2002/0147415 A1 | 10/2002 | Martelli |
| 2002/0173797 A1 | 11/2002 | Van Zile et al. |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198529 A1 | 12/2002 | Masini |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0028196 A1 | 2/2003 | Bonutti |
| 2003/0039676 A1 | 2/2003 | Boyce et al. |
| 2003/0055502 A1 | 3/2003 | Lang et al. |
| 2003/0060831 A1 | 3/2003 | Bonutti |
| 2003/0069897 A1 | 4/2003 | Roy et al. |
| 2003/0074800 A1 | 4/2003 | Huang |
| 2003/0100906 A1 | 5/2003 | Rosa et al. |
| 2003/0100907 A1 | 5/2003 | Rosa et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130665 A1 | 7/2003 | Pinczewski et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0212403 A1 | 11/2003 | Swanson |
| 2003/0212459 A1 | 11/2003 | Gibbs |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0018144 A1 | 1/2004 | Briscoe |
| 2004/0030245 A1 | 2/2004 | Noble et al. |
| 2004/0039395 A1 | 2/2004 | Coon et al. |
| 2004/0054372 A1 | 3/2004 | Corden et al. |
| 2004/0054416 A1* | 3/2004 | Wyss .................. A61F 2/3868 623/20.27 |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102785 A1 | 5/2004 | Hodorek et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0225369 A1 | 11/2004 | Lakin et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0249386 A1 | 12/2004 | Faoro |
| 2004/0254584 A1 | 12/2004 | Sarin et al. |
| 2004/0260301 A1 | 12/2004 | Lionberger et al. |
| 2005/0008887 A1 | 1/2005 | Heymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1 | 1/2005 | Gibbs |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbed et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113840 A1 | 5/2005 | Metzger et al. |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177170 A1 | 8/2005 | Fisher et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0209605 A1 | 9/2005 | Grimm et al. |
| 2005/0216305 A1 | 9/2005 | Funderud |
| 2005/0222571 A1 | 10/2005 | Ryan |

(56) References Cited

U.S. PATENT DOCUMENTS

| | | |
|---|---|---|
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0025778 A1 | 2/2006 | Ferree |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058809 A1 | 3/2006 | Zink et al. |
| 2006/0058884 A1 | 3/2006 | Aram et al. |
| 2006/0058886 A1 | 3/2006 | Wozencroft |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0095049 A1 | 5/2006 | Zannis et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122491 A1 | 6/2006 | Murray et al. |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0142774 A1 | 6/2006 | Metzger |
| 2006/0142778 A1 | 6/2006 | Dees |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0241775 A1 | 10/2006 | Buss |
| 2006/0241776 A1 | 10/2006 | Brown et al. |
| 2006/0241781 A1 | 10/2006 | Brown et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106391 A1 | 5/2007 | Ronk |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Staines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0270680 A1 | 11/2007 | Sheffer et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0014618 A1 | 1/2008 | Bathe et al. |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |

(56) References Cited

U.S. PATENT DOCUMENTS

| | | |
|---|---|---|
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262499 A1 | 10/2008 | Giori et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0287959 A1 | 11/2008 | Quest et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0312746 A1 | 12/2008 | Unger |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0022015 A1 | 1/2009 | Harrison |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0129067 A1 | 5/2009 | Fan |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0015082 A1 | 1/2010 | Ting-jenulis et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger et al. |
| 2010/0094295 A1 | 4/2010 | Schnieders et al. |

(56) References Cited

U.S. PATENT DOCUMENTS

| | | |
|---|---|---|
| 2010/0099977 A1 | 4/2010 | Hershberger |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276053 A1 | 11/2011 | Birkbeck et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0053590 A1 | 3/2012 | Allen et al. |
| 2012/0063655 A1 | 3/2012 | Dean et al. |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0190971 A1 | 7/2012 | De |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1 | 9/2012 | Kunz et al. |
| 2012/0259335 A1 | 10/2012 | Scifert et al. |

(56) References Cited

U.S. PATENT DOCUMENTS

| | | |
|---|---|---|
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289955 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2012/0330319 A1 | 12/2012 | Birkbeck et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'Neill et al. |
| 2013/0060253 A1 | 3/2013 | Couture et al. |
| 2013/0066323 A1 | 3/2013 | Nycz et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0116699 A1 | 5/2013 | Smith et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0158671 A1 | 6/2013 | Uthgenannt et al. |
| 2013/0197528 A1 | 8/2013 | Zakaria et al. |
| 2013/0197529 A1 | 8/2013 | Metzger et al. |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman et al. |
| 2013/0264749 A1 | 10/2013 | Jones et al. |
| 2013/0268085 A1 | 10/2013 | Dong et al. |
| 2013/0289730 A1 | 10/2013 | Gabriel et al. |
| 2013/0292870 A1 | 11/2013 | Roger |
| 2013/0317511 A1 | 11/2013 | Bojarski et al. |
| 2013/0317621 A1 | 11/2013 | Metzger et al. |
| 2013/0326878 A1 | 12/2013 | Boehm et al. |
| 2013/0338673 A1 | 12/2013 | Keppler |
| 2014/0001226 A1 | 1/2014 | Scabin et al. |
| 2014/0005672 A1 | 1/2014 | Edwards et al. |
| 2014/0012266 A1 | 1/2014 | Bonin, Jr. et al. |
| 2014/0018934 A1 | 1/2014 | Meridew et al. |
| 2014/0052270 A1 | 2/2014 | Witt et al. |
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson et al. |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0150688 A1 | 6/2015 | Vanasse et al. |
| 2015/0157341 A1 | 6/2015 | Catanzarite et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2016/0008013 A1 | 1/2016 | Metzger et al. |
| 2016/0038160 A1 | 2/2016 | Metzger |
| 2016/0100845 A1 | 4/2016 | Smith et al. |
| 2016/0135824 A1 | 5/2016 | Vanasse et al. |
| 2016/0196651 A1 | 7/2016 | Dean et al. |
| 2016/0203241 A1 | 7/2016 | Dean et al. |
| 2016/0213491 A1 | 7/2016 | Schoenefeld et al. |
| 2016/0228133 A1 | 8/2016 | Meridew et al. |
| 2016/0338838 A1 | 11/2016 | Meridew et al. |
| 2017/0000626 A1 | 1/2017 | White et al. |
| 2017/0056030 A1 | 3/2017 | Metzger et al. |
| 2017/0224496 A1 | 8/2017 | Witt et al. |
| 2017/0273718 A1 | 9/2017 | Metzger et al. |
| 2017/0311846 A1 | 11/2017 | Hershberger |
| 2017/0333194 A1 | 11/2017 | Pierce et al. |
| 2018/0008292 A1 | 1/2018 | Metzger et al. |
| 2018/0140426 A1 | 5/2018 | Belcher et al. |
| 2018/0153565 A1 | 6/2018 | Stone et al. |
| 2018/0168690 A1 | 6/2018 | Uthgenannt et al. |
| 2018/0168822 A1 | 6/2018 | White et al. |
| 2018/0206888 A1 | 7/2018 | Metzger et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CH | 117960 A | 5/1927 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 337437 C | 5/1921 |
| DE | 3447365 A1 | 7/1986 |
| DE | 04219939 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |

(56) References Cited

FOREIGN PATENT DOCUMENTS

| | | |
|---|---|---|
| EP | 1588669 A1 | 10/2005 |
| EP | 1634551 A2 | 3/2006 |
| EP | 1832239 A1 | 9/2007 |
| EP | 1852072 A2 | 11/2007 |
| EP | 1852072 A3 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| EP | 2816962 A1 | 12/2014 |
| EP | 2029061 B1 | 2/2017 |
| FR | 1111677 A | 3/1956 |
| FR | 2429582 A1 | 1/1980 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2423021 A | 8/2006 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| GB | 2486390 B | 11/2015 |
| GB | 2527690 B | 6/2016 |
| GB | 2483980 B | 12/2016 |
| GB | 2491526 B | 1/2017 |
| JP | 59157715 A | 9/1984 |
| JP | 60231208 A | 11/1985 |
| JP | 6-233790 A | 8/1994 |
| JP | 2000245758 A | 9/2000 |
| JP | 2004008797 A | 1/2004 |
| JP | 2005-218861 A | 8/2005 |
| JP | 2009514612 A | 4/2009 |
| JP | 2009515610 A | 4/2009 |
| JP | 2011505080 A | 2/2011 |
| JP | 2011517996 A | 6/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 | 5/2005 |
| TW | 201114409 A | 5/2011 |
| WO | WO-8807840 A1 | 10/1988 |
| WO | WO-8909028 A1 | 10/1989 |
| WO | WO-9014806 A1 | 12/1990 |
| WO | WO-9107139 A1 | 5/1991 |
| WO | WO-9325157 A1 | 12/1993 |
| WO | WO-9413218 A1 | 6/1994 |
| WO | WO-9528688 A1 | 10/1995 |
| WO | WO-9607361 A1 | 3/1996 |
| WO | WO-9729703 A1 | 8/1997 |
| WO | WO-9901073 A1 | 1/1999 |
| WO | WO-9952473 A1 | 10/1999 |
| WO | WO-9959106 A1 | 11/1999 |
| WO | WO-0110339 A2 | 2/2001 |
| WO | WO-0133511 A2 | 5/2001 |
| WO | WO-0170142 A1 | 9/2001 |
| WO | WO-0184479 A1 | 11/2001 |
| WO | WO-0217821 A2 | 3/2002 |
| WO | WO-2002026145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A2 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051209 A1 | 6/2005 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2005099636 A1 | 10/2005 |
| WO | WO-06058057 A2 | 6/2006 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A1 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2007145937 A3 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010045537 A1 | 4/2010 |
| WO | WO-2010048257 A1 | 4/2010 |
| WO | WO-2010088696 A1 | 8/2010 |
| WO | WO-2010093902 A1 | 8/2010 |
| WO | WO-2010096553 A1 | 8/2010 |
| WO | WO-2010096557 A1 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011063231 A1 | 5/2011 |
| WO | WO-2011019797 A3 | 7/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |

(56) References Cited

FOREIGN PATENT DOCUMENTS

| | | |
|---|---|---|
| WO | WO-2012174008 A1 | 12/2012 |
| WO | WO-2013126416 A1 | 8/2013 |
| WO | WO-2013170872 A1 | 11/2013 |
| WO | WO-2014019712 A1 | 2/2014 |
| WO | WO-2015084831 A1 | 6/2015 |
| WO | WO-2016007631 A1 | 1/2016 |

OTHER PUBLICATIONS

"U.S. Appl. No. 12/255,945, Notice of Allowance dated May 5, 2017", 7 pgs.
"U.S. Appl. No. 13/041,883, Examiner's Answer dated Mar. 8, 2017", 8 pgs.
"U.S. Appl. No. 13/041,883, Reply Brief Filed May 2, 2017 to Examiner's Answer dated Mar. 8, 2017", 8 pgs.
"U.S. Appl. No. 13/527,981, Examiner Interview Summary dated Apr. 24, 2017", 5 pgs.
"U.S. Appl. No. 13/527,981, Final Office Action dated Feb. 8, 2017", 17 pgs.
"U.S. Appl. No. 13/527,981, Non Final Office Action dated Jun. 22, 2017", 6 pgs.
"U.S. Appl. No. 13/527,981, Response filed May 8, 2017 to Final Office Action dated Feb. 8, 2017", 18 pgs.
"U.S. Appl. No. 13/800,334, Final Office Action dated Jun. 15, 2017", 22 pgs.
"U.S. Appl. No. 13/800,334, Response filed Mar. 15, 2017 to Non Final Office Action dated Dec. 15, 2016", 16 pgs.
"U.S. Appl. No. 14/064,970, Notice of Allowability dated Feb. 10, 2017", 2 pgs.
"U.S. Appl. No. 14/064,970, Notice of Allowability dated Feb. 17, 2017", 2 pgs.
"U.S. Appl. No. 14/064,970, Notice of Allowance dated Jan. 27, 2017", 10 pgs.
"U.S. Appl. No. 14/105,669, Notice of Allowance dated Jan. 26, 2017", 7 pgs.
"U.S. Appl. No. 14/327,234, Response filed May 17, 2017 to Restriction Requriement dated Apr. 6, 2017", 8 pgs.
"U.S. Appl. No. 14/327,234, Restriction Requirement dated Apr. 6, 2017", 7 pgs.
"U.S. Appl. No. 14/483,214, Examiner Interview Summary dated Apr. 12, 2017", 3 pgs.
"U.S. Appl. No. 14/483,214, Non Final Office Action dated May 2, 2017", 10 pgs.
"U.S. Appl. No. 14/658,429, Final Office Action dated Jun. 15, 2017", 7 pgs.
"U.S. Appl. No. 14/658,429, Non Final Office Action dated Feb. 23, 2017", 6 pgs.
"U.S. Appl. No. 14/658,429, Response Filed May 19, 2017 to Non-Final Office Action dated Feb. 23, 2017", 15 pgs.
"U.S. Appl. No. 14/798,809, Response filed Apr. 3, 2017 to Restriction Requirement dated Jan. 4, 2017", 8 pgs.
"U.S. Appl. No. 14/812,583, Non Final Office Action dated May 9, 2017", 14 pgs.
"U.S. Appl. No. 14/812,583, Response filed Mar. 16. 2017 to Restriction Requirement dated Jan. 23, 2017", 6 pgs.
"U.S. Appl. No. 14/812,583, Restriction Requirement dated Jan. 23, 2017", 8 pgs.
"U.S. Appl. No. 14/865,762, Non Final Office Action dated Jun. 13, 2017", 13 pgs.
"U.S. Appl. No. 14/865,762, Response filed May 17, 2017 to Restrictiion Requirement dated Apr. 13, 2017", 8 pgs.
"U.S. Appl. No. 14/865,762, Restriction Requirement dated Apr. 13, 2017", 6 pgs.
"U.S. Appl. No. 14/973,057, Corrected Notice of Allowance dated May 30, 2017", 2 pgs.
"U.S. Appl. No. 14/973,057, Final Office Action dated Feb. 13, 2017", 7 pgs.
"U.S. Appl. No. 14/973,057, Notice of Allowance dated Apr. 27, 2017", 7 pgs.
"U.S. Appl. No. 14/973,057, Response filed Jan. 18, 2017 to Non Final Office Action dated Oct. 18, 2016", 8 pgs.
"U.S. Appl. No. 14/973,057, Response filed Apr. 5, 2017 to Final Office Action dated Feb. 13, 2017", 9 pgs.
"U.S. Appl. No. 15/130,414, Preliminary Amendment filed Mar. 9, 2017", 6 pgs.
"U.S. Appl. No. 15/267,714, Non Final Office Action dated May 10, 2017", 23 pgs.
"U.S. Appl. No. 15/267,714, Response filed Feb. 28, 2017 to Restriction Requirement dated Jan. 5, 2017", 8 pgs.
"U.S. Appl. No. 15/352,721, Corrected Notice of Allowance dated Apr. 27, 2017", 2 pgs.
"U.S. Appl. No. 15/352,721, Notice of Allowance dated Mar. 10, 2017", 11 pgs.
"U.S. Appl. No. 15/352,721, Preliminary Amendment filed Feb. 3, 2017", 6 pgs.
"U.S. Appl. No. 15/495,432, Preliminary Amendment filed May 17, 2017", 8 pgs.
"European Application Serial No. 09731923.0, Response filed Apr. 10, 2017 to Communication Pursuant to Article 94(3) EPC dated Nov. 29, 2016", 18 pgs.
"European Application Serial No. 09732174.9, Response filed Feb. 22, 2017 to Communication Pursuant to Article 94(3) EPC dated Oct. 17, 2016", 6 pgs.
"European Application Serial No. 12724475.4, Response filed Jan. 10, 2017 to Communication Pursuant to Article 94(3) EPC dated Aug. 31, 2016", 17 pgs.
"European Application Serial No. 16179349.2, Extended European Search Report dated Mar. 22, 2017", 9 pgs.
"International Application Serial No. PCT/US2015/039561, International Preliminary Report on Patentability dated Jan. 19, 2017", 8 pgs.
U.S. Appl. No. 15/672,724, filed Aug. 9, 2017, Patient-Specific Augments.
U.S. Appl. No. 15/650,035, filed Jul. 14, 2017, Mechanical Axis Alignment Using MRI Imaging.
U.S. Appl. No. 15/712,679, filed Sep. 22, 2017, Patient-Specific Knee Alignment Guide and Associated Method.
U.S. Appl. No. 11/363,548 U.S. Pat. No. 7,780,672, filed Feb. 27, 2006, Femoral Adjustment Device and Associated Method.
U.S. Appl. No. 11/756,057 U.S. Pat. No. 8,092,465, filed May 31, 2007, Patient Specific Knee Alignment Guide and Associated Method.
U.S. Appl. No. 13/303,546 U.S. Pat. No. 8,398,646, filed Nov. 23, 2011, Patient-Specific Knee Alignment Guide and Associated Method.
U.S. Appl. No. 13/800,334, filed Mar. 13, 2013, Patient-Specific Knee Alignment Guide and Associated Method.
U.S. Appl. No. 12/103,834 U.S. Pat. No. 7,967,868, filed Apr. 16, 2008, Patient-Modified Implant and Associated Method.
U.S. Appl. No. 12/103,824, filed Apr. 16, 2008, Method and Apparatus for Manufacturing an Implant.
U.S. Appl. No. 13/081,618 U.S. Pat. No. 8,486,150, filed Apr. 7, 2011, Patient-Modified Implant.
U.S. Appl. No. 13/923,827 U.S. Pat. No. 8,979,936, filed Jun. 21, 2013, Patient-Modified Implant
U.S. Appl. No. 14/658,429, filed Mar. 16, 2015, Patient-Modified Implant.
U.S. Appl. No. 13/041,883, filed Mar. 7, 2011, Patient-Specific Femoral Guide.
U.S. Appl. No. 15/130,414, filed Apr. 15, 2016, Patient-Specific Acetabular Guides and Associated Instruments.
U.S. Appl. No. 13/041,495 U.S. Pat. No. 8,864,769, filed Mar. 7, 2011, Alignment Guides With Patient-Specific Anchoring Elements.
U.S. Appl. No. 13/041,469 U.S. Pat. No. 8,608,749, filed Mar. 7, 2011, Patient-Specific Acetabular Guides and Associated Instruments.
U.S. Appl. No. 13/047,924, filed Mar. 15, 2011, Patient-Specific Augments.
U.S. Appl. No. 13/045,169, filed Mar. 10, 2011, Instrument With Transparent Portion for Use With Patient-Specific Alignment Guide.
U.S. Appl. No. 13/400,652 U.S. Pat. No. 9,339,278, filed Feb. 21, 2012, Patient-Specific Acetabular Guides and Associated Instruments.

(56) References Cited

OTHER PUBLICATIONS

U.S. Appl. No. 14/483,214, filed Sep. 11, 2014, Alignment Guides With Patient-Specific Anchoring Elements.
U.S. Appl. No. 14/105,669, filed Dec. 13, 2013, Patient-Specific Acetabular Guides and Associated Instruments.
U.S. Appl. No. 14/812,583, filed Jul. 29, 2015, Patient-Specific Augments.
U.S. Appl. No. 12/872,663 U.S. Pat. No. 8,407,067, filed Aug. 31, 2010, Method and Apparatus for Manufacturing an Implant.
U.S. Appl. No. 13/766,419, filed Feb. 13, 2013, Method and Apparatus for Manufacturing an Implant.
U.S. Appl. No. 11/971,390 U.S. Pat. No. 8,070,752, filed Jan. 9, 2008, Patient Specific Alignment Guide and Inter-Operative Adjustment.
U.S. Appl. No. 12/025,414 U.S. Pat. No. 8,298,237, filed Feb. 4, 2008, Patient-Specific Alignment Guide for Multiple Incisions.
U.S. Appl. No. 12/371,096, filed Feb. 13, 2009, Method and Apparatus for Manufacturing an Implant.
U.S. Appl. No. 12/483,807 U.S. Pat. No. 8,473,305, filed Jun. 12, 2009, Method and Apparatus for Manufacturing an Implant.
U.S. Appl. No. 12/039,849 U.S. Pat. No. 8,282,646, filed Feb. 29, 2008, Patient Specific Knee Alignment Guide and Associated Method.
U.S. Appl. No. 12/211,407 U.S. Pat. No. 8,608,748, filed Sep. 16, 2008, Patient Specific Guides.
U.S. Appl. No. 14/107,316 U.S. Pat. No. 9,480,490, filed Dec. 16, 2013, Patient-Specific Guides.
U.S. Appl. No. 12/389,901 U.S. Pat. No. 8,133,234, filed Feb. 20, 2009, Patient Specific Acetabular Guide and Method.
U.S. Appl. No. 13/343,957 U.S. Pat. No. 8,900,244, filed Jan. 5, 2012, Patient Specific Acetabular Guide and Method.
U.S. Appl. No. 12/486,992 U.S. Pat. No. 8,858,561, filed Jun. 18, 2009, Patient-Specific Alignment Guide.
U.S. Appl. No. 12/571,969 U.S. Pat. No. 9,173,661, filed Oct. 1, 2009, Patient Specific Alignment Guide With Cutting Surface and Laser Indicator.
U.S. Appl. No. 14/865,762, filed Sep. 25, 2015, Patient Specific Alignment Guide With Cutting Surface And Laser Indicator.
U.S. Appl. No. 12/714,023 U.S. Pat. No. 8,241,293, filed Feb. 26, 2010, Patient Specific High Tibia Osteotomy.
U.S. Appl. No. 13/572,895 U.S. Pat. No. 8,828,087, filed Aug. 13, 2012, Patient-Specific High Tibia Osteotomy.
U.S. Appl. No. 12/888,005 U.S. Pat. No. 8,377,066, filed Sep. 22, 2010, Patient-Specific Elbow Guides and Associated Methods.
U.S. Appl. No. 13/744,022 U.S. Pat. No. 9,005,297, filed Jan. 17, 2013, Patient-Specific Elbow Guides and Associated Methods.
U.S. Appl. No. 14/684,936 U.S. Pat. No. 9,539,013, filed Apr. 13, 2015, Patient-Specific Elbow Guides and Associated Methods.
U.S. Appl. No. 12/893,306 U.S. Pat. No. 9,113,971, filed Sep. 29, 2010, Femoral Acetabular Impingement Guide.
U.S. Appl. No. 14/798,809, filed Jul. 14, 2015, Femoral Acetabular Impingement Guide.
U.S. Appl. No. 12/938,913 U.S. Pat. No. 9,289,253, filed Nov. 3, 2010, Patient-Specific Shoulder Guide.
U.S. Appl. No. 15/008,528, filed Jan. 28, 2016, Patient-Specific Shoulder Guide.
U.S. Appl. No. 12/938,905, filed Nov. 3, 2010, Patient-Specific Implants.
U.S. Appl. No. 12/955,361 U.S. Pat. No. 8,591,516, filed Nov. 29, 2010, Patient-Specific Orthopedic Instruments.
U.S. Appl. No. 12/973,214 U.S. Pat. No. 9,345,548, filed Dec. 20, 2010, Patient-Specific Pre-Operative Planning.
U.S. Appl. No. 15/093,384, filed Apr. 7, 2016, Patient-Specific Pre-Operative Planning.
U.S. Appl. No. 12/255,945, filed Oct. 22, 2008, Mechanical Axis Alignment Using MRI Imaging.
U.S. Appl. No. 12/978,069 U.S. Pat. No. 8,568,487, filed Dec. 23, 2010, Patient-Specific Hip Joint Devices.
U.S. Appl. No. 14/064,970, filed Oct. 28, 2013, Patient-Specific Hip Joint Devices.
U.S. Appl. No. 13/041,665 U.S. Pat. No. 8,535,387, filed Mar. 7, 2011, Patient-Specific Tools and Implants.
U.S. Appl. No. 14/027,340 U.S. Pat. No. 9,445,907, filed Sep. 16, 2013, Patient-Specific Tools and Implants.
U.S. Appl. No. 15/224,741, filed Aug. 1, 2016, Patient-Specific Tools and Implants.
U.S. Appl. No. 13/111,007 U.S. Pat. No. 8,603,180, filed May 19, 2011, Patient-Specific Acetabular Guides and Associated Instruments.
U.S. Appl. No. 14/100,134 U.S. Pat. No. 9,480,580, filed Dec. 9, 2013, Patient-Specific Acetabular Alignment Guides.
U.S. Appl. No. 15/267,714, filed Sep. 16, 2016, Patient-Specific Acetabular Alignment Guides.
U.S. Appl. No. 13/527,981, filed Jun. 20, 2012, Backup Surgical Instrument System and Method.
U.S. Appl. No. 14/327,234, filed Jul. 9, 2014, Patient-Specific Knee Alignment Guide and Associated Method.
U.S. Appl. No. 13/713,710 U.S. Pat. No. 9,241,745, filed Dec. 13, 2012, Patient-Specific Femoral Version Guide
U.S. Appl. No. 14/973,057, filed Dec. 17, 2015, Patient-Specific Femoral Version Guide.
U.S. Appl. No. 13/106,295 U.S. Pat. No. 8,632,547, filed May 12, 2011, Patient-Specific Osteotomy Devices and Methods.
U.S. Appl. No. 14/086,447 U.S. Pat. No. 9,522,010, filed Nov. 21, 2013, Patient-Specific Orthopedic Instruments.
U.S. Appl. No. 15/352,721, filed Nov. 16, 2016, Patient-Specific Orthopedic Instruments.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (Oct. 31, 1999) 16 sheets.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.
"Comprehensive® Total Shoulder System," Biomet Orthopedics brochure (2011), 4 pages.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"Hipsextant Instructions of Use." (2011) Surgical Planning Associates, Inc. 19 pages.
"Is Subchondroplasty® Right for Me?" Retrieved from <http://www.subchondroplasty.com/about_subchondroplasty/is_subchondroplasty_right_for_> . . . Jul. 1, 2013. 1 sheet.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.
"Regenerex® Tibial Cone Augment, Surgical Technique Addendum to the Vanguard® SSK Revision System," brochure. Biomet® Orthopedics. (Mar. 31, 2010) pp. 1-8 (12 sheets).
"Signature™ Personalized Patient Care, Surgical Technique Addendum to the Vanguard Knee System" brochure. Biomet® Orthopedics, Inc. (May 15, 2009) pp. 1-8.

(56) References Cited

OTHER PUBLICATIONS

"Subchondroplasty," Retrieved from <http://www.subchondroplasty.com/>. Jul. 1, 2013. 1 sheet.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (Aug. 31, 2010) pp. 1-25.
"Zimmer® UniSpacer® Knee System," brochure. (2005) Zimmer, Inc. 4 sheets.
Biomet "Oxford® Partial Knee" brochure, 8 pages (Feb. 2011).
Biomet "The Oxford® Partial Knee Surgical Technique," brochure, pp. 1-38, (Feb. 2010).
Biomet, "Oxford® Partial Knee Microplasty® Instrumentation Surgical Technique", brochure, pp. 1-54 (May 2011).
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Deakon, Timothy, MD, Posterior Cruciate Ligament Reconstruction Technique Using the Modular ACL/PCL Guide Rationale and Surgical Technique, Arthrotek®, a Biomet Company. (2003). (6 pages).
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
European Communication Pursuant to Article 94(3) EPC dated Jan. 22, 2015 for PCT/US2007/013223 filed Jun. 5, 2007, which claims benefit of U.S. Appl. No. 60/812,694, filed Jun. 9, 2006 and U.S. Appl. No. 11/756,057, filed May 31, 2007.
European Communication Pursuant to Article 94(3) EPC dated Feb. 4, 2015 for PCT/US2010/024584 filed Feb. 18, 2010, which claims benefit of U.S. Appl. No. 12/389,901, filed Feb. 20, 2009.
European Communication Pursuant to Article 94(3) EPC dated Feb. 10, 2015 for PCT/US2009/039507 filed Apr. 3, 2009, which claims benefit of U.S. Appl. No. 12/103,824, filed Apr. 16, 2008.
European Communication Pursuant to Article 94(3) EPC dated Nov. 24, 2014 for PCT/US2012/038351 which claims benefit of U.S. Appl. No. 13/111,007, filed May 19, 2011.
Farr, J., Cole, B., Kercher, J., Batty, L. and Bajaj, S., Anteromedial Tibial Tubercle Osteotomy (Fulkerson Osteotomy). Re-print from V. Sanchis-Alfonso (ed), Anterior Knee Pain and patellar Instability, DOI: 10.1007/978-0-85729-507-1_40, © Springer-Verlag London Limited 2011.(9 pages).
Farr, J., Fulkerson, J. Surgical Technique for Anteromedialization of the Tibial Tubercle with the Tracker™ AMZ Guide System. Sports Medicine and Arthroscopy Review, vol. 2, No. 3, 1994. (12 pages).
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Friedman, R.J. et al., "The Use of Computerized Tomography in the Measurement of Glenoid Version", Journal of Bone & Joint Surgery Am. (JBJS) 1992;74:1032-1037 (Aug. 1992).
Genant, H.K. et al., Advanced CT bone imaging in osteoporosis, Rheumatology, 47:iv9-iv16 (2008).
Great Britain Search Report dated Dec. 21, 2011 for GB1116054.6, claiming benefit of U.S. Appl. No. 12/888,005, filed Sep. 22, 2010.
Guldberg et al., 3D Imaging of Tissue Integration with Porous Biomaterials, Biomaterials, 29(28): 3757-3761 (Oct. 2008).
Haaker, R.G., et al., "Minimal-invasive navigiert implantierte unikondylare Knieendoprothese," Orthopade 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazen, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion dated Jan. 5, 2012 for PCT/US2010/038845 claiming benefit of U.S. Appl. No. 12/486,992, filed Jun. 18, 2009.
International Preliminary Report on Patentability and Written Opinion for PCT/US2009/039578 dated Oct. 28, 2010 claiming benefit of U.S. Appl. No. 12/103,834, filed Apr. 16, 2008.
International Preliminary Report on Patentability and Written Opinion dated Apr. 24, 2014 for PCT/US2012/059189 claiming benefit of U.S. Appl. No. 13/597,478, filed Aug. 29, 2012.
International Preliminary Report on Patentability and Written Opinion dated Dec. 22, 2011 for PCT/US2010/038177 claiming benefit of U.S. Appl. No. 12/483,807, filed Jun. 12, 2009.
International Preliminary Report on Patentability and Written Opinion dated Jan. 3, 2014 for PCT/US2012/042081 claiming benefit of U.S. Appl. No. 13/493,509, filed Jun. 11, 2012.
International Preliminary Report on Patentability and Written Opinion dated Mar. 13, 2014 for PCT/US2012/052853 claiming benefit of U.S. Appl. No. 13/221,968, filed Aug. 31, 2011.
International Preliminary Report on Patentability and Written Opinion dated May 8, 2014 for PCT/US2012/060842 claiming benefit of U.S. Appl. No. 13/653,868, filed Oct. 17, 2012.
International Preliminary Report on Patentability and Written Opinion dated May 8, 2014 for PCT/US2012/060848 claiming benefit of U.S. Appl. No. 13/653,878, filed Oct. 17, 2012.
International Preliminary Report on Patentability and Written Opinion dated May 8, 2014 for PCT/US2012/060853 claiming benefit of U.S. Appl. No. 13/653,886, filed Oct. 17, 2012.
International Preliminary Report on Patentability and Written Opinion dated May 8, 2014 for PCT/US2012/060854 claiming benefit of U.S. Appl. No. 13/653,893, filed Oct. 17, 2012.
International Preliminary Report on Patentability and Written Opinion dated Nov. 28, 2013 for PCT/US2012/038351 claiming benefit of U.S. Appl. No. 13/111,007, filed May 19, 2011.
International Preliminary Report on Patentability and Written Opinion dated Oct. 28, 2010 for PCT/US2009/039507 claiming benefit of U.S. Appl. No. 12/103,824, filed Apr. 16, 2008.
International Preliminary Report on Patentability and Written Opinion dated Mar. 12, 2015 for PCT/US2013/057097 claiming benefit of U.S. Appl. No. 13/597,478, filed Aug. 29, 2012.
International Preliminary Report on Patentability and Written Opinion dated May 14, 2015 for PCT/US2013/067505 claiming benefit of U.S. Appl. No. 13/718,129, filed Dec. 18, 2012.
International Preliminary Report on Patentability and Written Opinion dated Sep. 7, 2012 for PCT/US2011/026333 claiming benefit of U.S. Appl. No. 12/714,023, filed Feb. 26, 2010.
International Preliminary Report on Patentability for PCT/US2007/013223 dated Dec. 24, 2008 claiming benefit of U.S. Appl. No. 11/756,057, filed May 31, 2007.
International Preliminary Report on Patentability for PCT/US2010/050701 dated Apr. 12, 2012 claiming benefit of U.S. Appl. No. 12/571,969, filed Oct. 1, 2009.
International Preliminary Report on Patentability dated Aug. 25, 2011 for PCT/US2010/024073 filed Feb. 12, 2010, claiming benefit of U.S. Appl. No. 12/371,096, filed Feb. 13, 2009.
International Preliminary Report on Patentability dated Mar. 31, 2011 for PCT/US2009/056670 claiming benefit of U.S. Appl. No. 12/211,407, filed Sep. 16, 2008.
International Preliminary Report on Patentability dated Sep. 1, 2011 for PCT/US2010/024579 claiming benefit of U.S. Appl. No. 12/389,930, filed Feb. 20, 2009.

(56) References Cited

OTHER PUBLICATIONS

International Preliminary Report on Patentability dated Sep. 1, 2011 for PCT/US2010/024584 claiming benefit of U.S. Appl. No. 12/389,901, filed Feb. 20, 2009.
International Preliminary Report on Patentability dated Sep. 6, 2013 for PCT/US2012/026356 claiming benefit of U.S. Appl. No. 13/041,883, filed Mar. 7, 2011.
International Preliminary Report on Patentability Report and Written Opinion dated Sep. 4, 2014 for PCT/US2013/026875 claiming benefit of U.S. Appl. No. 13/400,652, filed Feb. 21, 2012.
International Search Report and Written Opinion for PCT/US2007/013223 dated Nov. 26, 2007, claiming benefit of U.S. Appl. No. 11/756,057, filed May 31, 2007.
International Search Report and Written Opinion for PCT/US2009/039507 dated Jul. 14, 2009, claiming benefit of U.S. Appl. No. 12/103,824, filed Apr. 16, 2008.
International Search Report and Written Opinion for PCT/US2009/056670 dated Mar. 2, 2010 claiming benefit of U.S. Appl. No. 12/211,407, filed Sep. 16, 2008.
International Search Report and Written Opinion for PCT/US2013/026875 dated Jun. 7, 2013, claiming benefit of U.S. Appl. No. 13/400,652, filed Feb. 21, 2012.
International Search Report and Written Opinion dated Apr. 14, 2014 for PCT/US2013/067505 claiming benefit of U.S. Appl. No. 13/718,129, filed Dec. 18, 2012.
International Search Report and Written Opinion dated Apr. 22, 2010 for PCT/US2010/024579 claiming benefit of U.S. Appl. No. 12/389,930, filed Feb. 20, 2009.
International Search Report and Written Opinion dated Aug. 19, 2010 for PCT/US2010/024584 claiming benefit of U.S. Appl. No. 12/389,901, filed Feb. 20, 2009.
International Search Report and Written Opinion dated Aug. 24, 2010 for PCT/US2010/038177 claiming benefit of U.S. Appl. No. 12/483,807, filed Jun. 12, 2009.
International Search Report and Written Opinion dated Aug. 9, 2011 for PCT/US2011/026333 claiming benefit of U.S. Appl. No. 12/714,023, filed Feb. 26, 2010.
International Search Report and Written Opinion dated Dec. 18, 2012 for PCT/US2012/059189, which claims benefit of U.S. Appl. No. 13/597,478, filed Aug. 29, 2011.
International Search Report and Written Opinion dated Dec. 7, 2010 for PCT/US2010/050701 claiming benefit of U.S. Appl. No. 12/571,969, filed Oct. 1, 2009.
International Search Report and Written Opinion dated Feb. 6, 2013 for PCT/US2012/060842, which claims benefit of U.S. Appl. No. 13/653,868, filed Oct. 17, 2012.
International Search Report and Written Opinion dated Feb. 6, 2013 for PCT/US2012/060854, which claims benefit of U.S. Appl. No. 13/653,893, filed Oct. 17, 2012.
International Search Report and Written Opinion dated Jul. 10, 2014 for PCT/US2014/023655 claiming benefit of U.S. Appl. No. 13/800,369, filed Mar. 13, 2013.
International Search Report and Written Opinion dated Jul. 31, 2009 for PCT/US2009/039578 claiming benefit of U.S. Appl. No. 12/103,834, filed Apr. 16, 2008.
International Search Report and Written Opinion dated Jun. 24, 2014 for PCT/US2014/022000 claiming benefit of U.S. Appl. No. 13/889,869, filed May 8, 2013.
International Search Report and Written Opinion dated Jun. 4, 2010 for PCT/US2010/024073 filed Feb. 12, 2010 claiming benefit of U.S. Appl. No. 12/371,096, filed Feb. 13, 2009.
International Search Report and Written Opinion dated Mar. 5, 2012 for PCT/US2011/057300 claiming benefit of U.S. Appl. No. 12/938,905, filed Nov. 3, 2010.
International Search Report and Written Opinion dated May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.
International Search Report and Written Opinion dated May 8, 2012 for PCT/US2012/026356 claiming benefit of U.S. Appl. No. 13/041,883, filed Mar. 7, 2011.
International Search Report and Written Opinion dated May 9, 2011 for PCT/US2011/026412 claiming benefit of U.S. Appl. No. 12/872,663, filed Aug. 31, 2010.
International Search Report and Written Opinion dated Nov. 15, 2012, for PCT/US2012/052853, which claims benefit of U.S. Appl. No. 13/221,968, filed Aug. 31, 2011.
International Search Report and Written Opinion dated Oct. 14, 2013 for PCT/US2013/057097 claiming benefit of U.S. Appl. No. 13/597,478, filed Aug. 29, 2012.
International Search Report and Written Opinion dated Oct. 5, 2010 for PCT/US2010/038845 claiming benefit of U.S. Appl. No. 12/486,992, filed Jun. 18, 2009.
International Search Report dated Nov. 30, 2010 for PCT/EP2010/061630 filed Aug. 10, 2010 claiming benefit of DE102009028503.2 filed Aug. 13, 2009.
International Search Report dated Oct. 23, 2012, for PCT/US2012/041893, which claims benefit of U.S. Appl. No. 61/496,177, filed Jun. 13, 2011.
Invitation to Pay Additional Fees dated Feb. 6, 2013 for PCT/US2012/060848, which claims benefit of U.S. Appl. No. 13/653,878, filed Oct. 17, 2012.
Invitation to Pay Additional Fees dated Feb. 6, 2014 for PCT/US2013/067505, which claims benefit of U.S. Appl. No. 13/718,129, filed Dec. 18, 2012.
Invitation to Pay Additional Fees dated Feb. 7, 2013 for PCT/US2012/060853, which claims benefit of U.S. Appl. No. 13/653,893, filed Oct. 17, 2012.
Invitation to Pay Additional Fees dated May 3, 2011 for PCT/US2011/026333 claiming benefit of U.S. Appl. No. 12/714,023, filed Feb. 26, 2010.
Invitation to Pay Additional Fees with Partial International Search dated Nov. 26, 2009 for PCT/US2009/056670.
Japanese Office Action dated Apr. 7, 2015 for PCT/US2012/038351 filed May 17, 2012 claiming benefit of U.S. Appl. No. 13/111,007, filed May 19, 2011.
K. Subburaj et al., "Automated 3D Geometric Reasoning in Computer Assisted Joint Reconstructive Surgery", IEEE International Conference on Automation Science and Engineering, Publication Year: 2009, pp. 367-372.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-8. vol. 91-A, Supplement 1.
Klein, M., "Robot assisted insertion of craniofacial implants—clinical experience," Cars 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Patent Examiniation Report No. 1 dated Feb. 16, 2015 for PCT/US2013/026875 filed Feb. 20, 2013, which claims benefit of U.S. Appl. No. 13/400,652, filed Feb. 21, 2012.
Patsch, J.M. et al., Noninvasive imaging of bone microarchitecture, Annals ofthe NY Academy of Sciences, 1240:77-87 (2011)—Abstract only.

(56) References Cited

OTHER PUBLICATIONS

Portheine, F., "CT-basierte Planung und DISOS-Schablonennavigation in der Kniegelenkendoprothetik," in Navigation und Robotic in der Gelenk—und Wirbelsaulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology arid Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lipincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.
Regenerex® Porous Titanium Construct, Biomet Orthopedics, 12 pages (2011).
Schuller-Götzburg, P., et al., 3D-Implantatplanung und Stereolithographie-Implantatbohrschablonen, Stomatologie 101.3, pp. 55-59 (May 2004).
Sharp, S. Michael, Ph.D., Patient-Specific, Resurfacing Bi-Compartmental Arthuroplasty, Futuretech, Orthopaedic Product News (Mar./Apr. 2008) pp. 12-15.
Signature™ Hip Technology Personalized Patient Care brochure, Biomet® Orthopedics. (2013) (8 pages).
Signature™ Personalized Patient Care, Surgical Technique Addendum Vanguard® Complete Knee System, Biomet® Orthopedics Brochure, (2011), pp. 1-32.
Signature™ Personalized Patient Care. Surgical Technique Acetabular Guide System brochure. Biomet® Orthopedics. (2013) pp. 1-13.
Sisto, Domenick, J., et al., "Custom Patellofemoral Arthroplasty of the Knee Surgical Technique," Journal of Bone and Joint Surgery, vol. 89-A, pp. 214-225 (Jul. 2006).
Slammin, John et al, "Do You Have This Implant in My Size?", MDT Medical Design Technology, 3 pages, http://www.mdtmag.com/scripts/ShowPR.asp?PUBCODE.046&ACCT=0007796&ISSUE . . . accessed Jul. 31, 2008.
Steinwachs, Matthias Reinhard, "Cartilage Repair—Autologous Chondrocyte Transplantation and Autologous Matrix-induced Chondrogenesis," European Musculoskeletal Review (2006) pp. 65-68.
Supplementary European Search Report dated Nov. 15, 2011 for EP07809326, which claims benefit of PCT/US2007/013223, filed Jun. 5, 2007; which claims benefit of U.S. Appl. No. 11/756,057, filed May 31, 2007.
Thomas, W., et al., "Endoprothetischen Versorgung des Kniegelenks auf der Basis eines 3D-computertomographischen Subtraktionsverfahrens," Zuma Thema: Computergestutzte orthopadische Chirugie, Der Orthopade 29:641-644 Springer-Verlag (Jul. 2000) Translation provided: Thomas, W., "Endoprosthetic care of the knee joint based on a 3D computer chromatography subtraction process," Topic: Computer-aided orthopedic surgery. Orthopedist 2000 29:641-644 Springer Verlag (Jul. 2000).
Tripp et al., A Nondestructive Prescreening Method for Bone Collagen Content Using Micro-Computed Tomography, Radiocarbon, vol. 52, Nr2-3, pp. 612-619 (2010).
Vanguard, System Summary, Vanguard Complete Knee System, Biomet Othopedics, 8 pages (2011).
What is Subchondroplasty, Retrieved from <http://www.subchondroplasty.com/about_subchondroplasty/what_is_subchondroplasty. >, Jul. 1, 2013. 2 sheets.
U.S. Appl. No. 15/911,701, filed Mar. 5, 2018, Virtual Surgery Planning System and Method.
U.S. Appl. No. 15/878,984, filed Jan. 24, 2018, Alignment Guides With Patient-Specific Anchoring Elements.
U.S. Appl. No. 15/875,204, filed Jan. 19, 2018, Method and Apparatus for Manufacturing an Implant.
U.S. Appl. No. 15/863,421, filed Jan. 5, 2018, Patient-Specific Acetabular Alignment Guides.
U.S. Appl. No. 15/887,740, filed Feb. 2, 2018, Backup Surgical Instrument System and Method.
U.S. Appl. No. 15/933,576, filed Mar. 23, 2018, Patient-Specific Orthopedic Instruments.
"U.S. Appl. No. 14/798,809, Corrected Notice of Allowability dated Jun. 27, 2018", 4 pgs.
"U.S. Appl. No. 14/798,809, Notice of Allowance dated May 3, 2018", 7 pgs.
"U.S. Appl. No. 14/865,762, Response filed Jun. 8, 2018 to Non Final Office Action dated Mar. 8, 2018", 17 pgs.
"U.S. Appl. No. 15/008,528, Non Final Office Action dated Jun. 11, 2018", 13 pgs.
"U.S. Appl. No. 15/224,741, Non Final Office Action dated Jun. 11, 2018", 10 pgs.
"U.S. Appl. No. 15/224,741, Response filed May 14, 2018 to Restriction Requirement dated Mar. 15, 2018", 8 pgs.
"U.S. Appl. No. 15/495,432, Non Final Office Action dated May 9, 2018", 9 pgs.
"U.S. Appl. No. 15/887,740, Preliminary Amendment Filed Apr. 27, 2018", 8 pgs.
"U.S. Appl. No. 15/933,576, Preliminary Amendment Filed Apr. 17, 2018", 6 pgs.
"U.S. Appl. No. 15/972,591, Preliminary Amendment Filed May 21, 2018", 6 pgs.
"European Application Serial No. 10705951.1, Communication Pursuant to Article 94(3) EPC dated May 23, 2018", 7 pgs.
"U.S. Appl. No. 12/371,096, Corrected Notice of Allowance dated Nov. 13, 2017", 2 pgs.
"U.S. Appl. No. 12/371,096, Notice of Allowance dated Oct. 20, 2017", 5 pgs.
"U.S. Appl. No. 13/527,981, Corrected Notice of Allowance dated Nov. 27, 2017", 2 pgs.
"U.S. Appl. No. 13/527,981, Notice of Allowance dated Nov. 3, 2017", 5 pgs.
"U.S. Appl. No. 14/483,214, Final Office Action dated Oct. 25, 2017", 11 pgs.
"U.S. Appl. No. 14/658,429, Examiner Interview Summary dated Dec. 26, 2017", 2 pgs.
"U.S. Appl. No. 14/658,429, Final Office Action dated Oct. 20, 2017", 11 pgs.
"U.S. Appl. No. 14/658,429, Notice of Allowance dated Feb. 9, 2018", 8 pgs.
"U.S. Appl. No. 14/658,429, Response filed Jan. 4, 2018 to Final Office Action dated Oct. 20, 2017", 20 pgs.
"U.S. Appl. No. 14/798,809, Advisory Action dated Feb. 28, 2018", 3 pgs.
"U.S. Appl. No. 14/798,809, Final Office Action dated Dec. 29, 2017", 4 pgs.
"U.S. Appl. No. 14/798,809, Response filed Feb. 21, 2018 to Final Office Action dated Dec. 29, 2017", 7 pgs.
"U.S. Appl. No. 14/798,809, Response Filed Mar. 29, 2018 to Advisory Action dated Feb. 28, 2018", 8 pgs.

(56) References Cited

OTHER PUBLICATIONS

"U.S. Appl. No. 14/865,762, Final Office Action dated Mar. 8, 2018", 14 pgs.
"U.S. Appl. No. 15/008,528, Response filed Dec. 7, 2017 to Restriction Requirement dated Oct. 12, 2017", 7 pgs.
"U.S. Appl. No. 15/008,528, Restriction Requirement dated Oct. 12, 2017", 6 pgs.
"U.S. Appl. No. 15/130,414, Response filed Apr. 2, 2018 to Restriction Requirement dated Feb. 6, 2018", 7 pgs.
"U.S. Appl. No. 15/130,414, Response filed Nov. 6, 2017 to Restriction Requirement dated Sep. 20, 2017", 8 pgs.
"U.S. Appl. No. 15/130,414, Restriction Requirement dated Feb. 6, 2018", 8 pgs.
"U.S. Appl. No. 15/224,741, Restriction Requirement dated Mar. 15, 2018", 7 pgs.
"U.S. Appl. No. 15/267,714, Notice of Allowance dated Oct. 10, 2017", 13 pgs.
"U.S. Appl. No. 15/495,432, Response filed Apr. 4, 2018 to Restriction Requirement dated Feb. 9, 2018", 10 pgs.
"U.S. Appl. No. 15/495,432, Restriction Requirement dated Feb. 9, 2018", 8 pgs.
"U.S. Appl. No. 15/618,331, Notice of Allowance dated Jan. 10, 2018", 10 pgs.
"U.S. Appl. No. 15/712,679, Preliminary Amendment filed Oct. 12, 2017", 7 pgs.
"U.S. Appl. No. 15/863,421, Preliminary Amendment Filed Mar. 13, 2018", 9 pgs.
"U.S. Appl. No. 15/875,204, Preliminary Amendment filed Mar. 8, 2018", 9 pgs.
"U.S. Appl. No. 15/878,984, Preliminary Amendment Filed Mar. 9, 2018", 8 pgs.
"European Application Serial No. 16179349.2, Response filed Oct. 19, 2017 to Extended European Search Report dated Mar. 22, 2017", 17 pgs.
"European Application Serial No. 16179569.5, Response filed Feb. 7, 2018 to Extended European Search Report dated Jul. 7, 2017", 14 pgs.
"German Application Serial No. 1120111008104, Office Action dated Oct. 18, 2017", (W/ English translation of claims), 7 pgs.
"German Application Serial No. 1120111008104, Response filed Feb. 23, 2018 to Office Action dated Oct. 18, 2017", (W/ English translation of claims), 8 pgs.
Kwon, Oh-Ryong, et al., "The Effect of Femoral Cutting Guide Design Improvements for Patient-Specific Instruments", BioMed Research International, vol. 2015, Article ID 978686; https://www.hindawi.com/journals/bmri/2015/978686/, (Apr. 20, 2015), 9 pgs.
Macdessi, S., et al., "Patient-specific cutting guides for total knee arthroplasty", Cochrane Database of Systematic Reviews, Issue 3. Art. No. CD012589; http://onlinelibrary.wiley.com/doi/10.1002/14651858.CD012589/full, (Mar. 13, 2017), 16 pgs.
"3D-Implantatplanung und StereolithographieImplantatbohrschablonen", Stomatologie 101.3, (2004), 55-59.
"AGC 3000 Intramedullary",—Surgical Technique Using PMMA Fixation—Biomet, Inc., (1987), 32 pgs.
"AGC Distal Fem Cutter for Dr. Hardy", Biomet, Inc., (Jun. 22, 1989), 4 pgs.
"AGC Total Knee System, Intramedullary Without Distractor Surgical Technique", Biomet, Inc., (1989), 35 pgs.
"AGC Total Knee System, Unicondylar Surgical Overview", Biomet, Inc., (Jan. 31, 1989), 5 pgs.
"AGC Traditional Surgical Overview", Biomet Orthopedics, Inc., (2001), 8 pgs.
"AGC-S Total Knee System, Surgical Technique for the AGC-S Total Knee System", Biomet, Inc., (1992), 22 pgs.
"Anatomic Axial Alignment Instrumentation", Biomet, Inc., (1994), 24 pgs.
"U.S. Appl. No. 09/861,859, 312 Amendment filed Sep. 27, 2011", 3 pgs.

"U.S. Appl. No. 09/861,859, Final Office Action dated Aug. 5, 2011", 10 pgs.
"U.S. Appl. No. 09/861,859, Non Final Office Action dated Mar. 3, 2011", 9 pgs.
"U.S. Appl. No. 09/861,859, Notice of Allowance dated Sep. 8, 2011", 5 pgs.
"U.S. Appl. No. 09/861,859, Notice of Non Compliant Amendment dated Nov. 18, 2010", 3 pgs.
"U.S. Appl. No. 09/861,859, PTO Response to Rule 312 Communication dated Oct. 7, 2011", 2 pgs.
"U.S. Appl. No. 09/861,859, Response filed May 12, 2011 to Non-Final Office Action dated Mar. 3, 2011", 13 pgs.
"U.S. Appl. No. 09/861,859, Response filed Aug. 22, 2011 to Non Final Office Action dated Aug. 5, 2011", 9 pgs .
"U.S. Appl. No. 09/861,859, Response filed Oct. 28, 2010 to Restriction Requirement dated Sep. 29, 2010", 1 pg.
"U.S. Appl. No. 09/861,859, Response filed Nov. 29, 2010 to Notice of Non Compliant Amendment dated Nov. 18, 2010", 8 pgs.
"U.S. Appl. No. 09/861,859, Restriction Requirement dated Sep. 29, 2010", 7 pgs.
"U.S. Appl. No. 11/363,548, Advisory Action dated Aug. 5, 2009", 2 pgs.
"U.S. Appl. No. 11/363,548, Appeal Brief filed Jun. 19, 2009", 52 pgs.
"U.S. Appl. No. 11/363,548, Final Office Action dated Jan. 22, 2009", 12 pgs.
"U.S. Appl. No. 11/363,548, Non Final Office Action dated Jul. 9, 2008", 11 pgs.
"U.S. Appl. No. 11/363,548, Notice of Allowance dated Apr. 9, 2010", 5 pgs.
"U.S. Appl. No. 11/363,548, Response filed Jun. 19, 2009 to Final Office Action dated Jan. 22, 2009", 9 pgs.
"U.S. Appl. No. 11/363,548, Response filed Oct. 8, 2008 to Non Final Office Action dated Jul. 9, 2008", 18 pgs.
"U.S. Appl. No. 11/971,390, Non Final Office Action dated Mar. 3, 2011", 7 pgs.
"U.S. Appl. No. 11/971,390, Notice of Allowance dated Jul. 26, 2011", 8 pgs.
"U.S. Appl. No. 11/971,390, Preliminary Amendment filed Jan. 14, 2011", 8 pgs.
"U.S. Appl. No. 11/971,390, Response filed May 12, 2011 to Non Final Office Action dated Mar. 3, 2011", 12 pgs.
"U.S. Appl. No. 11/971,390, Response filed Dec. 23, 2010 to Restriction Requirement dated Nov. 23, 2010", 1 pgs.
"U.S. Appl. No. 11/971,390, Restriction Requirement dated Nov. 23, 2010", 6 pgs.
"U.S. Appl. No. 12/039,849, Final Office Action dated Apr. 8, 2012", 7 pgs.
"U.S. Appl. No. 12/039,849, Non Final Office Action dated Mar. 8, 2012", 11 pgs.
"U.S. Appl. No. 12/039,849, Notice of Allowance dated Jun. 6, 2012", 7 pgs.
"U.S. Appl. No. 12/039,849, Response filed Apr. 3, 2012 to Non Final Office Action dated Mar. 8, 2012", 19 pgs.
"U.S. Appl. No. 12/039,849, Response filed May 14, 2012 to Final Office Action dated Apr. 8, 2012", 7 pgs.
"U.S. Appl. No. 12/039,849, Response filed Aug. 30, 2011 to Restriction Requirement dated Aug. 16, 2011", 11 pgs.
"U.S. Appl. No. 12/039,849, Restriction Requirement dated Aug. 16, 2011", 6 pgs.
"U.S. Appl. No. 12/103,824, Examiner Interview Summary dated Jan. 12, 2012", 2 pgs.
"U.S. Appl. No. 12/103,824, Examiner Interview Summary dated Sep. 19, 2011", 3 pgs.
"U.S. Appl. No. 12/103,824, Final Office Action dated Apr. 26, 2012", 19 pgs.
"U.S. Appl. No. 12/103,824, Final Office Action dated Dec. 6, 2011", 20 pgs.
"U.S. Appl. No. 12/103,824, Non Final Office Action dated Aug. 17, 2011", 17 pgs.
"U.S. Appl. No. 12/103,824, Response filed Sep. 15, 2011 to Non Final Office Action dated Aug. 17, 2011", 16 pgs.

(56) References Cited

OTHER PUBLICATIONS

"U.S. Appl. No. 12/103,834, Final Office Action dated Dec. 8, 2010", 11 pgs.
"U.S. Appl. No. 12/103,834, Non Final Office Action dated Jun. 22, 2010", 9 pgs.
"U.S. Appl. No. 12/103,834, Response filed Feb. 3, 2011 to Final Office Action dated Dec. 8, 2010", 5 pgs.
"U.S. Appl. No. 12/103,834, Response filed Sep. 21, 2010 to Non Final Office Action dated Jun. 22, 2010", 11 pgs.
"U.S. Appl. No. 12/103,834, Notice of Allowance dated Feb. 23, 2011", 9 ogs.
"U.S. Appl. No. 12/103,834, Response filed Mar. 18, 2010 to Restriction Requirement dated Feb. 18, 2010", 9 pgs.
"U.S. Appl. No. 12/103,834, Restriction Requirement dated Feb. 18, 2010", 9 pgs.
"U.S. Appl. No. 12/211,407, Examiner Interview Summary dated Jan. 13, 2012", 3 pgs.
"U.S. Appl. No. 12/211,407, Examiner Interview Summary dated Dec. 5, 2013", 3 pgs.
"U.S. Appl. No. 12/211,407, Final Office Action dated Nov. 25, 2011", 14 pgs.
"U.S. Appl. No. 12/211,407, Non Final Office Action dated Aug. 17, 2011", 15 pgs.
"U.S. Appl. No. 12/211,407, Notice of Allowance dated Aug. 7, 2013", 12 pgs.
"U.S. Appl. No. 12/211,407, Response filed Jan. 16, 2012 to Final Office Action dated Nov. 25, 2011", 18 pgs.
"U.S. Appl. No. 12/211,407, Response filed Aug. 29, 2011 to Non Final Office Action dated Aug. 17, 2011", 19 pgs.
"U.S. Appl. No. 12/255,945, Advisory Action dated Feb. 5, 2014", 3 pgs.
"U.S. Appl. No. 12/255,945, Advisory Action dated Feb. 10, 2012", 3 pgs.
"U.S. Appl. No. 12/255,945, Advisory Action dated Mar. 27, 2014", 3 pgs.
"U.S. Appl. No. 12/255,945, Appeal Brief filed Mar. 26, 2014", 29 pgs.
"U.S. Appl. No. 12/255,945, Appeal Brief filed Oct. 13, 2014", 30 pgs.
"U.S. Appl. No. 12/255,945, Examiner Interview Summary dated Aug. 13, 2013", 3 pgs.
"U.S. Appl. No. 12/255,945, Examiner Interview Summary dated Sep. 22, 2011", 3 pgs.
"U.S. Appl. No. 12/255,945, Examiner's Answer dated Feb. 12, 2015", 26 pgs.
"U.S. Appl. No. 12/255,945, Final Office Action dated Sep. 30, 2013", 21 pgs.
"U.S. Appl. No. 12/255,945, Final Office Action dated Nov. 28, 2011", 14 pgs.
"U.S. Appl. No. 12/255,945, Non Final Office Action dated May 7, 2013", 23 pgs.
"U.S. Appl. No. 12/255,945, Non Final Office Action dated Jul. 24, 2014", 26 pgs.
"U.S. Appl. No. 12/255,945, Non Final Office Action dated Aug. 4, 2011", 12 pgs.
"U.S. Appl. No. 12/255,945, Reply Brief filed Apr. 13, 2015", 4 pgs.
"U.S. Appl. No. 12/255,945, Response filed Jan. 17, 2012 to Final Office Action dated Nov. 28, 2011", 11 pgs.
"U.S. Appl. No. 12/255,945, Response filed Jan. 28, 2014 to Final Office Action dated Sep. 30, 2013", 13 pgs.
"U.S. Appl. No. 12/255,945, Response filed Feb. 28, 2012 to Advisory Action dated Feb. 10, 2012", 13 pgs.
"U.S. Appl. No. 12/255,945, Response filed Jul. 7, 2011 to Restriction Requirement dated Jun. 7, 2011", 8 pgs.
"U.S. Appl. No. 12/255,945, Response filed Aug. 8, 2013 to Non Final Office Action dated May 7, 2013", 13 pgs.
"U.S. Appl. No. 12/255,945, Response filed Nov. 4, 2011 to Non Final Office Action dated Aug. 4, 2011", 14 pgs.
"U.S. Appl. No. 12/255,945, Restriction Requirement dated Jun. 7, 2011", 8 pgs.
"U.S. Appl. No. 12/255,945, Supplemental Amendment filed Mar. 5, 2014", 13 pgs.
"U.S. Appl. No. 12/371,096, Examiner Interview Summary dated Jan. 13, 2012", 3 pgs.
"U.S. Appl. No. 12/371,096, Examiner Iinterview Summary dated Dec. 5, 2013", 3 pgs.
"U.S. Appl. No. 12/371,096, Final Office Action dated Jul. 6, 2011", 23 pgs.
"U.S. Appl. No. 12/371,096, Final Office Action dated Nov. 25, 2011", 14 pgs.
"U.S. Appl. No. 12/371,096, Non Final Office Action dated Mar. 30, 2011", 19 pgs.
"U.S. Appl. No. 12/371,096, Non Final Office Action dated Apr. 17, 2014", 23 pgs.
"U.S. Appl. No. 12/371,096, Non Final Office Action dated Aug. 17, 2011", 15 pgs.
"U.S. Appl. No. 12/371,096, Non Final Office Action dated Aug. 28, 2014", 21 pgs.
"U.S. Appl. No. 12/371,096, Notice of Allowance dated Aug. 7, 2013", 12 pgs.
"U.S. Appl. No. 12/371,096, Notice of Allowance dated Nov. 5, 2013", 2 pgs.
"U.S. Appl. No. 12/371,096, Notice of Allowance dated Nov. 15, 2013", 2 pgs.
"U.S. Appl. No. 12/371,096, Response filed Jan. 16, 2012 to Final Office Action dated Nov. 25, 2011", 15 pgs.
"U.S. Appl. No. 12/371,096, Response filed Aug. 29, 2011 to Non Final Office Action dated Aug. 17, 2011", 19 pgs.
"U.S. Appl. No. 12/389,901, Applicant's Summary of Examiner Interview filed Nov. 28, 2011", 1 pg.
"U.S. Appl. No. 12/389,901, Examiner Interview Summary dated Nov. 1, 2011", 3 pgs.
"U.S. Appl. No. 12/389,901, Non Final Office Action dated May 12, 2011", 6 pgs.
"U.S. Appl. No. 12/389,901, Notice of Allowance dated Sep. 30, 2011", 12 pgs.
"U.S. Appl. No. 12/389,901, Notice of Allowance dated Dec. 7, 2011", 9 pgs.
"U.S. Appl. No. 12/389,901, Response filed Mar. 17, 2011 to Restriction Requirement dated Mar. 2, 2011", 8 pgs.
"U.S. Appl. No. 12/389,901, Response filed Jun. 28, 2011 to Non Final Office Action dated May 12, 2011", 11 pgs.
"U.S. Appl. No. 12/389,901, Restriction Requirement dated Mar. 2, 2011", 6 pgs.
"U.S. Appl. No. 12/483,807, Advisory Action dated Jan. 3, 2012", 2 pgs.
"U.S. Appl. No. 12/483,807, Applicant's Summary of Examiner Interview filed Jan. 19, 2012", 3 pgs.
"U.S. Appl. No. 12/483,807, Applicant's Summary of Examiner Interview filed Dec. 21, 2011". 3 pgs.
"U.S. Appl. No. 12/483,807, Non Final Office Action dated Oct. 3, 2011", 18 pgs.
"U.S. Appl. No. 12/483,807, Notice of Allowance dated Feb. 21, 2013", 9 pgs.
"U.S. Appl. No. 12/483,807, Response filed Jan. 16, 2012 to Advisory Action dated Jan. 3, 2012", 14 pgs.
"U.S. Appl. No. 12/483,807, Response filed Oct. 24, 2011 to Non Final Office Action dated Oct. 3, 2011", 16 pgs.
"U.S. Appl. No. 12/483,807, Response filed Dec. 19, 2011 to Final Office Action dated Nov. 4, 2011", 7 pgs.
"U.S. Appl. No. 12/486,992, Examiner Interview Summary dated Jan. 9, 2012", 3 pgs.
"U.S. Appl. No. 12/486,992, Examiner Interview Summary dated Mar. 9, 2012", 4 pgs.
"U.S. Appl. No. 12/486,992, Final Office Action dated Feb. 21, 2012", 8 pgs.
"U.S. Appl. No. 12/486,992, Non Final Office Action dated Nov. 21, 2011", 9 pgs.
"U.S. Appl. No. 12/486,992, Notice of Allowance dated Jun. 12, 2014", 11 pgs.
"U.S. Appl. No. 12/486,992, Preliminary Amendment filed Mar. 9, 2010", 3 pgs.

(56) References Cited

OTHER PUBLICATIONS

"U.S. Appl. No. 12/486,992, Response filed Jan. 17, 2012 to Non Final Office Action dated Nov. 21, 2011", 13 pgs.
"U.S. Appl. No. 12/486,992, Response filed Mar. 12, 2012 to Final Office Action dated Feb. 21, 2012", 10 pgs.
"U.S. Appl. No. 12/486,992, Response filed Oct. 24, 2011 to Restriction Requirement dated Sep. 30, 2011", 7 pgs.
"U.S. Appl. No. 12/486,992, Restriction Requirement dated Sep. 30, 2011", 6 pgs.
"U.S. Appl. No. 12/571,969, Advisory Action dated Oct. 21, 2013", 3 pgs.
"U.S. Appl. No. 12/571,969, Examiner Interview Summary dated Feb. 26, 2015", 3 pgs.
"U.S. Appl. No. 12/571,969, Examiner Interview Summary dated Mar. 11, 2013", 3 pgs.
"U.S. Appl. No. 12/571,969, Final Office Action dated Jan. 15, 2015", 9 pgs.
"U.S. Appl. No. 12/571,969, Final Office Action dated Jul. 31, 2013", 8 pgs.
"U.S. Appl. No. 12/571,969, Non Final Office Action dated Jun. 26, 2014", 8 pgs.
"U.S. Appl. No. 12/571,969, Non Final Office Action dated Dec. 19, 2012", 7 pgs.
"U.S. Appl. No. 12/571,969, Notice of Allowance dated Jun. 23, 2015", 8 pgs.
"U.S. Appl. No. 12/571,969, Preliminary Amendment filed Mar. 16, 2010", 3 pgs.
"U.S. Appl. No. 12/571,969, Response filed Mar. 6, 2013 to Non Final Office Action dated Dec. 19, 2012", 10 pgs.
"U.S. Appl. No. 12/571,969, Response filed May 15, 2015 to Final Office Action dated Jan. 15, 2015", 16 pgs.
"U.S. Appl. No. 12/571,969, Response filed Jun. 4, 2012 to Restriction Requirement dated May 9, 2012", 9 pgs.
"U.S. Appl. No. 12/571,969, Response filed Sep. 26, 2014 to Non Final Office Action dated Jun. 26, 2014", 12 pgs.
"U.S. Appl. No. 12/571,969, Response filed Sep. 30, 2013 to Final Office Action dated Jul. 31, 2013", 13 pgs.
"U.S. Appl. No. 12/571,969, Restriction Requirement dated May 9, 2012", 9 pgs.
"U.S. Appl. No. 12/714,023, Non Final Office Action dated Jan. 26, 2012", 15 pgs.
"U.S. Appl. No. 12/714,023, Notice of Allowance dated Apr. 9, 2012", 10 pgs.
"U.S. Appl. No. 12/714,023, Response filed Jan. 3, 2012 to Restriction Requirement dated Dec. 12, 2011", 9 pgs.
"U.S. Appl. No. 12/714,023, Response filed Feb. 14, 2012 to Non Final Office Action dated Jan. 26, 2012", 15 pgs.
"U.S. Appl. No. 12/714,023, Restriction Requirement dated Dec. 12, 2011", 5 pgs.
"U.S. Appl. No. 12/872,663, Non Final Office Action dated Jun. 20, 2012", 11 pgs.
"U.S. Appl. No. 12/872,663, Notice of Allowance dated Nov. 15, 2012", 9 pgs.
"U.S. Appl. No. 12/872,663, Response filed May 21, 2012 to Restriction Requirement dated Apr. 27, 2012", 7 pgs.
"U.S. Appl. No. 12/872,663, Restriction Requirement dated Apr. 27, 2012", 6 pgs.
"U.S. Appl. No. 12/872,663, Supplemental Amendment filed Nov. 8, 2012", 8 pgs.
"U.S. Appl. No. 12/888,005, Non Final Office Action dated Jun. 1, 2012", 11 pgs.
"U.S. Appl. No. 12/888,005, Notice of Allowance dated Sep. 27, 2012", 6 pgs.
"U.S. Appl. No. 12/888,005, Response filed May 15, 2012 to Restriction Requirement dated Apr. 27, 2012", 7 pgs.
"U.S. Appl. No. 12/888,005, Response filed Jul. 11, 2012 to Non Final Office Action dated Jun. 1, 2012", 12 pgs.
"U.S. Appl. No. 12/888,005, Restriction Requirement dated Apr. 27, 2012", 7 pgs.
"U.S. Appl. No. 12/893,306, Examiner Interview Summary dated Dec. 18, 2014", 3 pgs.
"U.S. Appl. No. 12/893,306, Final Office Action dated Sep. 11, 2014" 8 pgs.
"U.S. Appl. No. 12/893,306, Non Final Office Action dated Feb. 26, 2014", 9 pgs.
"U.S. Appl. No. 12/893,306, Notice of Allowability dated Jul. 29, 2015", 2 pgs.
"U.S. Appl. No. 12/893,306, Notice of Allowance dated Apr. 14, 2015", 5 pgs.
"U.S. Appl. No. 12/893,306, Response filed Jan. 12, 2015 to Final Office Action dated Sep. 11, 2014", 14 pgs.
"U.S. Appl. No. 12/893,306, Response filed May 22, 2014 to Non Final Office Action dated Feb. 26, 2014", 8 pgs.
"U.S. Appl. No. 12/893,306, Response filed Nov. 4, 2013 to Restriction Requirement dated Oct. 4, 2013", 11 pgs.
"U.S. Appl. No. 12/893,306, Restriction Requirement dated Oct. 4, 2013", 11 pgs.
"U.S. Appl. No. 12/938,905, Advisory Action dated Feb. 4, 2013", 3 pgs.
"U.S. Appl. No. 12/938,905, Appeal Brief filed Feb. 28, 2013", 1 pg.
"U.S. Appl. No. 12/938,905, Appeal Brief filed Apr. 29, 2013", 26 pgs.
"U.S. Appl. No. 12/938,905, Appeal Decision dated Dec. 14, 2015", 18 pgs.
"U.S. Appl. No. 12/938,905, Examiner Interview Summary dated Jan. 30, 2013", 3 pgs.
"U.S. Appl. No. 12/938,905, Examiner Interview Summary dated Jul. 13, 2012", 3 pgs.
"U.S. Appl. No. 12/938,905, Examiner's Answer to Appeal Brief dated Jun. 24, 2013", 8 pgs.
"U.S. Appl. No. 12/938,905, Final Office Action dated Nov. 28, 2012", 11 pgs.
"U.S. Appl. No. 12/938,905, Non Final Office Action dated Jun. 4, 2012", 11 pgs.
"U.S. Appl. No. 12/938,905, Reply Brief filed Aug. 26, 2013", 12 pgs.
"U.S. Appl. No. 12/938,905, Response filed Jan. 28, 2013 to Final Office Action dated Nov. 28, 2012", 19 pgs.
"U.S. Appl. No. 12/938,905, Response filed May 14, 2012 to Restriction Requirement dated Apr. 17, 2012", 7 pgs.
"U.S. Appl. No. 12/938,905, Response filed Jul. 19, 2012 to Non Final Office Action dated Jun. 4, 2012", 20 pgs.
"U.S. Appl. No. 12/938,905, Response filed Oct. 8, 2012 to Restriction Requirement dated Sep. 14, 2012", 8 pgs.
"U.S. Appl. No. 12/938,905, Restriction Requirement dated Apr. 17, 2012", 8 pgs.
"U.S. Appl. No. 12/938,905, Restriction Requirement dated Sep. 14, 2012", 6 pgs.
"U.S. Appl. No. 12/938,913, Advisory Action dated Jan. 15, 2015", 3 pgs.
"U.S. Appl. No. 12/938,913, Examiner Interview Summary dated Dec. 18, 2014", 3 pgs.
"U.S. Appl. No. 12/938,913, Final Office Action dated Oct. 1, 2014", 9 pgs.
"U.S. Appl. No. 12/938,913, Non Final Office Action dated Mar. 11, 2014", 10 pgs.
"U.S. Appl. No. 12/938,913, Non Final Office Action dated Apr. 9, 2015", 8 pgs.
"U.S. Appl. No. 12/938,913, Notice of Allowance dated Nov. 12, 2015", 5 pgs.
"U.S. Appl. No. 12/938,913, Response filed Jan. 2, 2015 to Final Office Action dated Oct. 1, 2014", 10 pgs.
"U.S. Appl. No. 12/938,913, Response filed Feb. 2, 2015 to Advisory Action dated Jan. 15, 2015", 14 pgs.
"U.S. Appl. No. 12/938,913, Response filed Jun. 11, 2014 to Non Final Office Action dated Mar. 11, 2014", 9 pgs.
"U.S. Appl. No. 12/938,913, Response filed Jul. 7, 2015 to Non Final Office Action dated Apr. 9, 2015", 11 pgs.
"U.S. Appl. No. 12/938,913, Response filed Nov. 6, 2013 to Restriction Requirement dated Oct. 7, 2013", 1 pg.
"U.S. Appl. No. 12/938,913, Restriction Requirement dated Oct. 7, 2013", 7 pgs.

(56) References Cited

OTHER PUBLICATIONS

"U.S. Appl. No. 12/955,361, Non Final Office Action dated Mar. 27, 2013", 23 pgs.
"U.S. Appl. No. 12/955,361, Response filed Jun. 27, 2013 to Non Final Office Action dated Mar 27, 2013", 12 pgs.
"U.S. Appl. No. 12/955,361, Notice of Allowance dated Jul. 18, 2013", 9 pgs.
"U.S. Appl. No. 12/955,361, Notice of Allowance dated Oct. 1, 2013", 4 pgs.
"U.S. Appl. No. 12/955,361, Notice of Allowance dated Oct. 24, 2013", 4 pgs.
"U.S. Appl. No. 12/955,361, Response filed Jan. 14, 2013 to Restriction Requirement dated Dec. 14, 2012", 13 pgs.
"U.S. Appl. No. 12/955,361, Restriction Requirement dated Dec. 14, 2012", 9 pgs.
"U.S. Appl. No. 12/973,214, Response filed Feb. 21, 2014 to Final Office Action dated Nov. 21, 2013", 16 pgs.
"U.S. Appl. No. 12/973,214, Examiner Interview Summary dated Jan. 24, 2014", 3 pgs.
"U.S. Appl. No. 12/973,214, Final Office Action dated Sep. 9, 2015", 10 pgs.
"U.S. Appl. No. 12/973,214, Final Office Action dated Nov. 21, 2013", 14 pgs.
"U.S. Appl. No. 12/973,214, Non Final Office Action dated Feb. 3, 2015", 14 pgs.
"U.S. Appl. No. 12/973,214, Non Final Office Action dated May 22, 2013", 11 pgs.
"U.S. Appl. No. 12/973,214, Notice of Allowance dated Jan. 11, 2016", 8 pgs.
"U.S. Appl. No. 12/973,214, Response filed Apr. 12, 2013 to Restriction Requirement dated Mar. 13, 2013", 9 pgs.
"U.S. Appl. No. 12/973,214, Response filed Jun. 3, 2015 to Non Final Office Action dated Feb. 3, 2015", 13 pgs.
"U.S. Appl. No. 12/973,214, Response filed Aug. 22, 2013 to Non Final Office Action dated May 22, 2013", 12 pgs.
"U.S. Appl. No. 12/973,214, Response filed Nov. 6, 2015 to Final Office Action dated Sep. 9, 2015", 14 pgs.
"U.S. Appl. No. 12/973,214, Restriction Requirement dated Mar. 13, 2013", 8 pgs.
"U.S. Appl. No. 12/978,069, Advisory Action dated Jun. 12, 2013", 3 pgs.
"U.S. Appl. No. 12/978,069, Examiner Interview Summary dated May 28, 2013", 3 pgs.
"U.S. Appl. No. 12/978,069, Final Office Action dated Mar. 25, 2013", 11 pgs.
"U.S. Appl. No. 12/978,069, Non Final Office Action dated Sep. 11, 2012", 11 pgs.
"U.S. Appl. No. 12/978,069, Notice of Allowance dated Jun. 21, 2013", 13 pgs.
"U.S. Appl. No. 12/978,069, Response filed May 23, 2013 to Final Office Action dated Mar. 25, 2013", 17 pgs.
"U.S. Appl. No. 12/978,069, Response filed Aug. 27, 2012 to Restriction Requirement dated Aug. 10, 2012", 8 pgs.
"U.S. Appl. No. 12/978,069, Response filed Dec. 10, 2012 to Non Final Office Action dated Sep. 11, 2012", 15 pgs.
"U.S. Appl. No. 12/978,069, Restriction Requirement dated Aug. 10, 2012", 11 pgs.
"U.S. Appl. No. 12/978,069, Supplemental Notice of Allowance dated Aug. 9, 2013", 3 pgs.
"U.S. Appl. No. 12/978,069, Supplemental Notice of Allowance dated Sep. 17, 2013", 2 pgs.
"U.S. Appl. No. 13/041,469, Non Final Office Action dated Mar. 22, 2013", 12 pgs.
"U.S. Appl. No. 13/041,469, Notice of Allowance dated Aug. 8, 2013", 6 pgs.
"U.S. Appl. No. 13/041,469, Notice of Allowance dated Oct. 3, 2013", 2 pgs.
"U.S. Appl. No. 13/041,469, Notice of Allowance dated Nov. 19, 2013", 2 pgs.
"U.S. Appl. No. 13/041,469, Response filed Jun. 18, 2013 to Non Final Office Action dated Mar. 22, 2013", 15 pgs.
"U.S. Appl. No. 13/041,469, Response filed Oct. 25, 2012 to Restriction Requirement dated Sep. 25, 2012", 1 pg.
"U.S. Appl. No. 13/041,469, Restriction Requirement dated Sep. 25, 2012", 5 pgs.
"U.S. Appl. No. 13/041,495, Appeal Brief filed Oct. 4, 2013", 39 pgs.
"U.S. Appl. No. 13/041,495, Examiner Interview Summary dated Feb. 20, 2013", 3 pgs.
"U.S. Appl. No. 13/041,495, Examiner Interview Summary dated Aug. 6, 2013", 3 pgs.
"U.S. Appl. No. 13/041,495, Final Office Action dated Jun. 18, 2013", 14 pgs.
"U.S. Appl. No. 13/041,495, Non Final Office Action dated Nov. 2, 2012", 10 pgs.
"U.S. Appl. No. 13/041,495, Non Final Office Action dated Dec. 31, 2013", 11 pgs.
"U.S. Appl. No. 13/041,495, Notice of Allowance dated Jun. 11, 2014", 5 pgs.
"U.S. Appl. No. 13/041,495, Response filed Jan. 31, 2013 to Non Final Office Action dated Nov. 2, 2012", 13 pgs.
"U.S. Appl. No. 13/041,495, Response filed Mar. 31, 2014 to Non Final Office Action dated Dec. 31, 2013", 12 pgs.
"U.S. Appl. No. 13/041,495, Response filed Oct. 8, 2012 to Restriction Requirement dated Sep. 25, 2012", 8 pgs.
"U.S. Appl. No. 13/041,495, Restriction Requirement dated Sep. 25, 2012", 7 pgs.
"U.S. Appl. No. 13/041,495, Supplemental Amendment filed Feb. 20, 2013", 15 pgs.
"U.S. Appl. No. 13/041,665, Examiner Interview Summary dated Apr. 30, 2013", 3 pgs.
"U.S. Appl. No. 13/041,665, Final Office Action dated Mar. 5, 2013", 10 pgs.
"U.S. Appl. No. 13/041,665, Non Final Office Action dated Sep. 27, 2012", 10 pgs.
"U.S. Appl. No. 13/041,665, Notice of Allowance dated May 16, 2013", 7 pgs.
"U.S. Appl. No. 13/041,665, Response filed May 3, 2013 to Final Office Action dated Mar. 5, 2013", 13 pgs.
"U.S. Appl. No. 13/041,665, Response filed Sep. 17, 2012 to Restriction Requirement dated Aug. 20, 2012", 6 pgs.
"U.S. Appl. No. 13/041,665, Response filed Dec. 27, 2012 to Non Final Office Action dated Sep. 27, 2012", 16 pgs.
"U.S. Appl. No. 13/041,665, Restriction Requirement dated Aug. 20, 2012", 9 pgs.
"U.S. Appl. No. 13/041,883, Advisory Action dated May 18, 2016", 3 pgs.
"U.S. Appl. No. 13/041,883, Appeal Brief filed Jul. 25, 2016", 26 pgs.
"U.S. Appl. No. 13/041,883, Examiner Interview Summary dated Oct. 27, 2014", 3 pgs.
"U.S. Appl. No. 13/041,883, Final Office Action dated Jan. 15, 2015", 10 pgs.
"U.S. Appl. No. 13/041,883, Final Office Action dated Feb. 11, 2016", 9 pgs.
"U.S. Appl. No. 13/041,883, Non Final Office Action dated Jun. 26, 2014", 8 pgs.
"U.S. Appl. No. 13/041,883, Non Final Office Action dated Aug. 13, 2015", 10 pgs.
"U.S. Appl. No. 13/041,883, Response filed Feb. 17, 2014 to Restriction Requirement dated Jan. 15, 2014", 3 pgs.
"U.S. Appl. No. 13/041,883, Response filed Apr. 7, 2016 to Final Office Action dated Feb. 11, 2016", 17 pgs.
"U.S. Appl. No. 13/041,883, Response filed May 15, 2015 to Final Office Action dated Jan. 15, 2015", 13 pgs.
"U.S. Appl. No. 13/041,883, Response filed Sep. 26, 2014 to Non Final Office Action Jun. 26, 2014", 12 pgs.
"U.S. Appl. No. 13/041,883, Response filed Nov. 6, 2015 to Non Final Office Action dated Aug. 13, 2015", 16 pgs.
"U.S. Appl. No. 13/041,883, Restriction Requirement dated Jan. 15, 2014", 9 pgs.

(56) References Cited

OTHER PUBLICATIONS

"U.S. Appl. No. 13/045,169, Applicant's Summary of Examiner Interview filed Sep. 21, 2015", 2 pgs.
"U.S. Appl. No. 13/045,169, Examiner Interview Summary dated Sep. 10, 2015", 3 pgs.
"U.S. Appl. No. 13/045,169, Final Office Action dated Dec. 3, 2015", 8 pgs.
"U.S. Appl. No. 13/045,169, Non Final Office Action dated Jun. 4, 2015", 8 pgs.
"U.S. Appl. No. 13/045,169, Non Final Office Action dated Sep. 24, 2014", 9 pgs.
"U.S. Appl. No. 13/045,169, Response filed May 15, 2014 to Restriction Requirement dated Mar. 14, 2014", 10 pgs.
"U.S. Appl. No. 13/045,169, Response filed Aug. 31, 2015 to Non Final Office Action dated Jun. 4, 2015", 14 pgs.
"U.S. Appl. No. 13/045,169, Response filed Dec. 23, 2014 to Non Final Office Action dated Sep. 24, 2014", 10 pgs.
"U.S. Appl. No. 13/045,169, Restriction Requirement dated Mar. 14, 2014", 10 pgs.
"U.S. Appl. No. 13/047,924, Examiner Interview Summary dated Jan. 21, 2015", 3 pgs.
"U.S. Appl. No. 13/047,924, Examiner Interview Summary dated Jan. 25, 2013", 3 pgs.
"U.S. Appl. No. 13/047,924, Examiner Interview Summary dated Sep. 5, 2013", 3 pgs.
"U.S. Appl. No. 13/047,924, Examiner Interview Summary dated Sep. 18, 2012", 3 pgs.
"U.S. Appl. No. 13/047,924, Final Office Action dated Apr. 3, 2015", 16 pgs.
"U.S. Appl. No. 13/047,924, Final Office Action dated Jul. 18, 2013", 14 pgs.
"U.S. Appl. No. 13/047,924, Non Final Office Action dated Sep. 21, 2012", 11 pgs.
"U.S. Appl. No. 13/047,924, Non Final Office Action dated Nov. 3, 2014", 14 pgs.
"U.S. Appl. No. 13/047,924, Response filed Feb. 3, 2015 to Non Final Office Action dated Nov. 3, 2014", 16 pgs.
"U.S. Appl. No. 13/047,924, Response filed May 1, 2013 to Restriction Requirement dated Apr. 1, 2013", 11 pgs.
"U.S. Appl. No. 13/047,924, Response filed Sep. 17, 2012 to Restriction Requirement dated Aug. 20, 2012", 9 pgs.
"U.S. Appl. No. 13/047,924, Response filed Oct. 18, 2013 to Final Office Action dated Jul. 18, 2013", 18 pgs.
"U.S. Appl. No. 13/047,924, Response filed Dec. 20, 2012 to Non Final Office Action dated Sep. 21, 2012", 19 pgs.
"U.S. Appl. No. 13/047,924, Restriction Requirement dated Apr. 1, 2013", 7 pgs.
"U.S. Appl. No. 13/047,924, Restriction Requirement dated Aug. 20, 2012", 8 pgs.
"U.S. Appl. No. 13/081,618, Examiner Interview Summary dated Feb. 5, 2013", 3 pgs.
"U.S. Appl. No. 13/081,618, Examiner Interview Summary dated Aug. 31, 2012".
"U.S. Appl. No. 13/081,618, Final Office Action dated Nov. 19, 2012", 8 pgs.
"U.S. Appl. No. 13/081,618, Non Final Office Action dated Jul. 25, 2012", 7 pgs.
"U.S. Appl. No. 13/081,618, Notice of Allowance dated Feb. 26, 2013", 9 pgs.
"U.S. Appl. No. 13/081,618, Response filed Feb. 15, 2013 to Final Office Action dated Nov. 19, 2012", 12 pgs.
"U.S. Appl. No. 13/081,618, Response filed Aug. 23, 2012 to Non Final Office Action dated Jul. 25, 2012", 10 pgs.
"U.S. Appl. No. 13/081,618, Supplemental Notice of Allowability dated Jun. 21, 2013", 2 pgs.
"U.S. Appl. No. 13/088,787, Final Office Action dated May 20, 2015", 11 pgs.
"U.S. Appl. No. 13/088,787, Non Final Office Action dated Sep. 11, 2014", 8 pgs.
"U.S. Appl. No. 13/088,787, Restriction Requirement dated Mar. 12, 2014", 9 pgs.
"U.S. Appl. No. 13/106,295, Non Final Office Action dated Jan. 24, 2013", 14 pgs.
"U.S. Appl. No. 13/106,295, Notice of Allowance dated Aug. 1, 2013", 9 pgs.
"U.S. Appl. No. 13/106,295, Response filed Apr. 16, 2013 to Non Final Office Action dated Jan. 24, 2013", 10 pgs.
"U.S. Appl. No. 13/106,295, Response filed Dec. 20, 2012 to Restriction Requirement dated Nov. 23, 2012", 1 pg.
"U.S. Appl. No. 13/106,295, Restriction Requirement dated Nov. 23, 2012", 5 pgs.
"U.S. Appl. No. 13/111,007, Non Final Office Action dated Mar. 25, 2013", 10 pgs.
"U.S. Appl. No. 13/111,007, Notice of Allowance dated Aug. 1, 2013", 8 pgs.
"U.S. Appl. No. 13/111,007, Notice of Allowance dated Oct. 4, 2013", 2 pgs.
"U.S. Appl. No. 13/111,007, Notice of Allowance dated Nov. 7, 2013", 2 pgs.
"U.S. Appl. No. 13/111,007, Response filed Jun. 20, 2013 to Non Final Office Action dated Mar. 25, 2013", 12 pgs.
"U.S. Appl. No. 13/111,007, Response filed Nov. 26, 2012 to Restriction Requirement dated Sep. 24, 2012", 13 pgs.
"U.S. Appl. No. 13/111,007, Restriction Requirement dated Sep. 24, 2012", 7 pgs.
"U.S. Appl. No. 13/303,546, Notice of Allowance dated Jun. 29, 2012", 12 pgs.
"U.S. Appl. No. 13/303,546, Notice of Allowance dated Nov. 6, 2012", 10 pgs.
"U.S. Appl. No. 13/303,546, Response filed Jun. 14, 2012 to Restriction Requirement dated May 30, 2012", 7 pgs.
"U.S. Appl. No. 13/303,546, Response filed Aug. 16, 2012 to Non Final Office Action dated Jun. 29, 2012", 11 pgs.
"U.S. Appl. No. 13/303,546, Restriction Requirement dated May 30, 2012", 6 pgs.
"U.S. Appl. No. 13/303,546, Supplemental Notice of Allowance dated Jan. 8, 2013", 4 pgs.
"U.S. Appl. No. 13/303,546, Supplemental Notice of Allowance dated Feb. 13, 2013", 4 pgs.
"U.S. Appl. No. 13/343,957, Non Final Office Action dated Feb. 20, 2014", 14 pgs.
"U.S. Appl. No. 13/343,957, Notice of Allowance dated Jul. 24, 2014", 7 pgs.
"U.S. Appl. No. 13/343,957, Response filed May 20, 2014 to Non Final Office Action dated Feb. 20, 2014", 14 pgs.
"U.S. Appl. No. 13/400,652, Corrected Notice of Allowance dated Feb. 1, 2016", 2 pgs.
"U.S. Appl. No. 13/400,652, Non Final Office Action dated Jun. 17, 2015", 7 pgs.
"U.S. Appl. No. 13/400,652, Notice of Allowance dated Jan. 11, 2016", 7 pgs.
"U.S. Appl. No. 13/400,652, Response filed Jan. 28, 2015 to Restriction Requirement dated Nov. 28, 2014", 17 pgs.
"U.S. Appl. No. 13/400,652, Response filed Apr. 13, 2015 to Restriction Requirement dated Feb. 13, 2015", 16 pgs.
"U.S. Appl. No. 13/400,652, Response filed Aug. 13, 2014 to Restriction Requirement dated Jun. 13, 2014", 19 pgs.
"U.S. Appl. No. 13/400,652, Response filed Sep. 16, 2015 to Non Final Office Action dated Jun. 17, 2015", 12 pgs.
"U.S. Appl. No. 13/400,652, Restriction Requirement dated Feb. 13, 2015", 8 pgs.
"U.S. Appl. No. 13/400,652, Restriction Requirement dated Jun. 13, 2014", 9 pgs.
"U.S. Appl. No. 13/400,652, Restriction Requirement dated Nov. 28, 2014", 7 pgs.
"U.S. Appl. No. 13/527,981, Advisory Action dated Jan. 20, 2016", 3 pgs.
"U.S. Appl. No. 13/527,981, Final Office Action dated Feb. 5, 2015", 22 pgs.
"U.S. Appl. No. 13/527,981, Final Office Action dated Nov. 6, 2015", 13 pgs.

(56) References Cited

OTHER PUBLICATIONS

"U.S. Appl. No. 13/527,981, Non Final Office Action dated Feb. 26, 2015", 10 pgs.
"U.S. Appl. No. 13/527,981, Non Final Office Action dated Jul. 28, 2016", 11 pgs.
"U.S. Appl. No. 13/527,981, Non Final Office Action dated Sep. 15, 2014", 19 pgs.
"U.S. Appl. No. 13/527,981, Response filed Jan. 6, 2016 to Final Office Action dated Nov. 6, 2015", 14 pgs.
"U.S. Appl. No. 13/527,981, Response filed May 27, 2014 to Restriction Requirement dated Mar. 27, 2014", 11 pgs.
"U.S. Appl. No. 13/527,981, Response filed Jul. 27, 2015 to Non-Final Office Action dated Feb. 26, 2015", 25 pgs.
"U.S. Appl. No. 13/527,981, Response Filed Oct. 28, 2016 to Non-Final Office Action dated Jul. 28, 2016", 15 pgs.
"U.S. Appl. No. 13/527,981, Restriction Requirement dated Mar. 27, 2014", 7 pgs.
"U.S. Appl. No. 13/572,895, Non Final Office Action dated Nov. 7, 2013", 5 pgs.
"U.S. Appl. No. 13/572,895, Notice of Allowance dated Apr. 29, 2014", 7 pgs.
"U.S. Appl. No. 13/572,895, Response filed Feb. 7, 2014 to Non Final Office Action dated Nov. 7, 2013", 13 pgs.
"U.S. Appl. No. 13/674,531, Final Office Action dated Apr. 29, 2015", 8 pgs.
"U.S. Appl. No. 13/674,531, Response filed Jul. 29, 2015 to Final Office Action dated Apr. 29, 2015", 12 pgs.
"U.S. Appl. No. 13/674,531, Restriction Requirement dated Sep. 24, 2014", 7 pgs.
"U.S. Appl. No. 13/713,710, Notice of Allowance dated Sep. 15, 2015", 10 pgs.
"U.S. Appl. No. 13/713,710, Response filed Aug. 25, 2015 to Restriction Requirement dated Jul. 2, 2015", 7 pgs.
"U.S. Appl. No. 13/713,710, Restriction Requirement dated Jul. 2, 2015", 6 pgs.
"U.S. Appl. No. 13/744,022, Advisory Action dated Oct. 27, 2014", 3 pgs.
"U.S. Appl. No. 13/744,022, Final Office Action dated Jul. 14, 2014", 9 pgs.
"U.S. Appl. No. 13/744,022, Non Final Office Action dated Jan. 30, 2014", 20 pgs.
"U.S. Appl. No. 13/744,022, Notice of Allowance dated Nov. 28, 2014", 9 pgs.
"U.S. Appl. No. 13/744,022, Response filed Apr. 25, 2014 to Non Final Office Action dated Jan. 30, 2014", 16 pgs.
"U.S. Appl. No. 13/744,022, Response filed Oct. 8, 2014 to Final Office Action dated Jul. 14, 2014", 15 pgs.
"U.S. Appl. No. 13/766,419, Advisory Action dated May 18, 2015", 2 pgs.
"U.S. Appl. No. 13/766,419, Final Office Action dated Jan. 13, 2015" 16 pgs.
"U.S. Appl. No. 13/766,419, Non Final Office Action dated Sep. 5, 2014", 14 pgs.
"U.S. Appl. No. 13/766,419, Response filed May 12, 2015 to Final Office Action dated Jan. 13, 2015". 13 pgs.
"U.S. Appl. No. 13/766,419, Response filed Dec. 5, 2014 to Non Final Office Action dated Sep. 5, 2014", 12 pgs.
"U.S. Appl. No. 13/800,334, Examiner Interview Summary dated Jan. 29, 2015", 4 pgs.
"U.S. Appl. No. 13/800,334, Final Office Action dated Feb. 12, 2015", 11 pgs.
"U.S. Appl. No. 13/800,334, Non Final Office Action dated Sep. 24, 2015", 14 pgs.
"U.S. Appl. No. 13/800,334, Non Final Office Action dated Oct. 22, 2014", 11 pgs.
"U.S. Appl. No. 13/800,334, Non Final Office Action dated Dec. 15, 2016", 26 pgs.
"U.S. Appl. No. 13/800,334, Response filed Jan. 21, 2015 to Non Final Office Action dated Oct. 22, 2014", 12 pgs.
"U.S. Appl. No. 13/800,334, Response filed Jun. 24, 2016 to Final Office Action dated Apr. 7, 2016", 19 pgs.
"U.S. Appl. No. 13/800,334, Response filed Jul. 10, 2015 to Final Office Action dated Feb. 12, 2015", 8 pgs.
"U.S. Appl. No. 13/800,334, Response filed Dec. 16, 2015 to Non Final Office Action dated Sep. 24, 2015", 16 pgs.
"U.S. Appl. No. 13/923,827, Advisory Action dated Oct. 9, 2014", 3 pgs.
"U.S. Appl. No. 13/923,827, Examiner Interview Summary dated Sep. 29, 2014", 3 pgs.
"U.S. Appl. No. 13/923,827, Final Office Action dated Jul. 28, 2014", 11 pgs.
"U.S. Appl. No. 13/923,827, Non Final Office Action dated Apr. 10, 2014", 9 pgs.
"U.S. Appl. No. 13/923,827, Notice of Allowance dated Oct. 29, 2014", 11 pgs.
"U.S. Appl. No. 13/923,827, Response filed Jul. 10, 2014 to Non Final Office Action dated Apr. 10, 2014", 13 pgs.
"U.S. Appl. No. 13/923,827, Response filed Sep. 29, 2014 to Final Office Action dated Jul. 28, 2014" 11 pgs.
"U.S. Appl. No. 13/923,827, Supplemental Notice of Allowance dated Feb. 11, 2015", 2 pgs.
"U.S. Appl. No. 13/923,827, Supplemental Notice of Allowance dated Dec. 19, 2014", 3 pgs.
"U.S. Appl. No. 14/027,340, Advisory Action dated Sep. 17, 2015", 3 pgs.
"U.S. Appl. No. 14/027,340, Final Office Action dated Jul. 8, 2015", 10 pgs.
"U.S. Appl. No. 14/027,340, Non Final Office Action dated Jan. 22, 2015", 11 pgs.
"U.S. Appl. No. 14/027,340, Non Final Office Action dated Dec. 9, 2015", 10 pgs.
"U.S. Appl. No. 14/027,340, Notice of Allowance dated May 12, 2016", 7 pgs.
"U.S. Appl. No. 14/027,340, Response filed Feb. 19, 2016 to Non Final Office Action dated Dec. 9, 2015", 13 pgs.
"U.S. Appl. No. 14/027,340, Response filed May 21, 2015 to Non Final Office Action dated Jan. 22, 2015", 14 pgs.
"U.S. Appl. No. 14/027,340, Response filed Sep. 9, 2015 to Final Office Action dated Jul. 8, 2015", 15 pgs.
"U.S. Appl. No. 14/064,970, Advisory Action dated Jan. 4, 2016", 3 pgs.
"U.S. Appl. No. 14/064,970, Final Office Action dated Oct. 19, 2015", 10 pgs.
"U.S. Appl. No. 14/064,970, Non Final Office Action dated Mar. 12, 2015", 11 pgs.
"U.S. Appl. No. 14/064,970, Non Final Office Action dated Jul. 26, 2016", 12 pgs.
"U.S. Appl. No. 14/064,970, Response filed Jul. 8, 2015 to Non Final Office Action dated Mar. 12, 2015", 8 pgs.
"U.S. Appl. No. 14/064,970, Response filed Oct. 26, 2016 to Non Final Office Action dated Jul. 26, 2016", 14 pgs.
"U.S. Appl. No. 14/064,970, Response filed Dec. 9, 2014 to Restriction Requirement dated Oct. 9, 2014", 11 pgs.
"U.S. Appl. No. 14/064,970, Response filed Dec. 15, 2015 to Final Office Action dated Oct. 19, 2015", 11 pgs.
"U.S. Appl. No. 14/064,970, Restriction Requirement dated Oct. 9, 2014", 9 pgs.
"U.S. Appl. No. 14/086,447, Notice of Allowance dated Aug. 12, 2016", 9 pgs.
"U.S. Appl. No. 14/086,447, Preliminary Amendment filed Jul. 29, 2016", 4 pgs.
"U.S. Appl. No. 14/086,447, Response filed May 4, 2016 to Restriction Requirement dated Apr. 6, 2016", 7 pgs.
"U.S. Appl. No. 14/086,447, Restriction Requirement dated Apr. 6, 2016", 7 pgs.
"U.S. Appl. No. 14/100,134 Response Filed Apr. 14, 2016 to Restriction Requirement dated Feb. 24, 2016", 7 pgs.
"U.S. Appl. No. 14/100,134, Notice of Allowance dated Jun. 16, 2016", 14 pgs.
"U.S. Appl. No. 14/100,134, Restriction Requirement dated Feb. 24, 2016", 5 pgs.

(56) References Cited

OTHER PUBLICATIONS

"U.S. Appl. No. 14/105,669, Non Final Office Action dated Jan. 11, 2016", 11 pgs.
"U.S. Appl. No. 14/105,669, Non Final Office Action dated Aug. 11, 2016", 5 pgs.
"U.S. Appl. No. 14/105,669, Response filed Oct. 13, 2015 to Restriction Requirement dated Sep. 8, 2015", 7 pgs.
"U.S. Appl. No. 14/105,669, Response filed Oct. 31, 2016 to Non Final Office Action dated Aug. 11, 2016", 8 pgs.
"U.S. Appl. No. 14/105,669, Restriction Requirement dated Sep. 8, 2015", 6 pgs.
"U.S. Appl. No. 14/106,669, Response filed Apr. 11, 2016 to Non Final Office Action dated Jan. 11, 2016", 11 pgs.
"U.S. Appl. No. 14/107,316, Corrected Notice of Allowance dated Jul. 11, 2016", 2 pgs.
"U.S. Appl. No. 14/107,316, Examiner Interview Summary dated Jun. 10, 2016", 3 pgs.
"U.S. Appl. No. 14/107,316, Non Final Office Action dated Mar. 24, 2016", 16 pgs.
"U.S. Appl. No. 14/107,316, Notice of Allowance dated Jun. 28, 2016", 11 pgs.
"U.S. Appl. No. 14/107,316, Notice of Non-Compliant Amendment dated Dec. 30, 2015", 3 pgs.
"U.S. Appl. No. 14/107,316, Response filed Jan. 18. 2016 to Notice of Non-Compliant Amendment dated Dec. 30, 2015", 8 pgs.
"U.S. Appl. No. 14/107,316, Response filed Jun. 13, 2016 to Non Final Office Action dated Mar. 24, 2016", 13 pgs.
"U.S. Appl. No. 14/107,316, Response filed Dec. 16, 2015 to Restriction Requirement dated Oct. 29, 2015", 8 pgs.
"U.S. Appl. No. 14/107,316, Restriction Requirement dated Oct. 29, 2015", 8 pgs.
"U.S. Appl. No. 14/159,071, Final Office Action dated May 14, 2015", 7 pgs.
"U.S. Appl. No. 14/159,071, Non Final Office Action dated Dec. 8, 2014", 14 pgs.
"U.S. Appl. No. 14/483,214, Final Office Action dated Dec. 16, 2015", 9 pgs.
"U.S. Appl. No. 14/483,214, Non Final Office Action dated Jun. 5, 2015", 8 pgs.
"U.S. Appl. No. 14/483,214, Non Final Office Action dated Oct. 6, 2016", 12 pgs.
"U.S. Appl. No. 14/483,214, Response filed Jan. 6, 2017 to Non Final Office Action dated Oct. 6, 2016", 16 pgs.
"U.S. Appl. No. 14/483,214, Response filed Mar. 14, 2016 to Final Office Action dated Dec. 16, 2015", 15 pgs.
"U.S. Appl. No. 14/483,214, Response filed May 15, 2015 to Restriction Requirement dated Mar. 25, 2015", 2 pgs.
"U.S. Appl. No. 14/483,214, Response filed Sep. 2, 2015 to Non Final Office Action dated Jun. 5, 2015", 13 pgs.
"U.S. Appl. No. 14/483,214, Restriction Requirement dated Mar. 25, 2015", 6 pgs.
"U.S. Appl. No. 14/658,429, Final Office Action dated Aug. 29, 2016", 9 pgs.
"U.S. Appl. No. 14/658,429, Non Final Office Action dated Mar. 24, 2016", 7 pgs.
"U.S. Appl. No. 14/658,429, Response filed Nov. 21, 2016 to Final Office Action dated Aug. 29, 2016", 14 pgs.
"U.S. Appl. No. 14/658,429, Response Filed Jun. 20, 2016 to Non-Final Office Action dated Mar. 24, 2016", 12 pgs.
"U.S. Appl. No. 14/684,936, Corrected Notice of Allowance dated Sep. 22, 2016", 4 pgs.
"U.S. Appl. No. 14/684,936, Non Final Office Action dated Mar. 22, 2016", 7 pgs.
"U.S. Appl. No. 14/684,936, Notice of Allowance dated Aug. 30, 2016", 6 pgs.
"U.S. Appl. No. 14/684,936, Response filed Jun. 9, 2016 to Non Final Office Action dated Mar. 22, 2016", 8 pgs.
"U.S. Appl. No. 14/798,809, Preliminary Amendment filed Oct. 29, 2015", 7 pgs.
"U.S. Appl. No. 14/798,809, Restriction Requirement dated Jan. 4, 2017", 10 pgs.
"U.S. Appl. No. 14/812,583, Preliminary Amendment filed Jul. 29, 2015", 6 pgs.
"U.S. Appl. No. 14/865,762, Preliminary Amendment filed Oct. 14, 2015", 6 pgs.
"U.S. Appl. No. 14/973,057, Non Final Office Action dated Oct. 18, 2016", 6 pgs.
"U.S. Appl. No. 14/973,057, Preliminary Amendment filed Dec. 18, 2015", 7 pgs.
"U.S. Appl. No. 14/973,057, Response filed Sep. 21, 2016 to Restriction Requirement dated Jul. 29, 2016", 5 pgs.
"U.S. Appl. No. 14/973,057, Restriction Requirement dated Jul. 29, 2016", 8 pgs.
"U.S. Appl. No. 15/008,528, Preliminary Amendment dated Jan. 29, 2016", 8 pgs.
"U.S. Appl. No. 15/093,384, Preliminary Amendment filed Apr. 28, 2016", 5 pgs.
"U.S. Appl. No. 15/224,741, Preliminary Amendment filed Sep. 12, 2016", 8 pgs.
"U.S. Appl. No. 15/267,714, Preliminary Amendment filed Oct. 6, 2016", 7 pgs.
"U.S. Appl. No. 15/267,714, Restriction Requirement dated Jan. 5, 2017", 5 pgs.
"U.S. Appl. No. 12/025,414, Applicant's Summary of Examiner Interview filed Apr. 9, 2012", 4 pgs.
"U.S. Appl. No. 12/025,414, Final Office Action dated Mar. 14, 2012", 6 pgs.
"U.S. Appl. No. 12/025,414, Final Office Action dated May 1, 2012", 10 pgs.
"U.S. Appl. No. 12/025,414, Non Final Office Action dated Oct. 25, 2011", 10 pgs.
"U.S. Appl. No. 12/025,414, Notice of Allowance dated Jun. 13, 2012", 7 pgs.
"U.S. Appl. No. 12/025,414, Response filed Apr. 9, 2012 to Final Office Action dated Mar. 14, 2012", 15 pgs.
"U.S. Appl. No. 12/025,414, Response filed May 21, 2012 to Final Office Action dated May 1, 2012", 6 pgs.
"U.S. Appl. No. 12/025,414, Response filed Jul. 26, 2011 to Restriction Requirement dated Jul. 19, 2011", 8 pgs.
"U.S. Appl. No. 12/025,414, Response filed Dec. 22, 2011 to Non Final Office Action dated Oct. 25, 2011", 13 pgs.
"U.S. Appl. No. 12/025,414, Restriction Requirement dated Jul. 19, 2011", 5 pgs.
"U.S. Appl. No. 12/483,807, Final Office Action dated Nov. 4, 2011", 20 pgs.
"U.S. Appl. No. 12/872,663, Response filed Sep. 13, 2012 to Non Final Office Action dated Jun. 20, 2012", 9 pgs.
"U.S. Appl. No. 13/800,334, Final Office Action dated Apr. 6, 2016", 19 pgs.
"Australian Application Serial No. 2013222609, Response filed Sep. 17, 2015 to First Examiner Report dated Feb. 16, 2015", 17 pgs.
"DURALOC® Cementless Acetabular Reconstruction", Surgical Technique brochure, DePuy International Ltd., (2007), 10 pgs.
"European Application Serial 13710642.3, Communication Pursuant to Article 94(3) EPC dated Nov. 6, 2015", 3 pgs.
"European Application Serial 13710642.3, Intention to grant dated Jun. 17, 2016", 7 pgs.
"European Application Serial 13710642.3, Response filed Mar. 16, 2016 to Communication Pursuant to Article 94(3) EPC dated Nov. 6, 2015", 8 pgs.
"European Application Serial No. 07809326.7, Office Action dated Jan. 28, 2009", 2 pgs.
"European Application Serial No. 07809326.7, Office Action dated Dec. 2, 2011", 1 pg.
"European Application Serial No. 07809326.7, Response filed Jun. 6, 2012 to Extended European Search Report dated Nov. 15, 2011", 6 pgs.
"European Application Serial No. 07809326.7, Response filed Jul. 31, 2015 to Examination Notification Art. 94(3) dated Jan. 22, 2015", 10 pgs.

(56) References Cited

OTHER PUBLICATIONS

"European Application Serial No. 09731923.0, Communication Pursuant to Article 94(3) EPC dated Nov. 29, 2016", 5 pgs.
"European Application Serial No. 09731923.0, Office Action dated Feb. 3, 2011", 2 pgs.
"European Application Serial No. 09731923.0, Response filed Aug. 20, 2015 to Examination Notification Art. 94(3) dated Feb. 10, 2015", 11 pgs.
"European Application Serial No. 09732174.9, Communication Pursuant to Article 94(3) EPC dated Mar. 3, 2016", 4 pgs.
"European Application Serial No. 09732174.9, Communication Pursuant to Article 94(3) EPC dated Oct. 17, 2016", 4 pgs.
"European Application Serial No. 09732174.9, Examination Notification Art. 94(3) dated Mar. 7, 2014", 5 pgs.
"European Application Serial No. 09732174.9, Office Action dated Feb. 3, 2011", 2 pgs.
"European Application Serial No. 09732174.9, Response filed Jul. 13, 2016 to Communication Pursuant to Article 94(3) EPC dated Mar. 3, 2016", 12 pgs.
"European Application Serial No. 09732174.9, Response filed Jul. 14, 2014 to Examination Notification Art. 94(3) dated Mar. 7, 2014", 6 pgs.
"European Application Serial No. 09792468.2, Communication Pursuant to Article 94(3) EPC dated Jun. 7, 2016", 4 pgs.
"European Application Serial No. 09792468.2, Examination Notification Art. 94(3) dated Jan. 29, 2015", 5 pgs.
"European Application Serial No. 09792468.2, Office Action dated Jul. 8, 2011", 2 pgs.
"European Application Serial No. 09792468.2, Response filed Jan. 9, 2012 to Office Action dated Jul. 8, 2011", 11 pgs.
"European Application Serial No. 09792468.2, Response filed May 29, 2015 to Examination Notification Art. 94(3) dated Jan. 29, 2015", 8 pgs.
"European Application Serial No. 09792468.2, Response filed Sep. 28, 2016 to Communication Pursuant to Article 94(3) EPC dated Jun. 7, 2016", 21 pgs.
"European Application Serial No. 10705064.3, Communication Pursuant to Article 94(3) dated Dec. 8, 2015", 4 pgs.
"European Application Serial No. 10705064.3, Office Action dated Nov. 22, 2011", 2 pgs.
"European Application Serial No. 10705064.3, Response filed Apr. 18, 2016 to Communication Pursuant to Article 94(3) EPC dated Dec. 8, 2015", 8 pgs.
"European Application Serial No. 10705064.3, Response filed Aug. 14, 2015 to Examination Notification Art. 94(3) dated Feb. 4, 2015", 9 pgs.
"European Application Serial No. 10705951.1, Communication Pursuant to Article 94(3) EPC dated Jan. 22, 2013", 7 pgs.
"European Application Serial No. 10705951.1, Office Action dated Oct. 7, 2011", 2 pgs.
"European Application Serial No. 10705951.1, Response filed May 23, 2013 to Communication Pursuant to Article 94(3) EPC dated Jan. 22, 2013", 8 pgs.
"European Application Serial No. 12156937.0, Decision of Grant dated May 4, 2015", 2 pgs.
"European Application Serial No. 12156937.0, Examination Notification Art. 94(3) dated Dec. 11, 2013", 5 pgs.
"European Application Serial No. 12156937.0, Extended European Search Report dated Sep. 6, 2012", 9 pgs.
"European Application Serial No. 12156937.0, Response filed Apr. 16, 2013 to Extended European Search Report dated Sep. 6, 2012", 9 pgs.
"European Application Serial No. 12156937.0, Response filed Apr. 17, 2014 to Examination Notification Art. 94(3) dated Dec. 11, 2013", 15 pgs.
"European Application Serial No. 12724475.4, Communication Pursuant to Article 94(3) EPC dated Aug. 31, 2016", 5 pgs.
"European Application Serial No. 12724475.4, Office Action dated Jan. 21, 2014", 2 pgs.
"European Application Serial No. 12724475.4, Response filed Apr. 15, 2015 to Examination Notification Art. 94(3) dated Nov. 24, 2014", 9 pgs.
"European Application Serial No. 13710642.3, Amendment dated Sep. 1, 2014", 7 pgs.
"European Application Serial No. 13710642.3, Office Action dated Oct. 10, 2014", 2 pgs.
"Hand Instruments", High Performance, Precision Series brochure by Arthrotek, copyright, (2000), 3 pgs.
"International Application Serial No. PCT/GB2007/003737, International on Preliminary Report on Patentability dated Apr. 7, 209", 8 pgs.
"International Application Serial No. PCT/GB2007/003737, Written Opinion dated Jan. 25, 2008", 7 pgs.
"International Application Serial No. PCT/US2009/061434, International Preliminary Report on Patentability dated May 5, 2011", 6 pgs.
"International Application Serial No. PCT/US2009/061434, International Search Report dated Feb. 2, 2010", 4 pgs.
"International Application Serial No. PCT/US2009/061434, Written Opinion dated Feb. 2, 2010", 4 pgs.
"International Application Serial No. PCT/US2011/026412, International Preliminary Report on Patentability dated Sep. 30, 2012", 8 pgs.
"International Application Serial No. PCT/US2011/057300 , International Preliminary Report on Patentability dated May 16, 2013", 11 pgs.
"International Application Seriai No. PCT/US2011/057300, Written Opinion dated Mar. 5, 2012", 9 pgs.
"International Application Serial No. PCT/US2012/038351 , International Search Report dated Jul. 6, 2012", 6 pgs.
"International Application Serial No. PCT/US2012/038351, Written Opinion dated Jul. 6, 2012", 8 pgs.
"International Application Serial No. PCT/US2013/074288, International Preliminary Report on Patentability dated Jun. 25, 2015", 13 pgs.
"International Application Serial No. PCT/US2014/068131, International Search Report dated May 8, 2015", 5 pgs.
"International Application Serial No. PCT/US2014/068131, Written Opinion dated May 8, 2015", 9 pgs.
"International Application Serial No. PCT/US2015/039561 , International Search Report dated Sep. 14, 2015", 5 pgs.
"International Application Serial No. PCT/US2015/039561, Written Opinion dated Sep. 14, 2015", 6 pgs.
"Japanese Application Serial No. 2011-505080, Appeal Decision dated Jun. 24, 2015", (W/ English Translation), 3 pgs.
"Japanese Application Serial No. 2011-505080, Decision of Refusal dated Nov. 27, 2013", (W/ English Translation), 4 pgs.
"Japanese Application Serial No. 2011-505080, Office Action dated Feb. 25, 2015", (W/ English Translation), 2 pgs.
"Japanese Application Serial No. 2011-505080, Office Action dated Apr. 3, 2013", (W/ English Translation), 6 pgs.
"Japanese Application Serial No. 2011-505080, Response filed Mar. 27, 2014 to Decision of Refusal dated Nov. 27, 2013", (W/ English Translation), 12 pgs.
"Japanese Application Serial No. 2011-505080, Response filed May 25, 2015 to Office Action dated Feb. 25, 2015", No English Translation, 6 pgs.
"Japanese Application Serial No. 2011-505080, Response filed Jul. 3, 2013 to Office Action dated Apr. 3, 2013", (W/ English Translation), 11 pgs.
"Japanese Application Serial No. 2011-527885, Office Action dated Aug. 27, 2013", (English Translation), 8 pgs.
"Japanese Application Serial No. 2011-527885, Response filed Nov. 26, 2013 to Office Action mailed Aug. 27, 2013", (W/ English Translation of Claims), 9 pgs.
"Japanese Application Serial No. 2013-537691, Office Action dated Feb. 10, 2015", No English Translation, 3 pgs.
"Japanese Application Serial No. 2013-537691, Office Action dated Apr. 15, 2014", (W/ English Translation), 2 pgs.
"Japanese Application Serial No. 2013-537691, Office Action dated Aug. 19, 2014", (W/ English Translation), 4 pgs.

(56) References Cited

OTHER PUBLICATIONS

"Japanese Application Serial No. 2013-537691, Response filed Jul. 5, 2014 to Office Action dated Apr. 15, 2014", No English Translation, 7 pgs.
"Japanese Application Serial No. 2013-537691, Response filed Dec. 19, 2014 to Office Action dated Aug. 19, 2014", No English Translation, 8 pgs.
"Japanese Application Serial No. 2014-257600, Examiners Decision of Final Refusal dated Dec. 20, 2016", (W/ English Translation), 2 pgs.
"Japanese Application Serial No. 2014-257600, Office Action dated May 24, 2016", (W/ English Translation), 5 pgs.
"Japanese Application Serial No. 2014-257600, Office Action dated Oct. 27, 2015", (W/ English Translation), 6 pgs.
"Japanese Application Serial No. 2014-257600, Response filed Jan. 20, 2016 to Office Action dated Oct. 27, 2015", (W/ English Translation of Claims), 5 pgs.
"Japanese Application Serial No. 2014-257600, Voluntary Amendment filed Dec. 19, 2014", No English Translation, 16 pgs.
"Japanese Application Serial No. 2014-511538, Office Action dated Apr. 7, 2015", (W/ English Translation), 5 pgs.
"Japanese Application Serial No. 2014-511538, Office Action dated Nov. 17, 2015", W/ English Translation, 5 pgs.
"Japanese Application Serial No. 2014-511538, Response filed Feb. 17, 2016 to Office Action dated Nov. 17, 2015", (W/ English Translation of Claims), 9 pgs.
"Japanese Application Serial No. 2014-511538, Response filed Jul. 6, 2015 to Office Action dated Apr. 7, 2015", No English Translation, 6 pgs.
"Japanese Application Serial No. 2014-558800, Office Action dated Sep. 1, 2015", (W/ English Translation), 8 pgs.
"Japanese Application Serial No. 2014-558800, Response filed Dec. 1, 2015 to Office Action dated Sep. 1, 2015", (W/ English Translation), 9 pgs.
"Insall/Burstein II Modular Knee System", Zimmer, Inc., (1989), 20 pgs.
"Magnum™, M2a-Magnum™ Operative Technique", brochure. Biomet UK Ltd., (2008), 14 pgs.
"MAX-Ti™ Modular Protrusio Cage", Surgical Technique brochure. Biomet Orthopedics, Inc., (2003), 10 pgs.
"MAX-Ti™ Modular Protrusio Cage", Surgical Technique brochure. Biomet Orthopedics, Inc., (2006), 12 pgs.
"Minimally Invasive Solution Technique—Instrumentation", The M/G Unicompartmental Knee, (2001), 4 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Nex Gen Complete Knee Solution-Intramedually Instrumentation Surgical Technique", NexGen Cruciate Reatining & Legacy Posterior Stablized Knee, (1994), 37 pgs.
"Nexgen Complete Knee Solution", Extramedullary/intramedullary Tibial Resector: Surgical Technique, Zimmer, Inc. 97-5997-02 Rev 1, (2000), 26 pgs.
"NexGen Complete Knee Solution-Multi-Reference 4-in-1 Femoral Instrumentation-Anterior Reference Surgical Technique", (Aug. 1, 2001), 17 pgs.
"NexGen System Complete Knee Solution—Design Rationale", 26 pgs.
"Orthopaedic Salvage System Femoral/Tibial Augmentation", Biomet Orthopedics, Inc., Product Brochure, (2003, 2004), 12 pgs.
"PAR 5™ Protrusio Acetabular Reconstruction System", Biomet Orthopedics, Inc., (2006), 12 pgs.
"Proximal Tibial Replacement (MOST)", Zimmer MOST Options System Surgical Technique, (2005), 84 pgs.
"Scorpio Single Axis Total Knee System—Passport Total Knee Instruments", Suri:iical TechniQue by Srvker Howmedica Osteonics, (2000), 54 pgs.
"Simple Instruments Surgical Technique for the Knee", Biomet, Inc., (2000), 4 pgs.
"Surgical Navigation for Total Knee Arthroplasty—Belived to have been presented at the American Academy of Orthopedic Surgeons", (Feb. 2001), 24 pgs.
"Surgical Technique for the Maxim®, Ascent™ and Vanguard™ Total Knee Systems", Microplast™ minimally invasive knee instruments brochure, (Feb. 29, 2004), 15 pgs.
"Surgical Technique—Nexgen Complete Knee Solution for the Legacy Knee LPS-Flex Fixed Bearing Knee", Zimmer, Inc., (2004, 2007), 12 pgs.
"Taperloc Complete Hip System Surgical Technique", Biomet: Brochure 2012 REV061512, (2011), 12 pgS.
"The AGC Revision Knee System Surgical Technique", Biomet, Inc., (1997), 14 pgs.
"The Fudger™—The Ultimate Weapon in the Femoral Referencing War", Biomet, Inc., 2 pgs.
"United Kingdom Application Serial No. 0619534.1, Search Report dated Dec. 18, 2006", (dated Dec. 8, 2006), 1 pg.
"United Kingdom Application Serial No. 1116054.6, Office Action dated Aug. 12, 2016", 2 pgs.
"United Kingdom Application Serial No. 1116054.6, Response filed Oct. 11, 2016 to Office Action dated Aug. 12, 2016", 12 pgs.
"United Kingdom Application Serial No. 11160546, First Examination Report dated Jun. 6, 2016", 4 pgs.
"United Kingdom Application Serial No. 1207103.1, Amendment filed Apr. 13, 2012", 9 pgs.
"United Kingdom Application Serial No. 1207103.1, Office Action dated May 14, 2015", 3 pgs.
"United Kingdom Application Serial No. 1207103.1, Office Action dated Oct. 6, 2015", 2 pgs.
"United Kingdom Application Serial No. 1207103.1, Response filed Sep. 14, 2015 to Office Action dated May 14, 2015", 22 pgs.
"United Kingdom Application Serial No. 1216577.5, Office Action dated Oct. 20, 2016", 4 pgs.
"United Kingdom Application Serial No. 1216577.5, Office Action dated Oct. 29, 2015", 4 pgs.
"United Kingdom Application Serial No. 1216577.5, Response filed Feb. 24, 216 to Office Action dated Oct. 29, 2015", 27 pgs.
"United Kingdom Application Serial No. 1216577.5, Response filed Oct. 25, 2016 to Office Action dated Oct. 20, 2016", 24 pgs.
"United Kingdom Application Serial No. 1308746.5, Office Action dated Oct. 14, 2016", 5 pgs.
"United Kingdom Application Serial No. 1516672.1, Combined Search and Examination Report dated Oct. 22, 2015", 5 pgs.
"United Kingdom Application Serial No. 1516672.1, Office Action dated Mar. 7, 2016", 3 pgs.
"United Kingdom Application Serial No. 1516672.1, Response filed Feb. 22, 2016 to Combined Search and Examination Report dated Oct. 22, 2015", (English Translation of Claims), 37 pgs.
"United Kingdom Application Serial No. 1516672.1, Response filed Apr. 13, 2016 to Office Action dated Mar. 7, 2016", 13 pgs.
"Zimmer MIS Multi-Reference 4-in-1 Femoral Instrumentation Surgical Technique", Zimmer, Inc., (2003, 2008, 2009), 48 pgs.
Biomet, "The Oxford® Partial Knee System Surgical Technique", Biomet: Manual of the Surgical Technique, (Feb. 2010), 44 pgs.
Clohisy, John C, et al., "Periacetabular Osteotomy in the Treatment of Severe Acetabular Dysplasia", The Journal of Bone & Joint Surgery, vol. 87-A • No. 2, (2005), 7 pgs.
Hitt, Kirby, et al., "Anthropometric Measurements of the Human Knee: Correlation to the Sizing of Current Knee Arthroplasty Systems", The Journal of Bone & Joint Surgery, (2003), 114-122.
Keys, Graham W., "Reduced Invasive Approach for Oxford II Medial Unicompartmental Knee Replacement—a Preliminary Study", The Knee, (1999), 193-196.
Masatoshi, Naito, et al., "Curved Periacetabular Osteotomy for Treatment of Dysplastic Hip", Clinical Orthopaedics and Related Research, (Apr. 2005), 129-135.
Miller, et al., "Unicompartmental Knee System", The Miller/Galante Advantage; Zimmer, 11 pgs.
Miller, Nancy H, et al., "Long-term Results of the Dial Osteotomy in the Treatment of High-grade Acetabular Dysplasia", Clinical Orthopaedics and Related Research, (2005), 115-123.

(56) References Cited

OTHER PUBLICATIONS

Yasunaga, Yuji, et al., "Rotational Acetabular Osteotomy for Advanced Osteoarthritis Secondary to Dysplasia of the Hip. Surgical Technique", The Journal of Bone & Joint Surgery, (2007), 11 pgs.

"U.S. Appl. No. 12/371,096, Appeal Decision dated Jun. 23, 17", 10 pgs.

"U.S. Appl. No. 13/527,981, Response filed Sep. 21, 2017 to Non Final Office Action dated Jun. 22, 2017", 11 pgs.

"U.S. Appl. No. 13/800,334, Notice of Allowance dated Aug. 31, 2017", 8 pgs.

"U.S. Appl. No. 14/327,234, Notice of Allowance dated Jun. 22, 2017", 12 pgs.

"U.S. Appl. No. 14/483,214, Response filed Jul. 31, 2017 to Non Final Office Action dated May 2, 2017", 12 pgs.

"U.S. Appl. No. 14/658,429, Advisory Action dated Sep. 12, 2017", 3 pgs.

"U.S. Appl. No. 14/658,429, Examiner Interview Summary dated Aug. 17, 2017", 2 pgs.

"U.S. Appl. No. 14/658,429, Response filed Aug. 11, 2017 to Final Office Action dated Jun. 15, 2017", 21 pgs.

"U.S. Appl. No. 14/658,429, Supplemental Response Filed Sep. 21, 2017 to Final Office Action dated Jun. 15, 2017 and Advisory Action dated Sep. 12, 2017", 25 pgs.

"U.S. Appl. No. 14/798,809, Examiner Interview Summary dated Sep. 14, 2017", 3 pgs.

"U.S. Appl. No. 14/798,809, Non Final Office Action dated Jun. 28, 2017", 7 pgs.

"U.S. Appl. No. 14/798,809, Response filed Sep. 26, 2017 to Non Final Office Action dated Jun. 28, 2017", 9 pgs.

"U.S. Appl. No. 14/865,762, Response filed Sep. 13, 2017 to Non Final Office Action dated Jun. 13, 2017", 17 pgs.

"U.S. Appl. No. 15/130,414, Restriction Requirement dated Sep. 20, 2017", 7 pgs.

"U.S. Appl. No. 15/267,714, Response filed Aug. 4, 2017 to Non Final Office Action dated May 10, 2017", 21 pgs.

"U.S. Appl. No. 15/618,331, Preliminary Amendment filed Jun. 28, 2017", 6 pgs.

"U.S. Appl. No. 15/650,035, Preliminary Amendment filed Jul. 20, 2017", 6 pgs.

"U.S. Appl. No. 15/672,724, Preliminary Amendment Filed Aug. 9, 2017", 4 pgs.

"U.S. Appl. No. 15/672,724, Supplemental Preliminary Amendment filed Aug. 23, 2017", 7 pgs.

"U.S. Appl. No. 13/800,334, Response filed Aug. 10, 2017 to Final Office Action dated Jun. 15, 2017", 9 pgs.

"European Application Serial No. 15739458.6, Response filed Sep. 4, 2017 to Communication pursuant to Rules 161(1) and 162 EPC dated Feb. 21, 2017", 9 pgs.

"European Application Serial No. 16179569.5, Extended European Search Report dated Jul. 7, 2017", 8 pgs.

"U.S. Appl. No. 15/130,414, Non Final Office Action dated Jul. 27, 2018", 7 pgs.

* cited by examiner

METHOD AND APPARATUS FOR MANUFACTURING AN IMPLANT

CROSS-REFERENCE TO RELATED APPLICATIONS

This application is a continuation of U.S. application Ser. No. 13/766,419 filed on Feb. 13, 2013, which is a divisional of U.S. application Ser. No. 12/872,663 filed on Aug. 31, 2012, now U.S. Pat. No. 8,407,067 issued on Mar. 26, 2013, which claims the benefit of U.S. Provisional Application No. 61/310,752 filed on Mar. 5, 2010.

The disclosures of all the above applications are incorporated herein by reference.

INTRODUCTION

The present teachings provide an implant customized for a specific patient based on a plurality of parameters identified during a preoperative planning stage.

SUMMARY

The present teachings provide an orthopedic device that includes a femoral implant having a non-custom internal bone engagement surface. The femoral implant further includes at least nine parameters adjusted preoperatively to correspond to a specific patient. In one embodiment, the femoral implant includes three patient-specific lengths, three patient specific medial angles and three patient specific lateral angles, wherein the lengths and medial and lateral angles are selected preoperatively based on a three-dimensional image of an anatomy of a patient to match the anatomy of the patient.

The present teachings provide an orthopedic device manufacturing method. In one embodiment, the method includes preparing a three-dimensional image of a patient's joint, selecting a non-custom implant closely matching the joint, and modifying at least six angles of the implant to be patient-specific. In another embodiment, the method includes preparing a three-dimensional image of a patient's joint, selecting a non-custom femoral implant closely matching the joint, and modifying at least three lengths and six angles of the femoral implant to be patient-specific.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although some of the present teachings are illustrated for a knee implant, the present teachings can be used for any orthopedic implant.

The present teachings provide a manufacturing method that integrates patient's anatomic and medical information with interactive participation by a surgeon to select and manufacture an implant and, optionally, related surgical instruments, for a particular patient from generally three options: a custom made implant specific to the patient, an implant that is only partially custom-made or a semi-custom implant, and a standard off-the shelf implant. Similarly, off-the-shelf, custom-made, or semi-custom-made instrumentation (e.g. alignment guides, drill guides, cutting guides or other instruments) can be selected and manufactured, as recommended by the surgeon, for the surgical procedure. All the implant components, alignment guides, and other disposable instruments can be included in a package provided to a surgeon for a specific patient.

Figure 1:
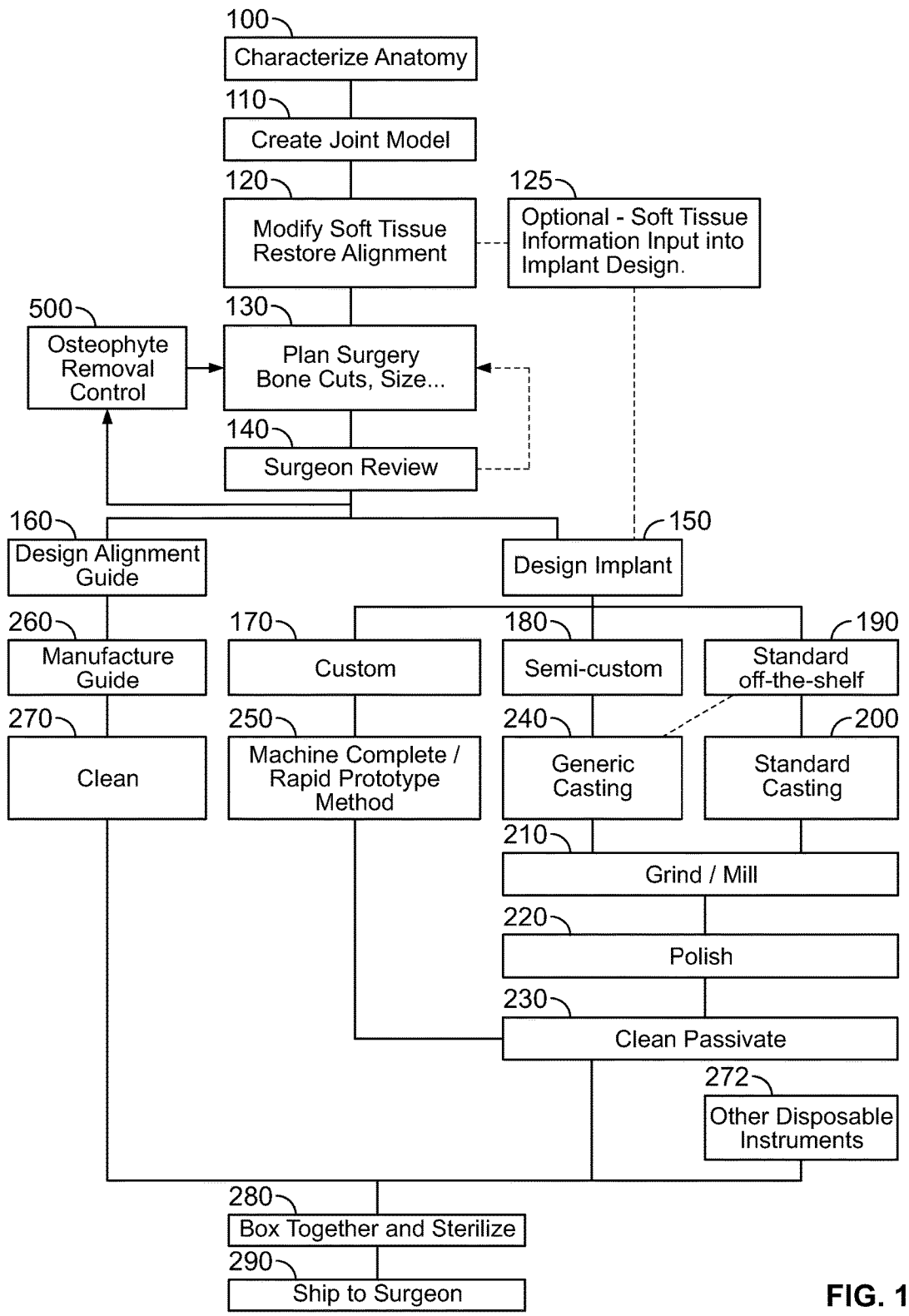
FIG. 1 is a flowchart of an implant manufacturing method according to the present teachings.

Referring to FIG. 1, an exemplary flowchart of an interactive implant manufacturing method according to the present teachings is illustrated. The portion of the patient's anatomy related to the orthopedic procedure and the implant is characterized and detailed at 100. The characterization can be performed with various imaging methods capable of obtaining a representation of the affected anatomy, including, for example, soft and hard tissues. The tissues can include bone, bone joints with or without cartilage, ligaments, or other soft tissue. The imaging methods can include, for example, MRI, CT, ultrasound, radiography or X-ray, cameras and other devices.

The image information for the patient can be obtained at a medical facility or a doctor's office and can be sent to the manufacturer in an electronic and/or digital form contained. The image information can be stored on a physical medium, such as a CD, DVD, flash memory device (e.g. memory stick, compact flash, secure digital card), or other storage device. The information may alternatively, or in addition, be transmitted electronically with the Internet or worldwide web using appropriate transfer protocols. Also, electronic transmissions can include e-mail or other digital transmission to any appropriate type of computer device, smart phone, PDA or other devices in which electronic information can be transmitted.

Appropriate handheld devices (used as illustrated in FIG. 13), can include handheld mobile device or portable communication devices, such as the iPhone® handheld mobile device sold by Apple Inc., a corporation of California, USA; the LG Shine® handheld mobile device sold by LG Corp. a corporation of REPUBLIC OF KOREA; or the Blackberry Bold® handheld mobile device sold by Research In Motion Limited a corporation of CANADA. The handheld device can be those that are held in the palm of a hand of a user, such as a surgeon (see FIG. 14). The surgeon can then enter data with a stylus, keyboard, touch screen, etc. The handheld device can use local area networks, cell phone networks, or other data transmission systems to communicate with a main memory and processor of a service provider (see FIG. 14).

Appropriate handheld devices can provide access to electronic communication or file transfer protocols, such as internet or electronic mail, to transfer or access information files. The handheld devices can have installed programs that can be used to manipulate the information files, as discussed herein. Alternatively, or in addition thereto, the handheld devices can access servers that process data files while receiving input through the handheld devices and displaying images to the surgeon or user via the handheld device. In certain instances, the handheld device may only be a client that does not process and edit a data file of the pre-operative plan.

With continued reference to FIG. 1, at 110, the information collected at 100 can be used to create a three-dimensional model or image of the bone or joint with or without associated soft tissue or related anatomy using commercially available computer modeling software from various vendors or developers, such as, for example, from Materialise USA, Ann Arbor, Mich. The three-dimensional model of the patient's anatomy can be viewed on a computer display or other electronic screen and can also reproduced as a hard copy on film or other medium and viewed by direct or indirect or backlight illumination. The model can be sized for viewing on any appropriate screen size and may be cropped, rotated, etc. as selected by the individual (e.g. the surgeon) viewing the screen.

At 120, soft tissue associated with the affected anatomy can be modified, or removed or repaired, to restore alignment of the joint, for example, or to remove torn or diseased tissue, or to cut or repair ligaments, or to provide natural or artificial ligament grafts. Soft tissue information can be optionally used as an additional design parameter or input for the implant design, at 125. For example, a custom or patient-specific bearing articulation of a knee joint can be designed based on the kinematic profile and the soft tissue/ligament information available for a particular patient. Further, kinematic information for the patient can be obtained by an actual gait analysis of the patient, and can also be obtained by computer modeling software that uses the MRI images of the patient's joints and associated ligaments, muscle or other soft tissue to derive kinematic analysis of the patient and corresponding recommendations for soft tissue modification, such as releasing a ligament, for example. Such software is commercially available from LifeModeler, Inc., of San Clemente, Calif.

At 130, a preliminary pre-operative plan of the surgical procedure can be prepared for surgeon or other medical user or technician review, including the planning of various bone resections, sizes and types of implants, and various geometric requirements including relevant dimensions, such as height, width, orientation of particular features, etc. The preliminary pre-operative surgical plan can include a recommendation of particular implants and associated instruments to be used in the surgical procedure, as discussed below. The preliminary pre-operative surgical plan can be in the form of digital images that can be viewed interactively using a computer modeling software, such as the software referenced above. The preliminary pre-operative plan and any further changes or a finalized pre-operative plan can be a plan devised to obtain a healthy or as close to healthy anatomical orientation after an operative procedure. The healthy anatomy can be based on natural or pre-injury anatomy or mechanically correct or efficient anatomical orientation.

At 140, the preliminary pre-operative surgical plan can be submitted to the surgeon (or other user) for review, either electronically or by land mail, and either in digital or hard copy form, as discussed above in connection with transmitting imaging information. In particular, the surgeon can review the resection planes shown in image of the patient's anatomy, make changes in the location, size and orientation of the resection planes and, generally, work interactively until the pre-operative plan from 130 is surgeon-approved. Specifically, the surgeon may approve the image of the patient's anatomy showing corresponding resection planes. As shown in FIGS. 7 and 8, the patient's anatomy 510, as represented in the image, can be, for example, a distal femur with approved resection planes including medial and lateral anterior chamfer planes 513, medial and lateral anterior cut planes 511, medial and lateral posterior chamfer planes 512 and medial and lateral posterior cut planes 514. Following the surgeon's approval of the anatomy and the resection planes at 140, the surgeon is provided with the opportunity to remove one or more osteophytes/protrusions from the image of the patient's anatomy 510 at surgeon-selected locations and depths at 500 (See FIG. 6). Removal of such protrusions and smoothening of the joint surface that receives the implant can parallel the intra-operative joint preparation by the surgeon and improve the actual fit of a surgeon-selected implant, whether patient-specific, semi-custom, or off the shelf.

An automated osteophyte/protrusion removal control module 500 can be incorporated in the planning stage of the manufacturing method illustrated in FIG. 1. The automated osteophyte/protrusion removal control module 500 can be provided as a separate pre-operative planning module, as shown in FIG. 6, or it can be incorporated and/or fully integrated with the manufacturing method illustrated in FIG. 1.

Certain parts of the bone, including various bone bumps, protrusions, growths and osteophytes can be generally removed from the three-dimensional reconstruction of a patient's anatomy before designing a patient-specific implant or semi-custom implant, or before selecting an off the shelf implant. The automated osteophyte/protrusion removal control module can replace a time-consuming and potentially less accurate manual modification of the three-dimensional image to remove such bone growths or osteophytes by an experienced image or CAD technician. The automated osteophyte/protrusion removal control module 500 can provide more accurate and faster removal of such bone irregularities, which can vary in shape, location and size from patient to patient. It will be appreciated that the osteophyte/protrusion removal control module 500 can be used for smoothing out a bone surface by removing any type of bone protrusion, including bumps, irregularities and osteophytes. According to the present teachings, osteophytes are illustrated as exemplary, but not exclusive, candidates for complete or partial removal.

Figure 6:
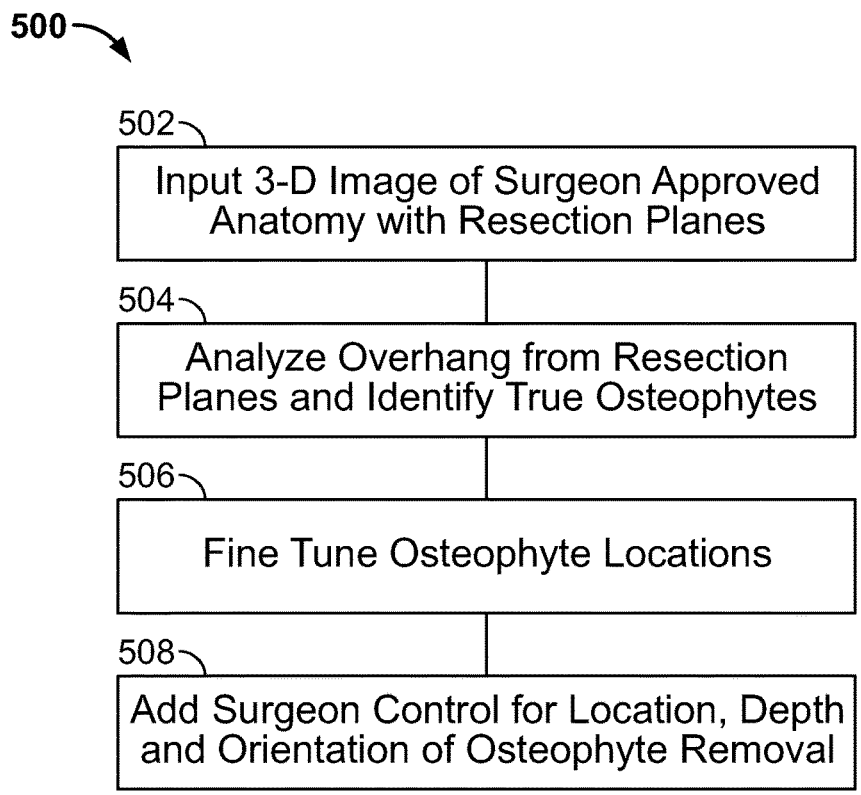
FIG. 6 is a flow chart for an osteophyte/protrusion removal control method according to the present teachings.
Figure 7:
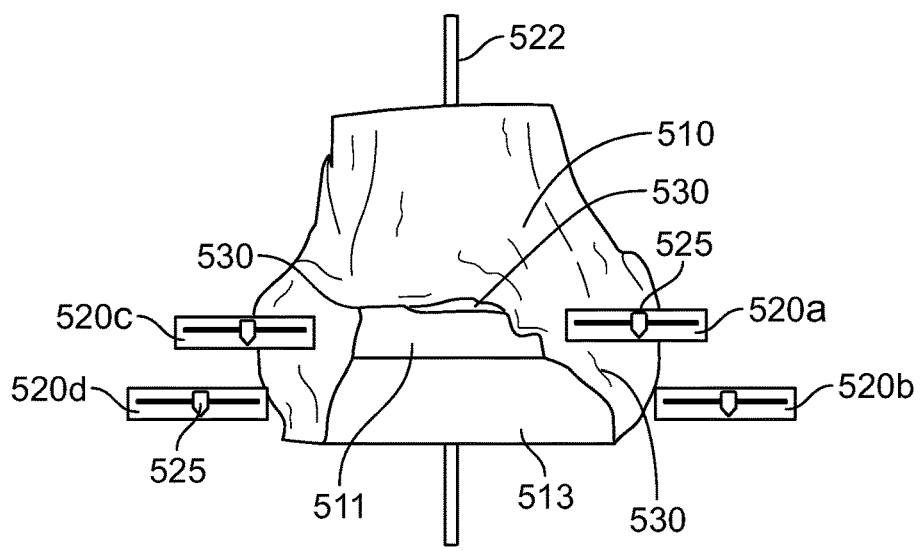
FIG. 7 is a representative image of a patent's anatomy showing osteophyte/protrusion control tools for modifying the image.
Figure 8:
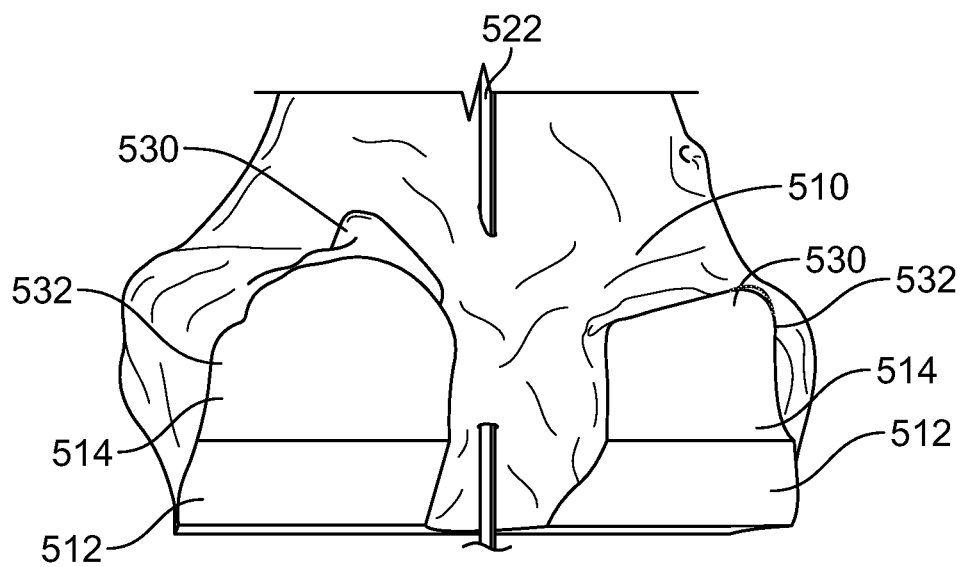
FIGS. 8 and 9 are representative images of a patent's anatomy showing exemplary osteophyte/protrusion locations.
Figure 9:
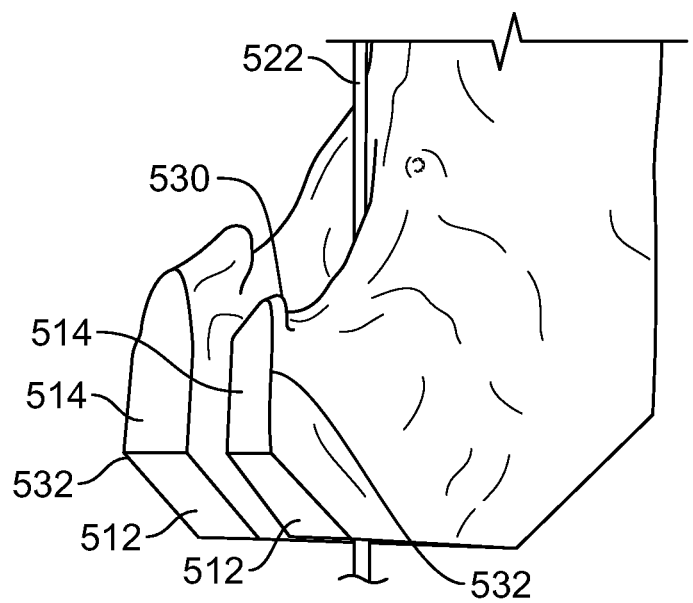

Referring to FIG. 6, the osteophyte/protrusion removal control module 500 can start 502 with an input of the three-dimensional image of the patient's anatomy 510 including resection planes, as shown in FIGS. 7-9, after review and approval of the resection planes by the surgeon (or other user, including other professionals or technicians) at 140 of FIG. 1. In the exemplary illustration of FIG. 7, the image of the patient's anatomy 510 can be analyzed to identify osteophyte/protrusion locations 530 (at 504 of FIG. 6) by determining tissue or bone overhang protruding past outer edges 532 of the various resection planes, such as the resection planes illustrated at 511, 513, 512 and 514 in FIGS. 7-9. If such osteophyte/protrusions 530 extend beyond the edges of the resection planes in the direction of the planned or anticipated implant location, the osteophyte/protrusions 530 can interfere with implant fitting.

Figure 10:
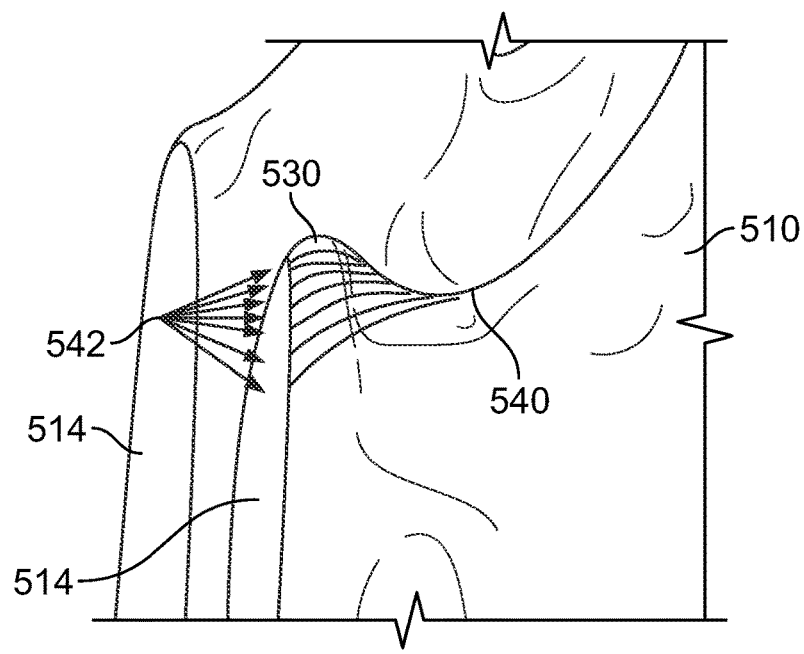
FIG. 10 is a representative image of a patent's anatomy showing representative depth control selections for surgeon manipulation.

Referring to FIGS. 6, 7 and 10, in addition to identifying the location of osteophytes/protrusions 530, the osteophyte/protrusion removal control module 500 can provide visual control for the surgeon to select the aggressiveness of osteophyte/protrusion removal, or the degree of smoothening and/or flattening of the corresponding joint anatomy. Specifically, by fine-tuning the osteophyte/protrusion locations, at 506 of FIG. 6, the surgeon can control the depth of the osteophyte/protrusion removal in a continuous or discrete manner. In one aspect, a landmark location 540 for each osteophyte/protrusion 530 can be identified and pegged for measuring from and initiating a continuous series of constant or variable depth contours 542 to aid the surgeon in selecting the depth of osteophyte/protrusion removal. The depth contours can be automatically generated by the computer software that generates a three-dimensional model or image of the anatomy, such as the software commercially available, for example, from Materialise USA, Ann Arbor, Mich. The landmark location 540 can be a location of lowest possible depth in the vicinity of the identified osteophyte/protrusion, a minimum, or a valley location, as shown in FIG. 10. Although the depth contours 542 are shown as discrete in FIG. 10, it will be appreciated that a continuous removal control can be provided, such that the surgeon can exercise unlimited choices of depth contours for removal. The depth contours 542 can represent curved smoothed-out surfaces under the original osteophyte/protrusion 530 and can be exposed after an overlying area is shaved or peeled in the image of the patient's anatomy 510 by the operation of graphical or visual removal tools provided on the image of the patient's anatomy 510. The surgeon or other user can manipulate the graphical removal tools with a user interface, such as a mouse, touch screen, joystick, slide pad, or other user interface.

Referring to FIG. 7, various visual removal tools can be provided for on-screen manipulation and control by the surgeon, at 508 of FIG. 6. For example, a removal tool corresponding to each edge of a resection plane can be provided and used to visually/graphically remove a portion of an osteophyte/protrusion associated with a particular edge 532. In FIG. 7, four such exemplary removal tools 520a, 520b, 520c, 520d (collectively referenced as 520) are shown, each removal tool associated with an edge of a resection plane, such as lateral and medial chamfer plane and lateral and medial cut plane. Although the removal tools 520 are illustrated as straight sliders in FIG. 7, the amount removed follows a depth contour 542, as illustrated in FIG. 10. The removal tools 520 can include a visual indicator 525 that can provide information to the surgeon in the form of a number on a scale indicative of the depth of aggressiveness of osteophyte/protrusion removal. In another aspect, the indicator 525 can provide visual information in terms of variable color in shades gradually changing from minimum depth removal (green, for example) to maximum depth removal (red, for example).

Figure 11:
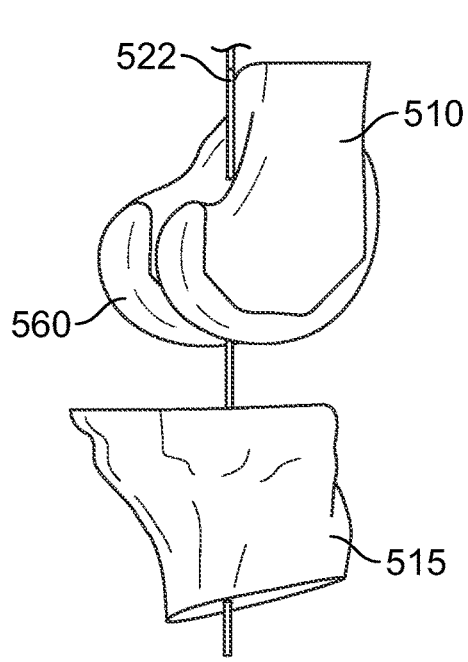
FIGS. 11 and 12 are representative images of a patent's anatomy after osteophyte/protrusion removal with exemplary implants attached thereon.
Figure 12:
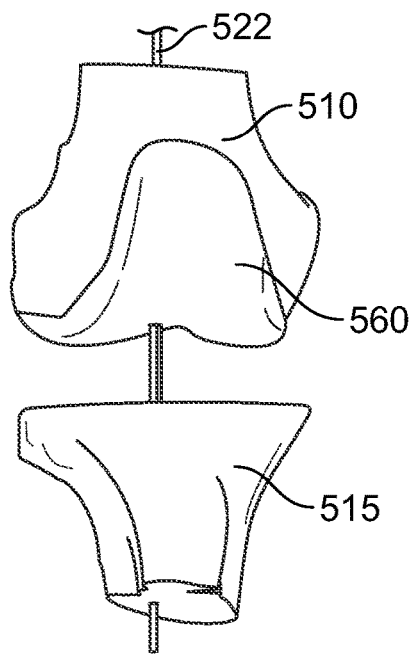

After the surgeon completes the osteophyte/protrusion removal, the surgeon can manipulate and superimpose implant images in relation to the modified patient's anatomy 510. In FIGS. 11 and 12, exemplary images of a resected femur 510 and tibia 515 referenced relatively to a mechanical axis 522 are illustrated. The femur image illustrates the patient's anatomy 510 after the osteophytes/protrusions 530 shown in FIGS. 8 and 9 have been removed and a femoral implant/component 560 is placed on the resulting smoothed out surface that follows one of the depth contours 542 shown in FIG. 9.

Figure 1A:
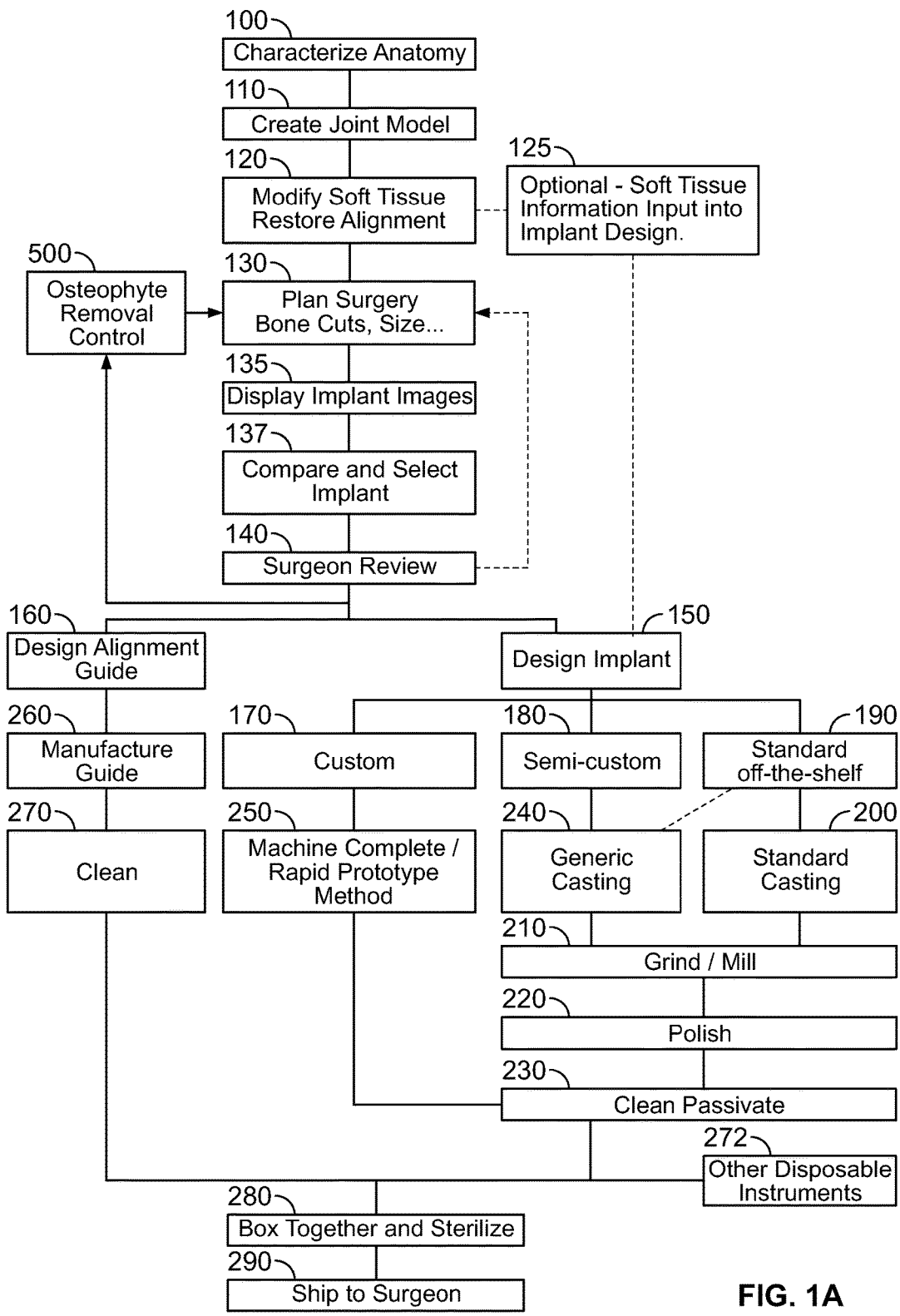
FIG. 1A is a flowchart of an implant manufacturing method according to the present teachings.
Figure 1B:
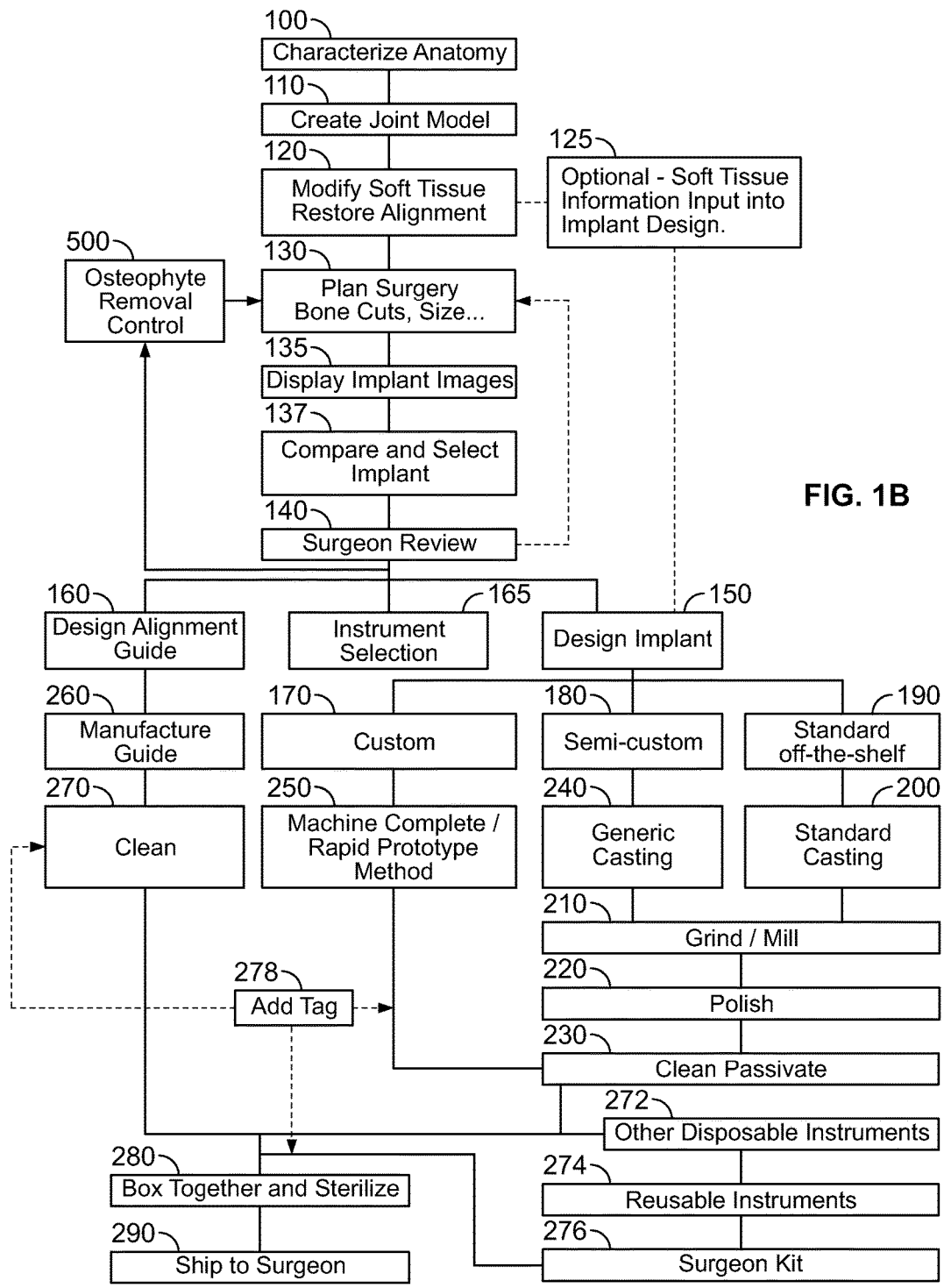
FIG. 1B is a flowchart of an implant manufacturing method according to the present teachings.

Referring to FIGS. 1, 1A, and 1B, based on the preliminary pre-operative surgical plan and the patient information, the surgeon can make a recommendation regarding the design of the implant at 150, and any desired associated alignment guides at 160. At 150, the surgeon can recommend a method of designing an implant. Specifically, the surgeon can select one of the following three options: a first option of a custom or patient-specific implant at 170 or a second option of a semi-custom made implant at 180, or a third option of a standard or off-the-shelf implant at 190. The surgeon can also include recommendations and preferences for various custom and non-custom instruments to be used in the procedure at the surgeon review at 140, as well as at the selection and design of implant at 150 and selection and design of alignment guides 160. It will be appreciated that, based on the surgeon's recommendation at 140, the preliminary pre-operative surgical plan can be modified at 130, including all the surgeon's preferences regarding anatomy modification (osteophyte removal, resection planes, etc.), implant design, alignment guide design and selection of various tools and instruments, and then resubmitted to the surgeon for approval.

A custom-made implant is a patient-specific, one of a kind implant specifically made for a particular patient, and consequently there is no inventory associated with such implant. Standard or off-the-shelf-implants are available and stocked in a number of sizes, typically six or more, and a number of configurations or types, including bilateral or unilateral implants, constrained, semi-constrained, mobile, etc. Because of the variety of sizes and configurations that are kept in stock to accommodate different patients, a large inventory of standard implants is created, and several molds for each type and size of implant may be used. As described below in detail, semi-custom implants provide an intermediate solution between custom-made and off-the-shelf implants. Semi-custom implants reduce the size of inventory and molds required for production, while allowing some degree of patient-specific customization.

Custom or patient-specific implants, when approved by surgeon at 170 for a specific patient, can be manufactured for the patient by rapid prototyping methods, such as stereolithography or other similar methods, or by CNC milling, or other automated or computer-controlled machining, or by robotic methods, at 250. Manufacturing can take place at a manufacturing center or facility in situ or at remote or off-site location. It will be understood that in situ manufacturing is used as a short hand for a manufacturing site of the original equipment manufacturer (OEM), but can be physically located at a different facility of the OEM. Off-site or remote manufacturing will be understood to refer to facilities operated by other manufacturers who are contracted by the OEM for manufacturing all or some of the implants, components or parts for the surgical procedure.

Off-the-shelf implants, when approved by the surgeon a 190, can be manufactured by standard casting methods from bar stock or other stock material at 200, then shaped to a final shape and size by grinding or milling at 210, polished at 220, and then cleaned/passivated at 230. Such off-the-shelf implants can be part of an existing inventory, or mass-produced, or produced by just-in-time agile manufacturing methods.

Semi-custom implants, when approved by the surgeon at 180, can be made from a generic casting at 240, as described below, or by modifying existing standard implant designs to match various features or parameters based on the anatomy of the patient, as described in co-pending patent application entitled Patient-Modified Implant and Associated Method, Ser. No. 12/103,834, filed on Apr. 16, 2008, the disclosure of which is incorporated by reference herein. After the generic casting is modified for certain parameters of a patient, it can be processed at aspects 210-230 to a passivated form. Patient-specific parameters can include parameters relating to the size of the implant, including height, width, various articulation parameters or angles, etc., as discussed in specific example below in reference to FIGS. 3-5.

The surgeon's review of the surgical plan at 140 may further include, at 160, a request for one or more patient-specific alignment guides to be used with the implant. Patient-specific alignment guides are described in co-pending patent application Ser. No. 11/756,057, filed on May 31, 2007, Ser. No. 11/971,390, filed on Jan. 9, 2008, Ser. No. 12/025,414, filed on Feb. 4, 2008, and Ser. No. 12/039,849 filed on Feb. 29, 2008. The alignment guides can be manufactured at 260 with by rapid prototyping methods, such as stereolithography or other similar methods or by CNC milling, or other automated or computer-controlled machining or robotic methods, and cleaned at 270. The alignment guides, the implants and optionally other disposable instruments (at 272) can be packaged and sterilized at 280, and forwarded to the surgeon or the surgeon's medical facility for implantation at 290.

Figure 1C:
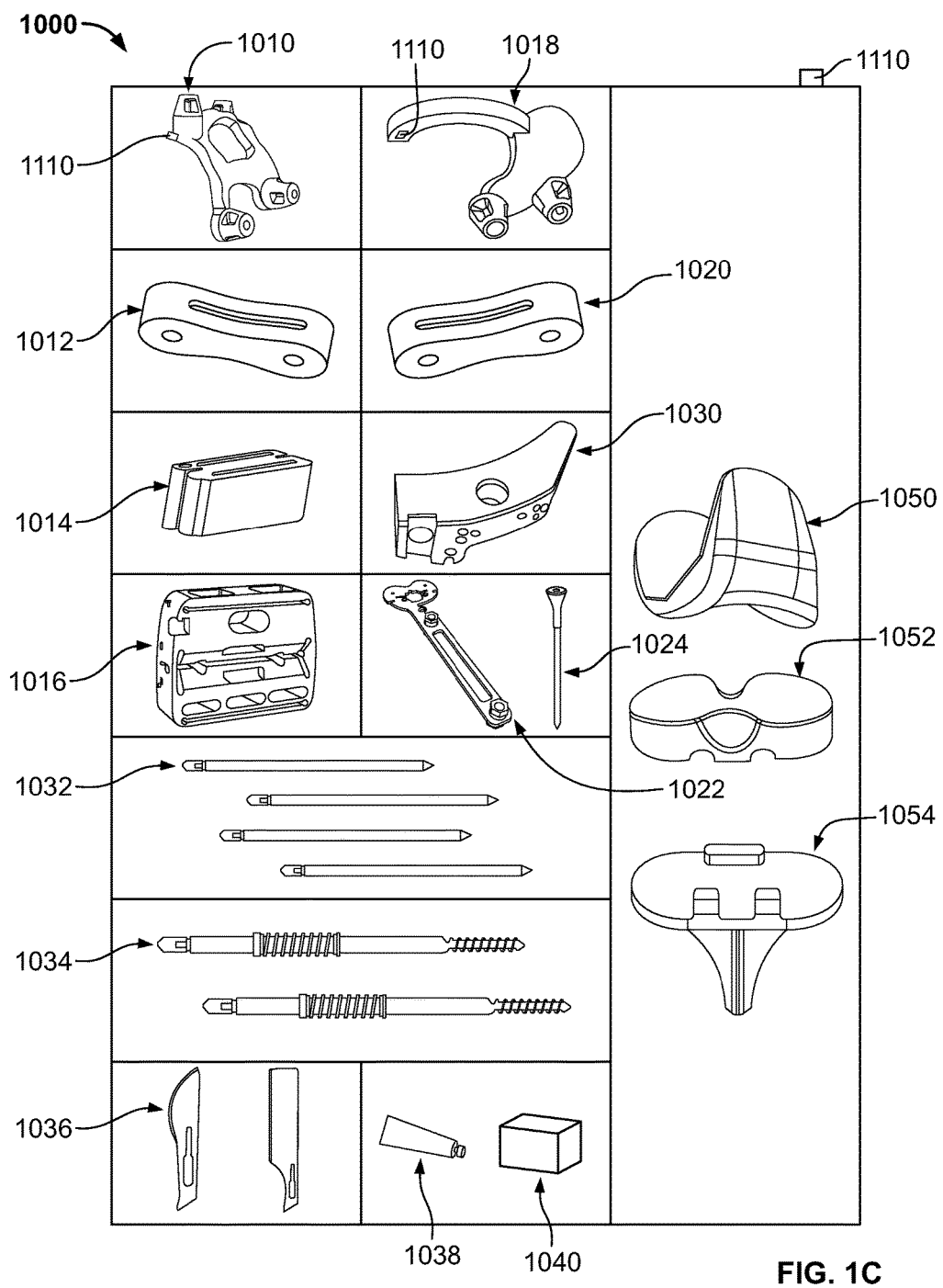
FIG. 1C is a surgical kit according to the present teachings.

The methods described in connection with FIGS. 1A and 1B can be modified to incorporate additional features, as illustrated in FIG. 1C. The additional features can include a preparation of a surgeon kit 1000 and optionally a tracking procedure in which tracking tags are added at 278 to the various parts that are included in the surgeon kit 1000. The tracking procedure can be incorporated in the manufacturing, cleaning, sterilizing, assembling and boxing the various components up to implantation and can be maintained, for example through the procedures at 260, 270, 230, 272, 274, 276, 280, and 290, as shown in FIG. 1B. The surgeon kit 1000 and can be tracked during assembling/stocking the surgeon kit 1000 with the various components, and the tagged components can be tracked from manufacture to implant procedure.

Referring to FIGS. 1B-1E, a surgeon kit 1000 can be generated at 276. The surgeon kit 1000 can be designed and assembled during the process described above in FIGS. 1A, 1B and 1C and during the manufacturing of the patient-specific alignment guides and implants. The surgeon kit 1000 can be assembled based on surgeon preferences and can include a set of implants, such as, for example, a femoral implant 1050, a bearing 1052 and a tibial implant 1054, for an exemplary knee replacement procedure, or other implant components depending on the surgical procedure and the surgeon's preference. The implants can be patient-specific, of semi-custom or standard off-the-self as described above. In addition to or instead of the implants, surgeon-selected alignment guides (at 160, 165 and 260), other disposable instruments (at 274) and other reusable instrument (at 274) selected according to the surgeon's preferences can be included in the surgical kit 1000. In one embodiment, the surgeon kit can include only instruments, such as, for example, alignment guides and other tools, designed to be disposable.

In the exemplary illustration of FIG. 1C, a surgeon kit 1000 for a knee procedure is shown to include a femoral alignment guide 1010, a tibial alignment guide 1018, a femoral drill guide 1012, a tibial drill guide 1020, a femoral distal cutting block 1014, a tibial cutting block 1030, a four-in-one femoral cutting block 1016, a tibial template 1022 with alignment rod 1024. The alignment guides are single-use and disposable. The various drill guides and cutting blocks can be re-sterilazable and reusable, although disposable drill guides, cutting blocks and other tools can also be designed. Additionally, a set of trochar pins 1032 and a set of spring drill pins 1034 can be included. Depending on the surgeon's preferences, various surgical blades 1036 can be added and additional medical products, such as, for example, bone cement 1038, or other medical supplies or biologics 1040.

Referring to FIGS. 1B-1E, a tracking system can be incorporated with the surgeon kit 1000. Tracking tags 1110 can be added at 278 optionally to the alignment guides, the implants and/or the entire surgeon kit 1000. The tracking tags 1110 can be simple barcode tags, or other scan readable tags or radio frequency identification (RFID). The tags 1110 can be added to individual instruments or on the entire surgical kit 1000, outside the box. The tracking tags can include patient-specific information and/or surgeon information, such as, for example, patient's name, age, gender, procedure to be performed, surgeon's name; clinic or hospital location, etc.

Figure 1D:
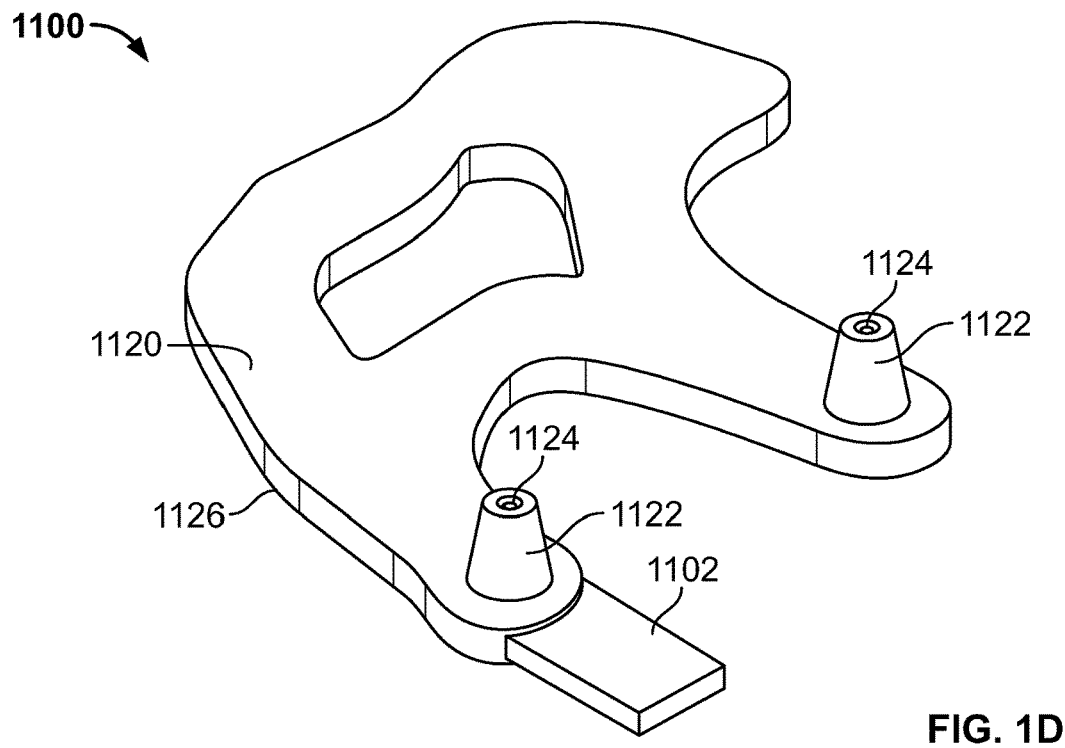
FIG. 1D is a patient-specific alignment guide according to the present teachings.
Figure 1E:
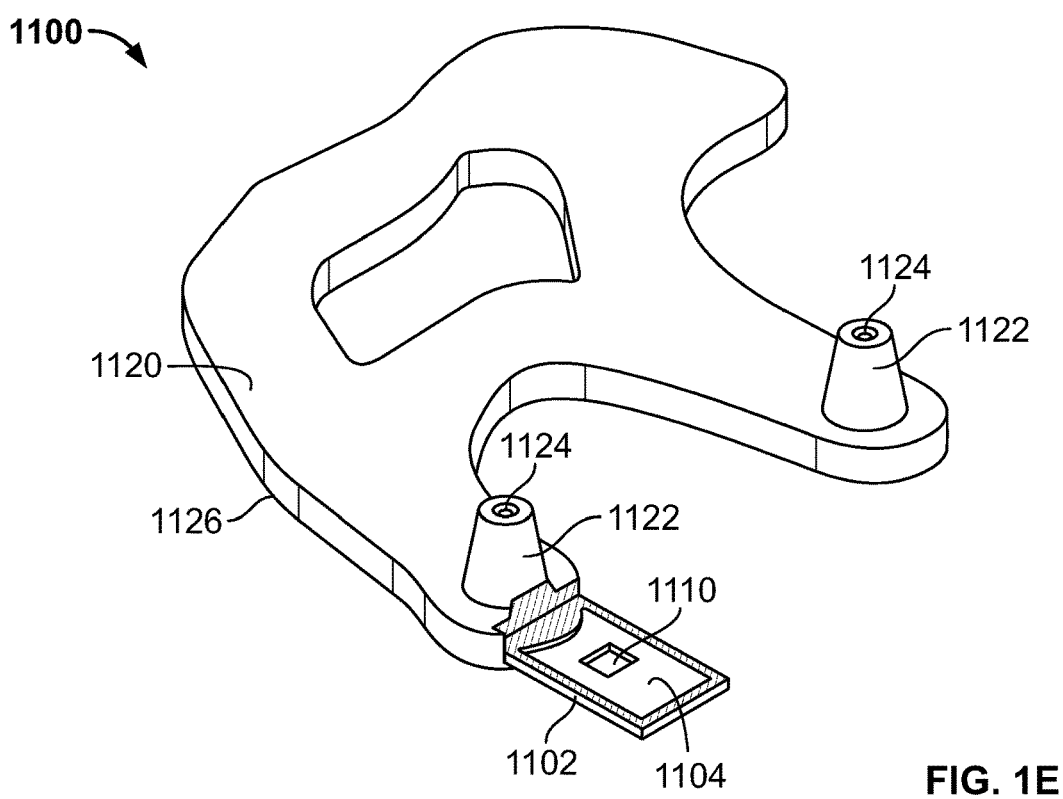
FIG. 1E is a patient-specific alignment guide according to the present teachings.

The tracking tags 1110 can be removable. For example, the tracking tags 1110 can be attached with removable glue sticks or frangible attachments. In one embodiment, the tracking tags 1110 can be incorporated in a frangible extension 1102 of an alignment guide 1100, as illustrated in FIGS. 1D-1E. The exemplary alignment guide 1100 can include a body 1120 having a patient-specific engagement surface 1126 for engaging a complementary surface of the corresponding anatomy of the patient and one or more alignment formations 1122 defining guiding bores 1124 for guiding alignment or drill pins or other instruments. The extension 1102 can be prepared or incorporated during the manufacturing process, for example, during the layering process of a rapid prototyping method, and can include a pocket 1104 in which a tracking tag 1110 is inserted, as part of the layering process. Layering can continue and cover the tracking tag 1110. In another embodiment, the extension 1102 can be a blank of larger dimensions from which the pocket 1104 is machined for the tracking tag 1110. The tracking tag 1110 can be removed or broken off by the surgeon. Tracking of the patient-specific (and surgeon) information can be provided for the entire manufacturing procedure from start to finish, i.e., from the manufacturing of the tracked components to assembling the surgeon kit 100 to the implant procedure at the operating theater or site.

Figure 2:
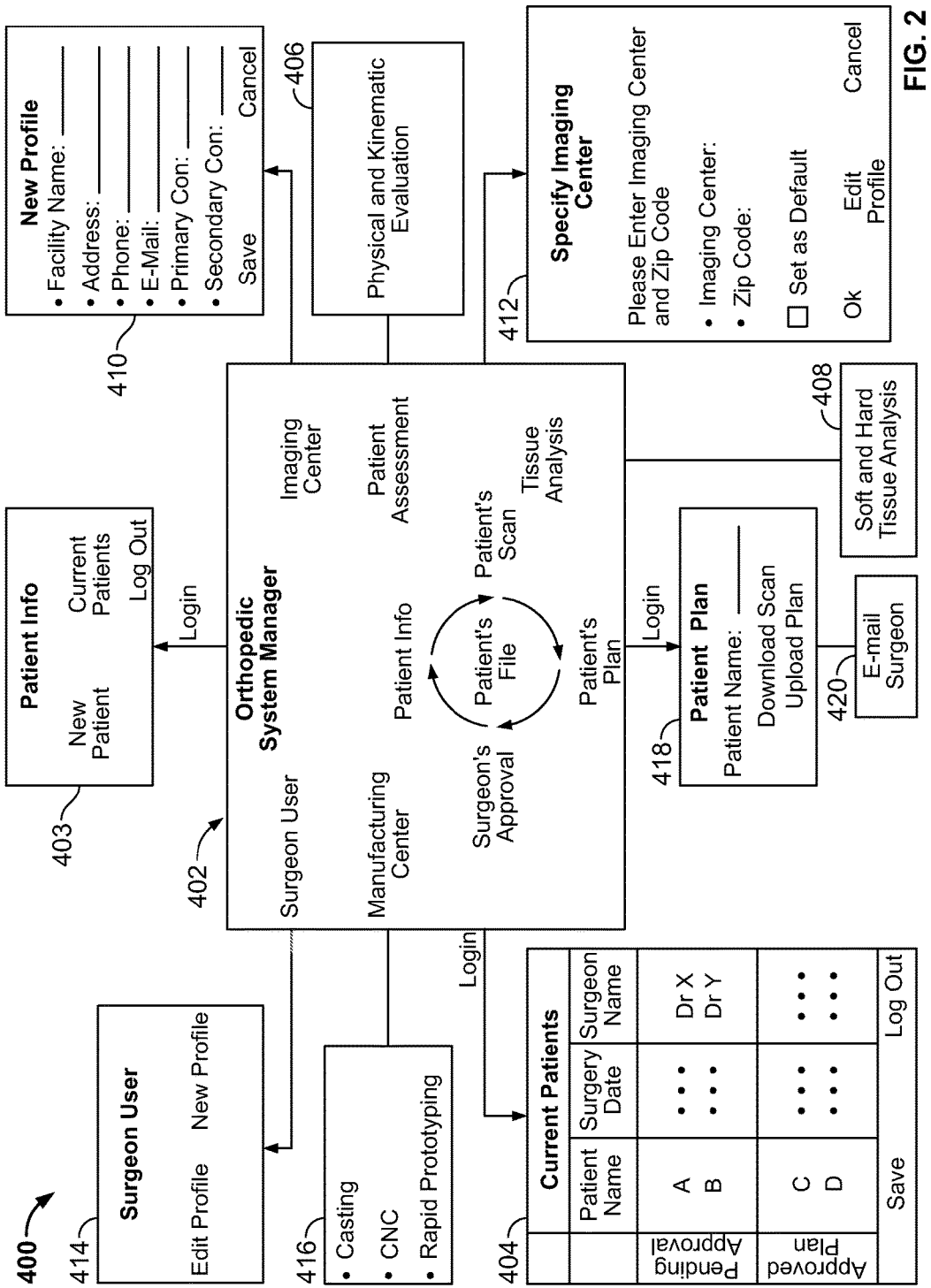
FIG. 2 is a diagram illustrating a computer interface for an implant manufacturing method according to the present teachings.

Referring to FIG. 2, a computer interface 400 to a computer program for the management of the manufacturing method is illustrated diagrammatically. An orthopedic system manager 402 can be in the form of software or other computer program associated with the original equipment manufacturer. The orthopedic system manager 402 can be accessible locally via dedicated computer machines or computer terminal directly communicated with software either by hard wire or wirelessly. The orthopedic system manager 402 can also be accessible remote remotely via the Internet or other remote communication portals using any electronic or other devices that can connect to the Internet or other web-based network, or other similar communication networks, including cable, satellite and telephone-based networks.

The system manager 402 can provide access to patient file information, including lists of all current patients at 403, and surgery dates, surgeons, and approval status of the surgical plan for each patient, at 404. Each patient file can include personal and medical information of the patient, such as, for example, weight, height, gender, age, lifestyle, pertinent medical records and medical history, as well as information on patient assessment that includes physical and kinematic evaluation pertaining to the orthopedic procedure at 406, and soft and hard tissue analysis at 408, including information provided at aspects 120 and 125 of FIG. 1, as discussed above. Imaging center information for patient scans, as discussed in relation to aspects 100 and 110 of FIG. 1, can added or modified at 410, and an imaging center for each specific patient can be specified at 412. Surgeon profiles, including surgeon preferences regarding anatomic axes alignment or implant and instrument preferences that can be taken into account when preparing the preliminary preoperative plan discussed at aspect 130 of FIG. 1, can be created and edited at 414. Information and selection of manufacturing centers can be accessed at 416 for manufacturing the implants and or alignment guides as discussed in relation to aspects 260, 250, 240, and 210-230 of FIG. 1. The preliminary pre-operative surgical plan for each patient can be provided at 418, as discussed above at 140 in reference to FIG. 1, and e-mailed or otherwise communicated to the patient's surgeon at 420.

Figure 3:
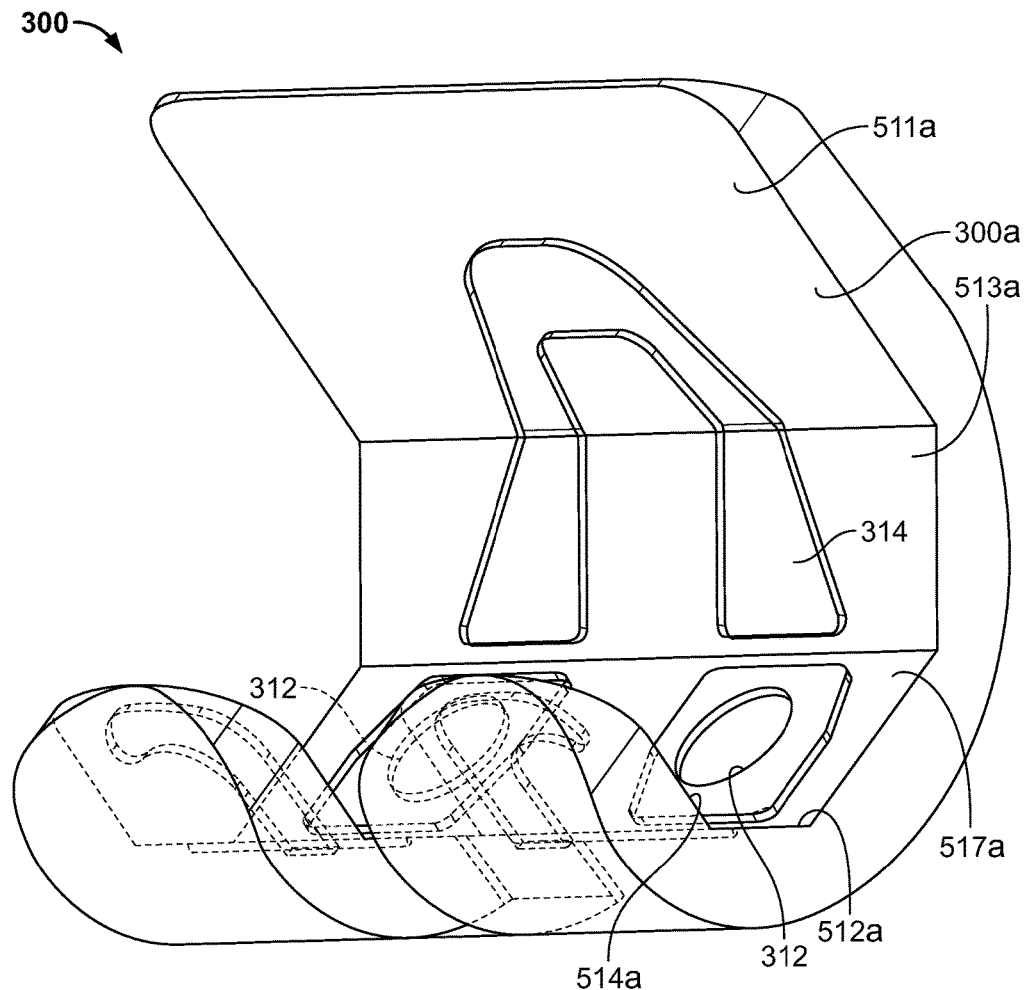
FIG. 3 is perspective view of a generic casting of an implant according to the present teachings.
Figure 4:
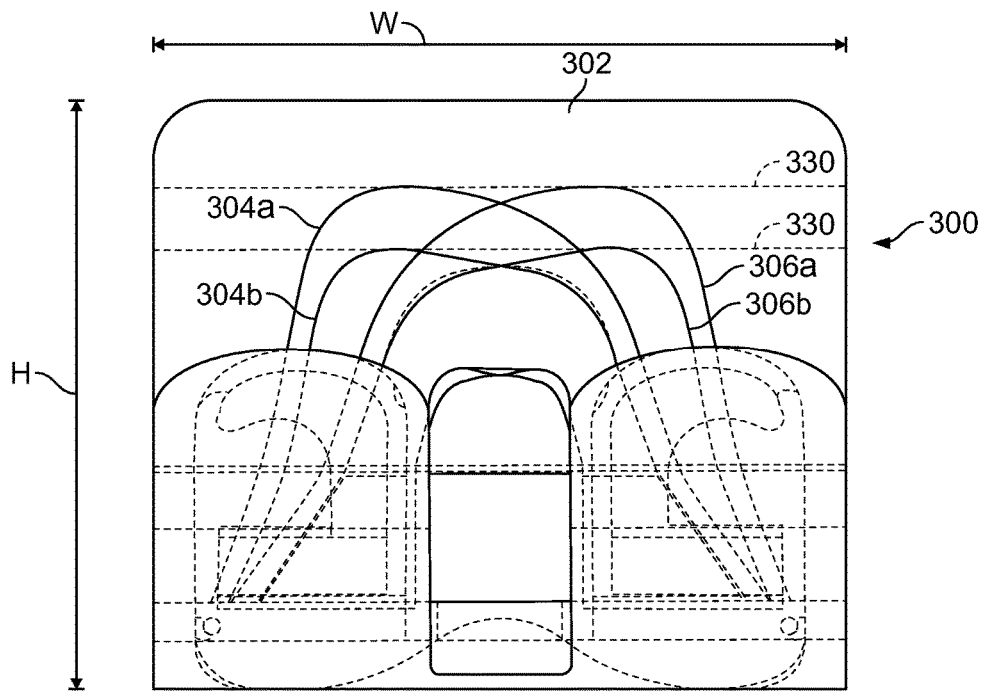
FIG. 4 is a posterior view of a generic casting according to the present teachings.
Figure 4A:
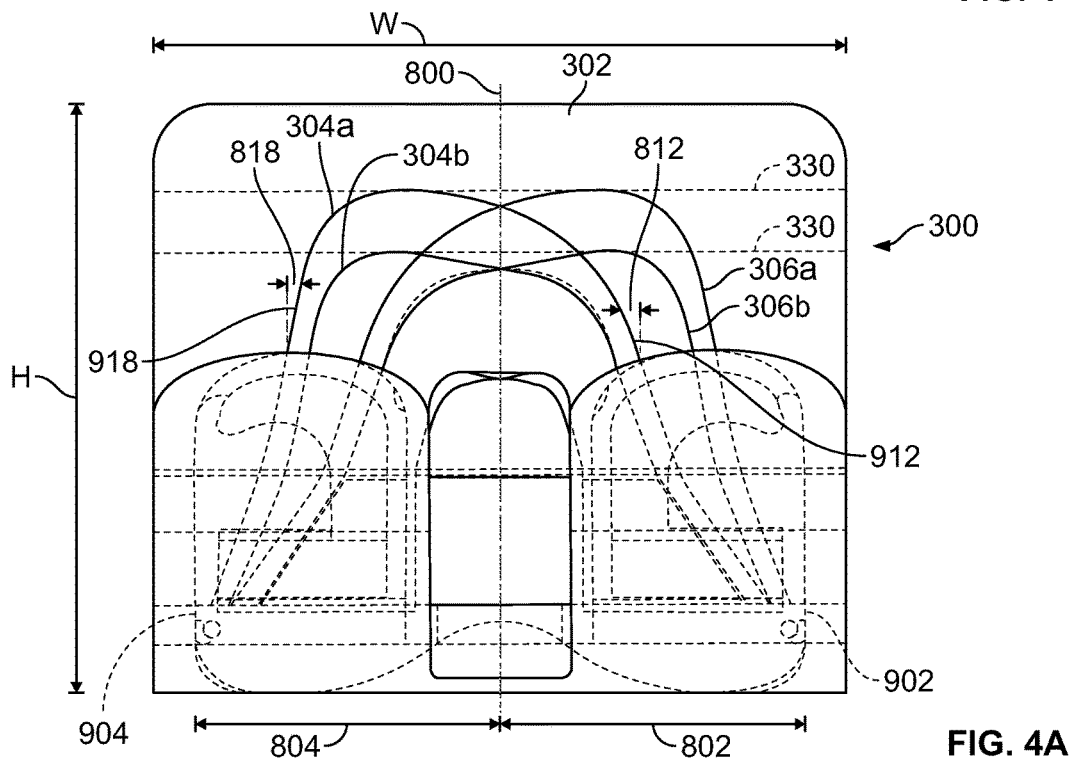
FIG. 4A is a posterior view of a generic casting including a plurality of additional modifiable features according to the present teachings.
Figure 5:
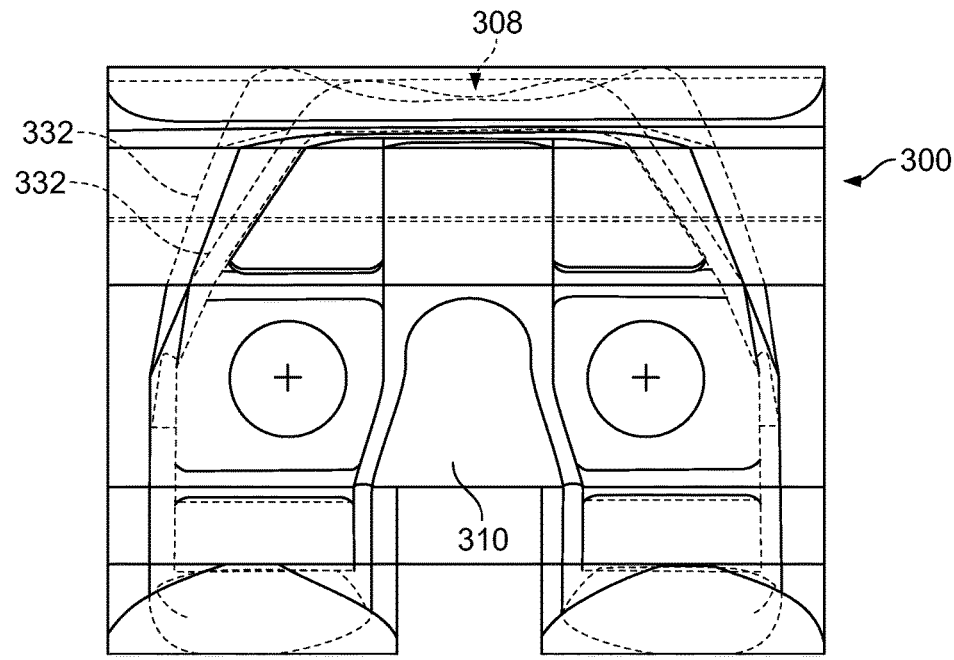
FIG. 5 is a plan view of a generic casting according to the present teachings.
Figure 5A:
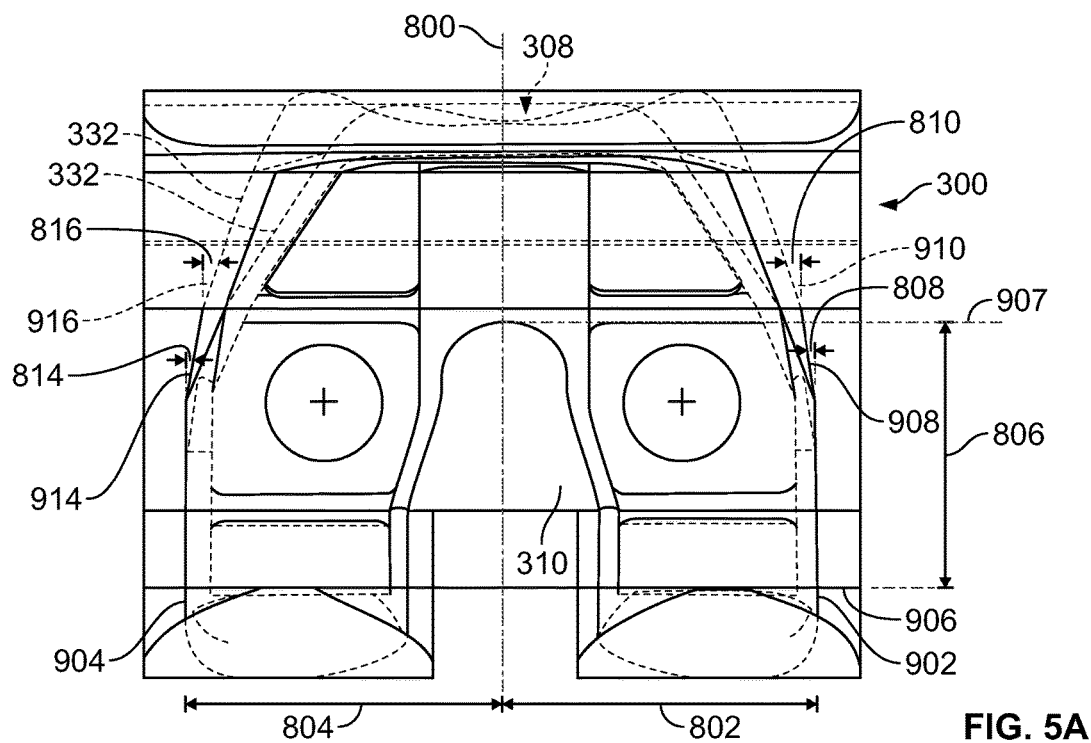
FIG. 5A is a plan view of a generic casting including a plurality of additional modifiable features according to the present teachings.

As discussed above at aspects 150 to 190 of FIG. 1, one implant option includes manufacturing semi-custom implants by generic casting. Illustrative examples of generic casting of a semi-custom femoral implant/component are shown in FIGS. 3-5. A generic casting 300 of the implant is a casting that is more specialized than ordinary bar stock, from which any size of implant can be made, but less specialized than the off-the-shelf implants that are available in a particular number of sizes, typically six-to ten sizes and are finished from specific castings of those sizes. The generic casting can be made in a size and shape that can accommodate a range of variable features for the implant, and at the same time can be machined to multiple sizes, such as three or four smaller sizes. In contrast, off-the-shelf implants require a mold or casting for each offered size, and a larger inventory of available sizes for each implant component. The generic casting can generally include geometric features which are size/shape and/or patient-independent or universal, and also features that are size/shape or patient-specific, as discussed in the examples below. More particularly, the generic casting can include at least one geometric feature that will remain unchanged for any patient or universal feature, and at least one geometric feature that can be specifically customized for and is specific to a particular patient. Additionally, generic castings can be provided in the same sizes as off-the-shelf components, although generic castings can have different shapes than off-the-shelf components.

Referring to FIGS. 4 and 5, an exemplary generic casting 300 of a femoral implant is illustrated. In this example, the generic casting 300 can have an anterior flange 302 of medial-lateral width W, and/or a height H and/or other geometric dimensions to accommodate multiple sizes of femoral implants. For example, multiple sizes of left-sided implants 304a, 304b, and various sizes of right-sided implants 306a, 306b can be formed by a single generic casting. In addition to multiple sizes, multiple shapes can be made from a single generic casting. Appropriate markings or indentations or score lines for cutting to size can be provided, such as height markings 330, for example. The implant for a particular patient can be formed from the generic casting 300 by selecting particular features, such as the width W or height H, or other geometric features for a particular patient and machining the generic casting 300 to provide the size, dimension or shape, or combinations thereof for that particular geometric feature.

Referring to FIG. 5, the generic casting 300 does not include a patella track feature, but provides an area in which a custom patella track 308 can be machined at a custom angle or custom shape for each specific patient. The generic casting 300 can also include additional material in the intercondylar notch area 310 to allow for custom machining of the intercondylar notch area 310 to accommodate various types of articulation or constraint in relation to a tibial implant, such cams or intercondylar boxes, and other contact areas for articulation with the tibial implant in accordance with a kinematic plan for the joint of the specific patient. Custom shapes of various other portions of the implants can also be prepared fro the generic castings. Separate molds for posterior stabilized and cruciate retaining articulations can be made, each mold capable of accommodating multiple sizes of the corresponding implant type. For example, the intercondylar notch area 310 can be machined for line or area contact with the articular surfaces of a tibial implant of various degrees of flexion. Exemplary articulations are disclosed in commonly assigned U.S. Pat. Nos. 6,589,283, 6,413,279, and 6,165,223, and in co-pending U.S. patent application Ser. No. 10/840,765 filed on May 6, 2004, all of which are incorporated herein by reference. Various markings 332 corresponding to different sizes can be provided.

Referring to FIG. 3, the generic casting 300 can include at least one patient-independent or universal feature, such as, for example, universal cement wells 312 or other universal features. Such universal features can be used with any internal geometry 314, which can be machined into the generic casting 300 to accommodate the appropriate shape and/or size for a specific patient.

Figure 5B:
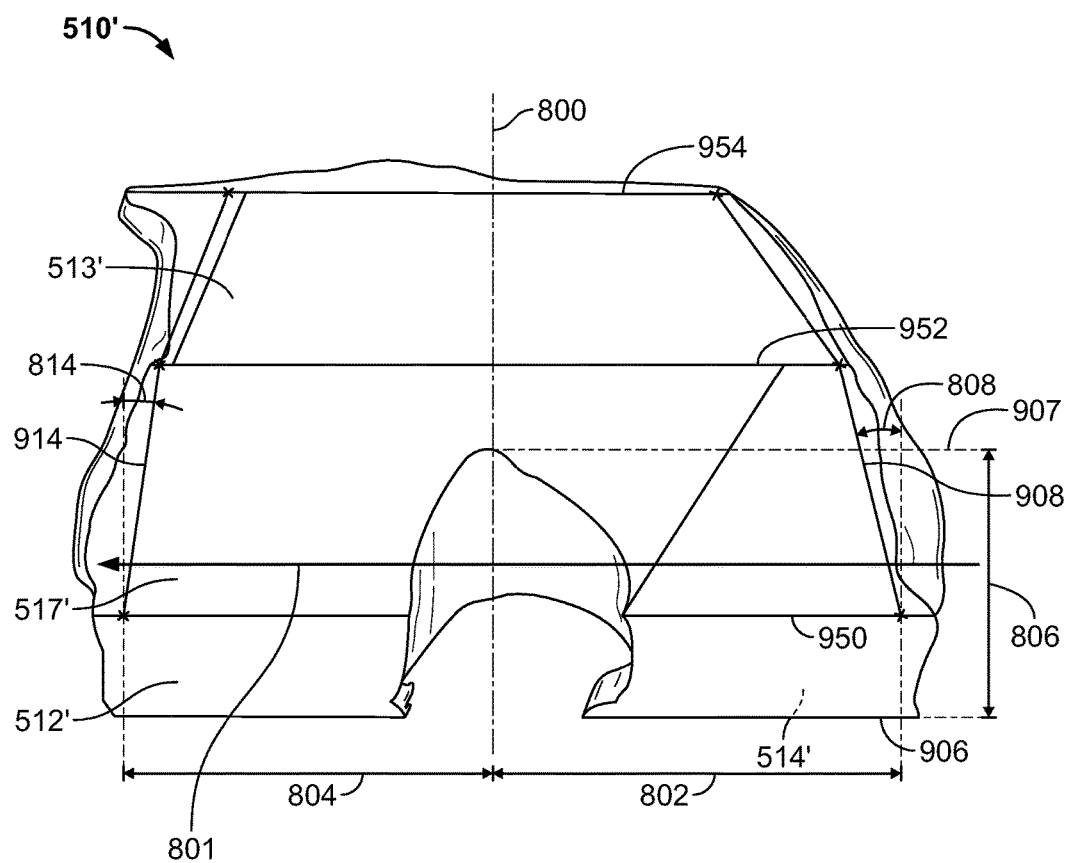
FIG. 5B is a distal view of a three-dimensional image of the patient's distal femur showing planned resection planes according to the present teachings.
Figure 5C:
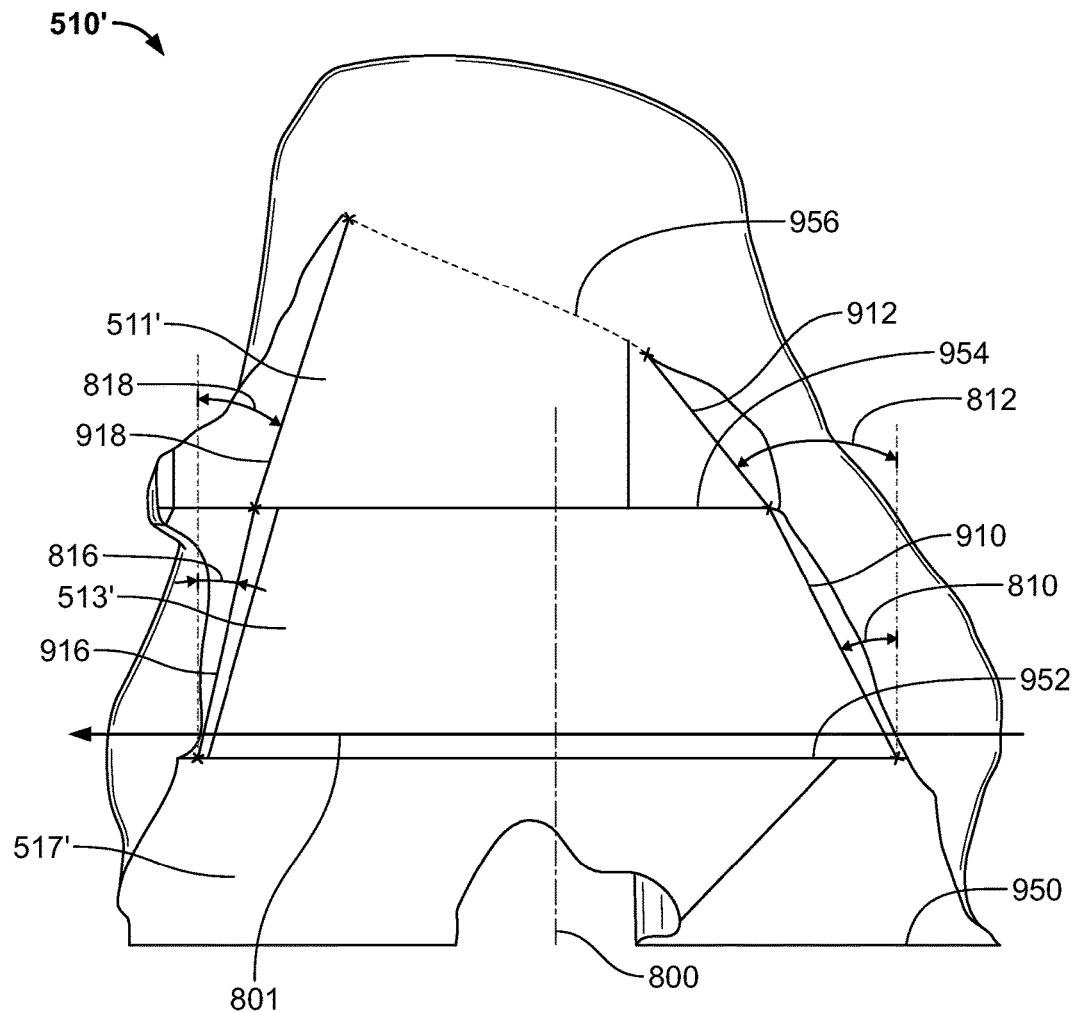
FIG. 5C is a anterior view of a three-dimensional image of the patient's distal femur showing planned resection planes according to the present teachings.

Referring to FIGS. 3, 4A, 5A, 5B and 5C, a semi-custom implant (304a, 304b, 306a, 306b) can also be generated from a generic casting 300 by customizing a plurality of features based on the patient's anatomy during the pre-operative planning stage in addition to or instead of the parameters discussed above. The generic casting 300 can include a standard, non-custom articulation surfaces for the medial and lateral condyles and an internal bone engagement surface 300a for engaging the resected femur and including five internal planes 511a, 513a, 517a, 512a and 514a (FIG. 3) corresponding to anterior cut plane 511', anterior chamfer plane 513', distal cut plane 517', posterior chamfer plane 512' and posterior cut plane 514' (FIGS. 5B and 5C). The internal bone engagement surface 300a and corresponding internal planes of the generic casting 300 can correspond to standard, i.e., non-custom, sizes for the femoral implant. By selecting a relatively large number of parameters corresponding to the patient's anatomy, as captured in the three-dimensional image of the corresponding joint portion of the patient, the semi-custom implant can be made to correspond to the patient's anatomy as closely as desired while retaining the internal geometry corresponding to the resection planes in the sagittal view. More specifically, in an exemplary embodiment, at least nine parameters of the implant can be patient-specific, including three lengths and six angles, as discussed below in reference to the preoperative plan for the specific patient and the various planned resection planes.

In an exemplary embodiment of the preoperative plan, an image of the patient's anatomy, i.e. the distal femur 510' of the patient indicating the planned cut planes is illustrated in FIGS. 5B and 5C. FIG. 5B represents a distal view of the three-dimensional image of the distal femur 510', as reconstructed by MRI, CT or other scans. The planned resections indicated on the image include medial and lateral sides of a posterior chamfer plane 512', of a distal cut plane 517', and of an anterior chamfer plane 513'. The most anterior point of the intercondylar notch is indicated by a tangent line at 907. FIG. 5C represents an anterior view of the three-dimensional image of the distal femur 510', and illustrates the distal cut plane 517', anterior chamfer plane 513', and an anterior cut plane 511'. The straight edges of the various cut planes are indicated as follows in reference to FIG. 5C: posterior distal edge 950 is the posterior edge of the distal cut plane 517'; anterior distal edge 952 is the anterior edge of distal cut plane 517'; distal anterior edge 954 is the distal edge of the anterior cut plane 511'; and proximal anterior edge 956 is the proximal edge of the anterior cut plane 511'. FIG. 5B also illustrates the posterior distal edge 950, the anterior distal edge 952, and the distal anterior edge 954.

A representative, but not exhaustive list of patient-specific parameters that can be selected at the preoperative stage for incorporation into the implant design after a particular size implant has been selected is indicated in FIGS. 4A and 5A-C.

Specifically, a central plane 800 perpendicular to the epicondylar axis 801 of the distal femur 510' can be identified through the center of and orthogonal to the medial-lateral width W of the generic casting 300. The central plane 800 can be used as a reference plane for the bone cuts and the various patient-specific parameters to be used in modeling the semi-custom implant. The specified parameters can include, for example, three distances/lengths of the implant and six angles of the implant, each of which can be modified pre-operatively to be patient-specific such that they correspond to conform to the particular patient's anatomy. It will be appreciated that a lesser or greater number of parameters or different parameters can be use to customize and optimize the implant for the patient. The following exemplary parameters are illustrated in FIGS. 4A and 5A-C: medial condyle width 802, lateral condyle width 804, notch height 806, first, second and third medial angles 808, 810, 812; and first, second and third lateral angles 814, 816, 818.

In particular, and referring to FIGS. 5B and 5C, the medial condyle width 802 is defined as the distance between the central plane 800 and the farthest medial point/tangent line 902 (but not part of an osteophyte) on the posterior distal edge 950. The lateral condyle width 804 is defined as distance between the central plane 800 and the farthest lateral point/tangent 904 on the posterior distal edge 950 (but not part of an osteophyte). The notch height 806 defined as the distance along the central plane 800 from the posterior cut plane 514' at edge 906 to the most anterior point/tangent line 907 on the notch (but not part of an osteophyte). The first medial angle 808 is defined as the angle between the central plane 800 and the line 908 connecting the medial-most points on the posterior distal edge 950 and the anterior distal edge 952. The second medial angle 810 is defined as the angle between the central plane 800 and the line 910 connecting the medial-most points on the anterior distal edge 952 and the distal anterior edge 954. The third medial angle 812 is defined as the angle between the central plane 800 and the line 912 connecting the medial-most points on the distal anterior edge 954 and the proximal anterior edge 956. The first lateral angle 814 is defined as the angle between the central plane 800 and the line 914 connecting the lateral-most points on the posterior distal edge 950 and the anterior distal edge 952. The second lateral angle 816 is defined as the angle between the central plane 800 and the line 916 connecting the lateral-most points on the anterior distal edge 952 and the distal anterior edge 954. The third lateral angle 818 defined as the angle between the central plane 800 and the line 918 connecting the lateral-most points on the distal anterior edge 954 and the proximal anterior edge 956.

Referring to FIG. 1A, when the above parameters 800, 802, 804, 806, 808, 810, 812, 814, 816, 818 are identified in the pre-operative planning stage, an image of a semi-custom implant customized with these parameters can be displayed at 135 for review and comparison with the image of the patient's anatomy. The values of the parameters 800, 802, 804, 806, 808, 810, 812, 814, 816, 818 can be adjusted, as desired, and the implant with the adjusted or finalized parameters can selected at 137 and forwarded to the surgeon for review at 140 together with the preoperative plan which includes surgeon's preferences of implants, guides and other instruments, as described above in connection with FIG. 1. The preoperative planning procedure can proceed as discussed above.

As discussed above, each semi-custom implant has an internal bone engagement geometry including five planes 511a, 513a, 517a, 512a and 514a corresponding to the resection planes and at least nine patient-specific parameters, including the three lengths and six angles described above.

It will be appreciated from the above discussion that generic casting can greatly reduce inventory, machining costs and investment in mold tooling, while at the same time accommodating sizes and geometric features specific to a patient. Specifically, each implant type can be formed from a generic casting that can accommodate multiple AP sizes corresponding to medial-lateral widths, such as four sizes, for example. For implants that are available in eight sizes, generic casting can reduce inventory by a half, using two molds total for eight sizes. Further, additional reductions in inventory can be obtained by combining right and left side implants into a single generic casting, as discussed above in relation to FIG. 4. Thus, generic castings reduce side-specific castings and also allow for various custom shapes and features.

Figure 13A:
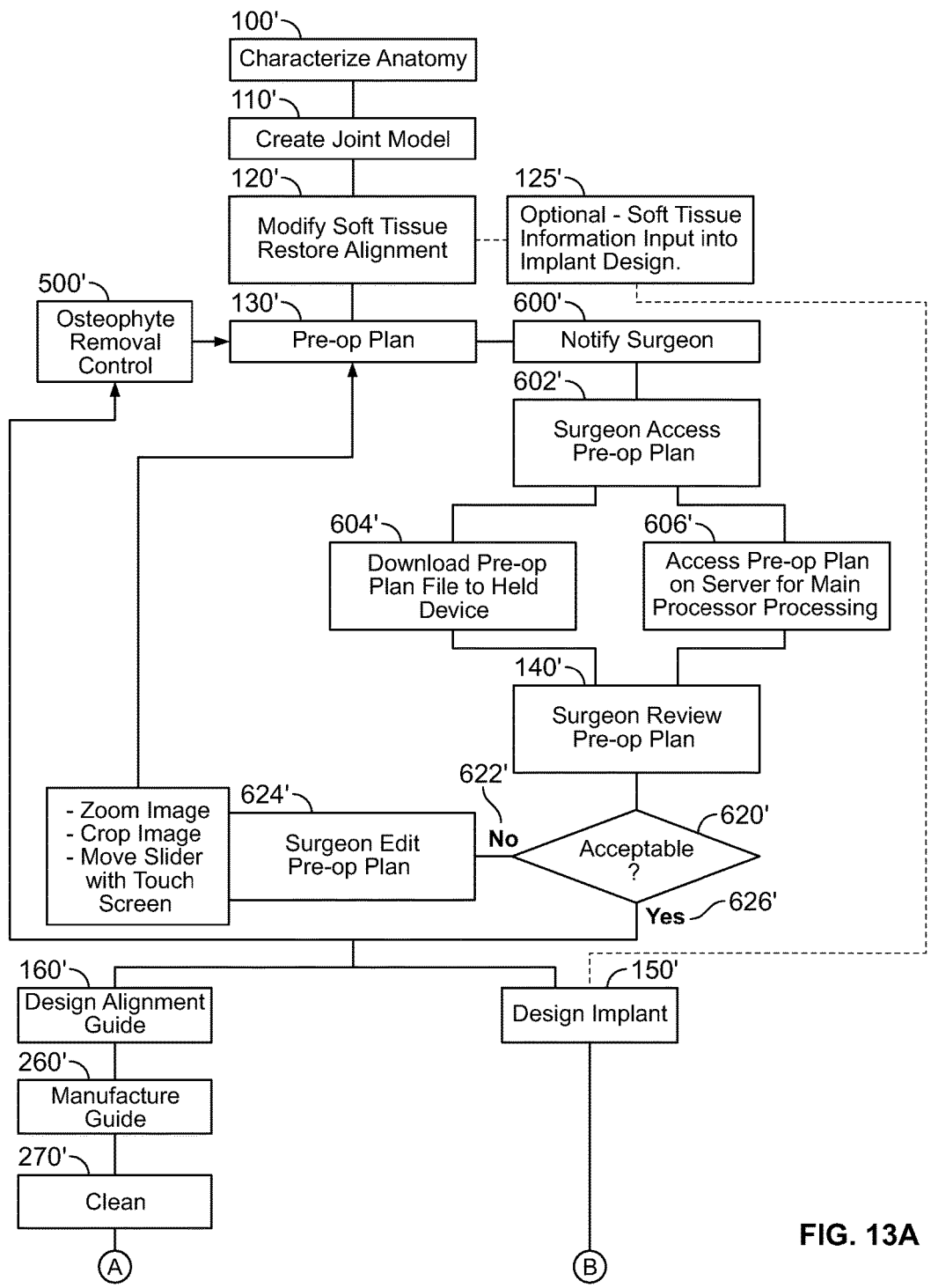
FIGS. 13A and 13B illustrate a flowchart of a method of implant and guide design.
Figure 13B:
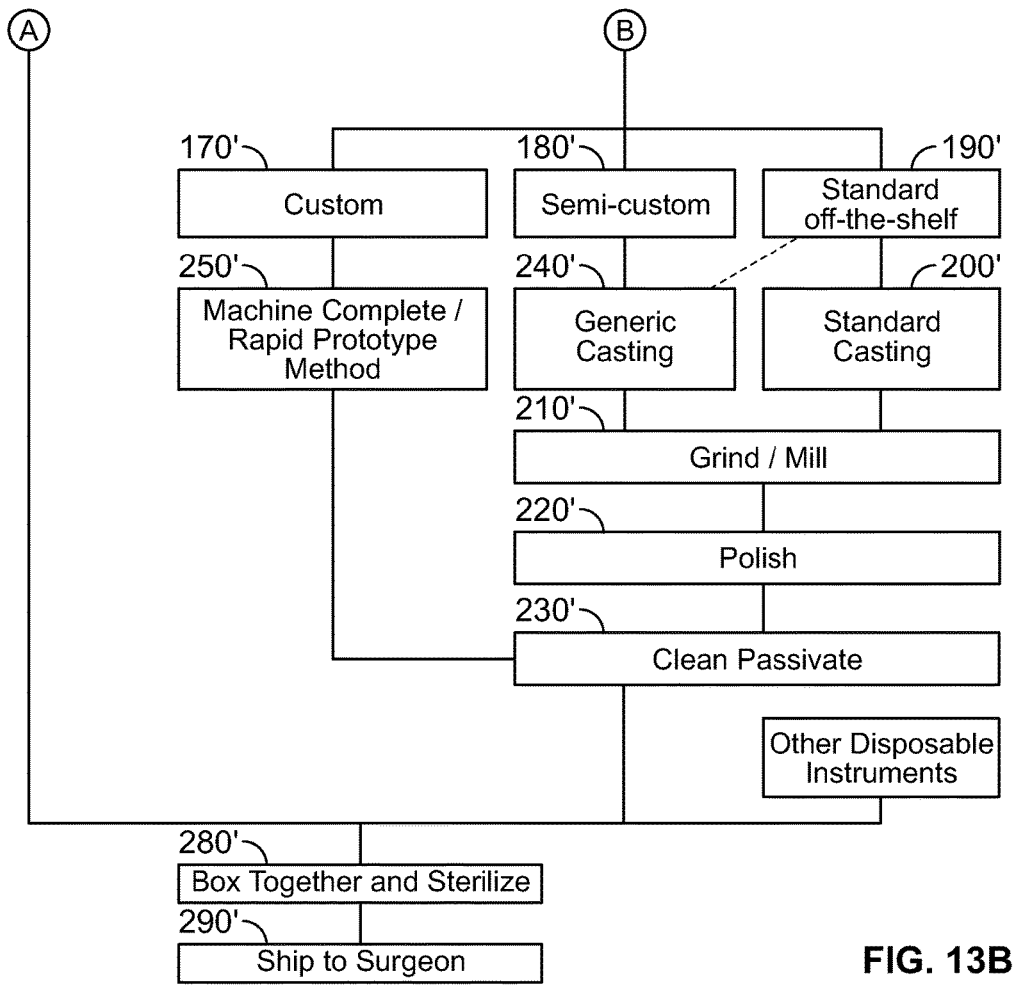

The process can then be followed as illustrated in FIGS. 13A and 13B as discussed above in relation to FIG. 1. The blocks in FIGS. 13A and 13B that are illustrated with the same reference numerals as in FIG. 1, but augmented with a prime are not discussed in further detail, but are discussed above in FIG. 1 and include substantially similar processes. In addition to the various applications discussed above, input from a surgeon or other appropriate user can be provided with a handheld device, as discussed above. As illustrated in FIGS. 13A and B, a handheld device can be used by the surgeon to review the pre-operative plan at 140'. It will be understood, however, that the process for providing a selected implant and tools can be similar to that discussed above, for example, with reference to FIG. 1

Figure 14:
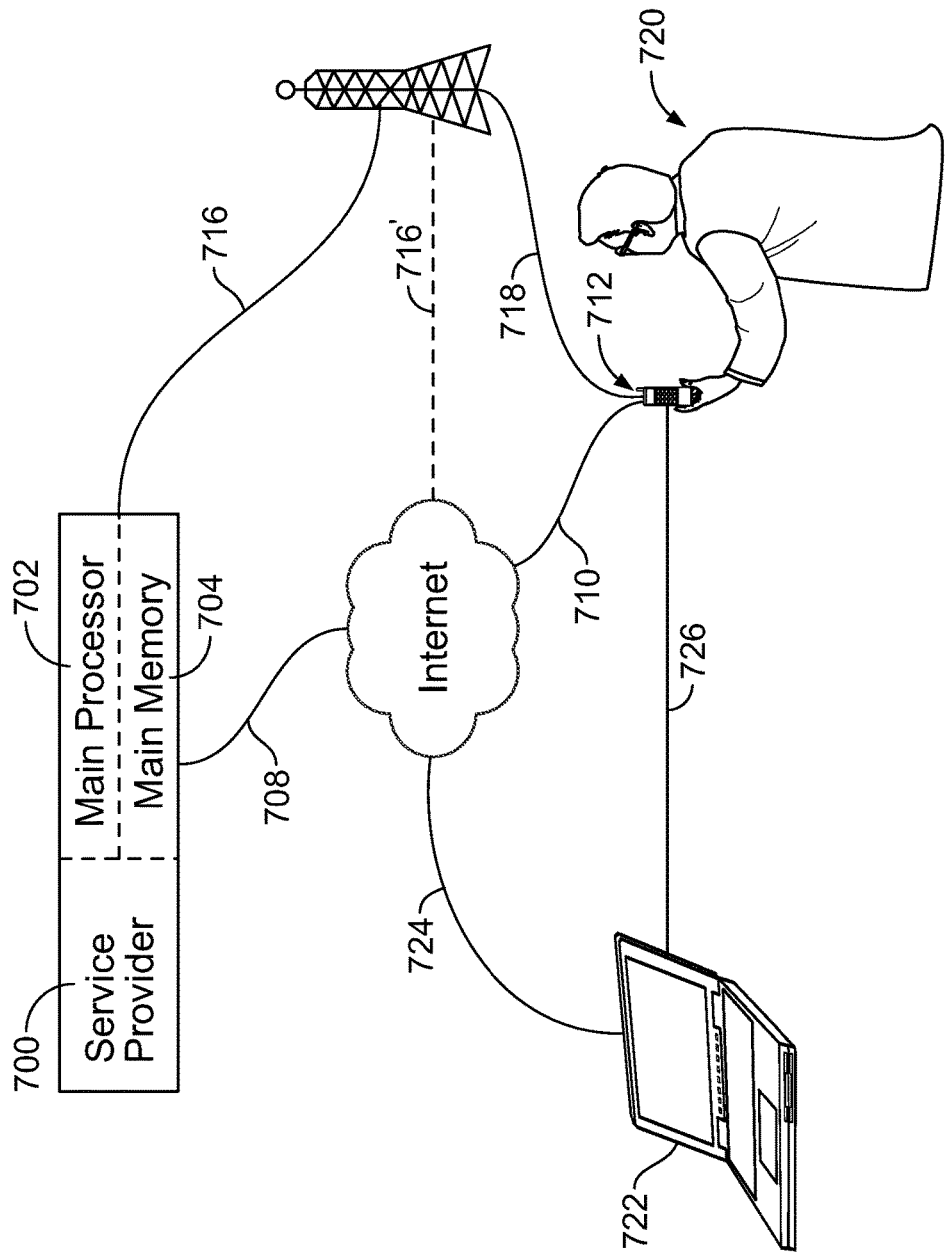
FIG. 14 is a schematic view of hardware and a user.

With reference to FIG. 14, a schematic diagram illustrating main or exemplary hardware components for the process illustrated in FIG. 13A and 13B is illustrated. The pre-operative plan or preliminary pre-operative plan from block 130 and 130' can be developed or produced by a service provider 700. The service provider 700 can own, operate, manage, or the like a main processor 702 and a main memory 704. The main processor and main memory 702, 704 can be at the service provider 700, in communication with the service provider 700, or otherwise controlled, maintained, or used by the service provider 700. Further, the main processor and main memory 702, 704 can be incorporated into a single server system. Regardless, the main processor 702 can process or execute a program, such as a program to develop the pre-operative plan, accept inputs from the surgeon, and augment or generate the final pre-operative plan. In addition, the main processor 702 can also be used to design and output the implant and alignment guide in blocks 150, 150', and 160, 160'.

As discussed above, and further herein, the pre-operative plan can be delivered or accessed by the surgeon via notification or surgeon access in block 600', 602'. The access or delivery of the pre-op plan can be via an internet or worldwide web connection 706 that uses a first communication method 708 from the service provider 700 and a second communication method 710 to a handheld device 712. It will be understood that the first and second communication method 708, 710 can be wired or wireless and can both be the same. Alternatively, or in addition to an internet connection a cell or mobile phone connection system 714, such as a tower, cell phone, antenna, can be provided. A first communication line 716 can transmit a communication through the mobile phone connection system 714. It will be understood that the service provider can communicate directly with the mobile phone connection system 714 via connection 716 or through an indirect connection 716', such as an internet connection. A second communication line 718 can be used by a surgeon 720 with the handheld device 712. Again, it will be understood, that the first and second communication system 716, 716', and 718 can be wired or wireless and can be the same or different. In addition, an intermediate system, such as a laptop or desktop computer 722 can be in communication with a system, such as the internet 706 via a first communication system 724 and the handheld device 712 can be interconnected with the computer 722 via a second communication system 726. Again, the first and second communication system 724, 726 can be the same or different and be wired or wireless.

With further reference to FIGS. 13A, 13B, and 14, the pre-operative plan from block 130' can be delivered to a surgeon or accessed by a surgeon in any appropriate manner, such as via the internet 706 or cell communication 714. The pre-operative plan can be the preliminary pre-operative plan as discussed above. The pre-operative plan can include or be saved as a data file, in the main memory 704 associated with the main processor 702 of the service provider 700, of an appropriate type including image data, patient data, resection area data, etc. The pre-operative plan can be generated and stored by the service provider 700. The service provider 700 can be any appropriate service, such as an implant and/or guide manufacturer or specification producer. A specification producer can be a service that provides specifications for an implant or guide to a manufacturer for production.

The service provider 700 can notify the surgeon 720 or user that the preliminary pre-operative plan is ready for review in block 600'. The notification that the pre-operative plan is prepared can be performed in any appropriate manner. For example, an electronic mail notification can be sent to the surgeon 720, a text message can be sent to the surgeon 720, a telephone call can be made to the surgeon 720 via landline or a wireless connection, as illustrated in FIG. 14. Regardless, the surgeon can be notified that the pre-operative plan is ready for review in block 600 through the use of the mobile device 712.

Once the surgeon 720 is notified that the pre-operative plan is ready for review, the surgeon 720 can access the pre-operative plan in block 602'. The surgeon can access the pre-operative plan in one or a plurality of ways in block 140'. For example, the surgeon 720 can download the pre-operative plan to the handheld device in block 604'. Alternatively, or in addition thereto, the surgeon 720 can access the main processor/memory 702, 704 to review the pre-operative plan in the main memory 704 in block 606' with the handheld device 712. It will be further understood that the surgeon 720 may also access the plan with the computer or terminal 722 by downloading the pre-operative plan data file to the computer 722 on which appropriate software is installed to access the pre operative plan. The surgeon 720 may also view a printout of the pre-operative plan for manipulating or commenting on the pre-operative plan, or any other appropriate manner.

If the surgeon 720 downloads the file to the handheld device 712, the file can be downloaded to the handheld device 712 using any appropriate transfer protocol or communication system, as illustrated in FIG. 14. For example, the handheld device 712 can be connected to the computer 722 through an appropriate communications cable or protocol 726, such as Bluetooth®, a wireless communication protocol or a Universal Serial Bus (USB) cable. Once the file is downloaded to the handheld device 712, a program on the handheld device 712 can execute or read the file and display images for the surgeon 720. The surgeon 720 can then review the plan in block 140'. For example, as illustrated in FIG. 7, a view of a bone to be resected can be displayed along with the slider bars 520 for allowing editing or augmentation of the pre-operative plan by the surgeon.

Figure 15:
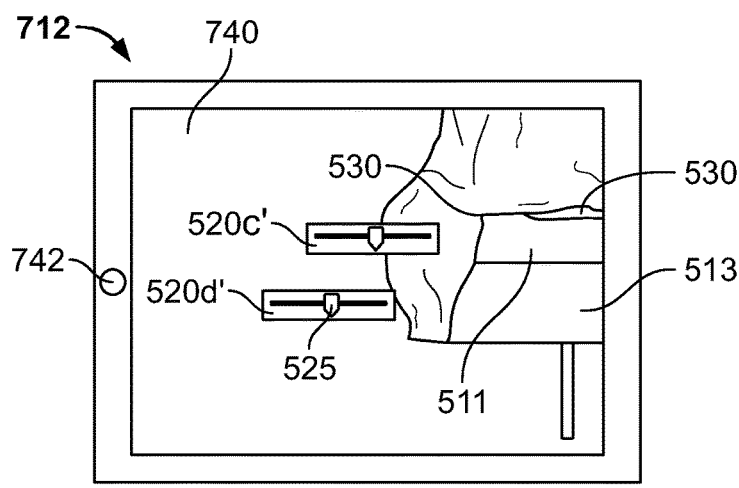
FIG. 15 is a plan view of a display of a device.

The view of the images, including the slider bars 520, can be augmented for the handheld device 712. For example, a cropped and zoomed image may only include a portion of the bone or region to be cut or resected for viewing by the surgeon. For example, as illustrated in FIG. 15, the handheld device 712 can include a view screen 740 that displays an image of the bone to be resected, but only includes a portion thereof, such as a lateral portion of a distal femur. The zoomed and cropped image can include fewer than all of the slide bars 520, such as only the slide bars 520'c and 520'd. The slide bars 520'c and 520'd can be illustrated and accessed by the surgeon to change data in the file for creation of appropriate instruments and implants for the specific patient or for augmentation of semi-custom or selection of an off-the-shelf instrument and implant.

The surgeon 720 can access or change the pre-operative plan file using the slide bars 520'c and 520'd through any appropriate access or manipulation process. For example, the screen 740 of the handheld device 712 can be a touch screen. Accordingly, the surgeon 720 can touch the screen with a finger or stylus to move the slider or marker portion 525 on the slider bars 520'c and 520'd. Alternatively, or in addition thereto, a trackball or other pointer device 742 can be provided to access and move the slider bars 520'c and 520'd. It will be understood that the handheld device 712 can have any appropriate input devices, such as an external or connected input devices, that can be mapped for appropriate command inputs into the system for augmenting the pre-operative plan file. The changes, if made by the surgeon, can then be saved to the pre-operative plan file to generate an edited pre-operative plan file.

If the surgeon 720, after review of the pre-operative plan in block 140', finds the plan to be unacceptable in block 620', the NO path 622' can be followed for the surgeon 720 to edit the plan in block 624'. The surgeon 720 can edit the plan in block 624 in any appropriate manner, such as by moving the slider bars 520'c and 520'd, or any other appropriate slider bars. Alternatively, the surgeon 720 can edit the pre-operative plan in any appropriate manner, including those discussed above. Moreover, the surgeon 720 can input changes into the pre-operative plan using any appropriate input portion, such as touching the screen 740. It will be understood, that the pre-operative plan file that is downloaded to the handheld device 712 can then be saved with the edits as the edited pre-operative plan and transmitted to the service provider 700 for appropriate edits to be re-reviewed or finalized, as discussed above. It will be understood, however, that the handheld device 712, which can include the appropriate program, can save the file in the appropriate format and transmit it back to the service provider 700.

Alternatively, or in addition to downloading the pre-operative plan file, the handheld device 712 can access the pre-operative plan which is stored in the main storage 704 associated with the service provider in block 606 and separate from the handheld device 712. If the handheld device 712 accesses the pre-operative plan on the main processor, memory 702, 704, the handheld device 712 need only display an image representing a portion of the file on the display screen 740. That is, the pre-operative plan and any edits or processing made to the pre-operative plan can be done solely or substantially by the main processor 702 that executes a program to manipulate and display the file. The main processor 702 and the main memory 704 need not be physically near or connected to the handheld device 712.

The handheld device 712 can be provided to display the image, such as an image of the bone for resection, for the surgeon 720. Therefore, the handheld device 712 may not be required to process the pre-operative plan file from the service provider 700, but only be provided to display the pre-operative plan file and receive and transmit input from the surgeon 720. Accordingly, even if the pre-operative plan is accessed from the service provider in block 606, the slide bars 520'c and 520'd can be displayed on the display 742 of the handheld device 712 for input by the surgeon 720. The inputs, however, can be directly transmitted to the main processor 702 for processing augmentation or editing of the file. This is in addition or alternative to augmenting or editing the file that has been downloaded to the handheld device 712 for re-transmission of the edited pre-operative plan to the service provider 700.

By only or substantially accessing the pre-operative plan file from the main processor/memory 702, 704 data transmission can be minimized from the main memory 704 or provider 700 to the handheld device 712 of the surgeon 720. Decreased data transmission can provide increased speed and decreased data usage costs or bottlenecks in a system. In addition, the handheld device 712 can be provided or include limited memory and processing capabilities when the pre-operative plan file is only accessed with the handheld 712 and only small amounts of information are transferred, for example, regarding slide bar location and smaller portions of an image file. Accordingly, it can be provided, that a complete or pre-operative plan is transmitted to the handheld device 712, processed completely on the handheld device 712, edited on the handheld device 712, saved and re-transmitted back to the service provider 700 or the handheld device 712 can only access the pre-operative plan file saved at the main memory 702 and transmit edits to the server.

Data transmission and processing can also be reduced by limiting or cropping the pre-operative plan data file. For example, as illustrated in FIG. 15, only a lateral and distal portion of the bone is illustrated on the display device or display screen 740 of the handheld device 712. It will be understood that an image file or image information can include the entire bone or other data saved in the image file. Accordingly, the image file can be cropped at the server or at the provider and only a portion of the image file transmitted to the handheld device 712. This can be done repeatedly for different portions of the image data to allow for smaller file packet size or file size for transmission to the handheld device 712. The cropping and compression of the data file can be done in substantially real-time by the server for a substantially seamless viewing and manipulation by the surgeon.

Even if the surgeon 720 accesses the data file on the main memory 704, the surgeon 720 can review the pre-operative plan block 140', as discussed above, and make a determination of whether the pre-operative plan is acceptable in block 620'. As discussed above, if the pre-operative plan is not acceptable, the NO path 622' can be followed to allow for surgeon edits in block 624'.

Further, regardless of the method of review of the pre-operative plan in block 140', the pre-operative plan can be determined to be acceptable in block 620' and follow the YES path 626'. When following the YES path 626', the implant can be designed and an alignment guide can be designed in blocks 150' and 160'.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic device comprising:
a femoral implant having a central plane and an internal bone engagement surface that includes an anterior planar surface, an anterior chamfer surface, a distal planar surface, a posterior chamfer surface, and a posterior planar surface, wherein the internal bone engagement surface is standardized so as to be independent of an anatomy of a specific patient's joint and is one of a series of predetermined size increments for the femoral implant, each of the series of predetermined size increments varying by a set distance from others, the femoral implant further including a medial condyle width, a lateral condyle width, a notch height located between the medial and lateral condyles and three medial angles and three lateral angles, each of the medial condyle width, the lateral condyle width, the notch height, the three medial angles and the three lateral angles are configured to be patient-specific based on an image of the specific patient's joint, wherein the medial condyle width, the lateral condyle width, the notch height, the three medial angles and the three lateral angles are designed using computer modeling to have a shape dependent upon an anatomy of the specific patient, and wherein one of the three medial angles is defined by:
an angle between the central plane and a line connecting medial-most points on an anterior edge of the distal planar surface and on a posterior edge of the distal planar surface,
an angle between the central plane and a line connecting medial-most points on a distal edge of the anterior chamfer surface and the anterior edge of the distal planar surface, or
an angle between the central plane and a line connecting medial-most points on the distal edge of the anterior chamfer surface and a proximal edge of the anterior planar surface.

2. The orthopedic device of claim 1, further comprising a surgical kit including the femoral implant and a patient-specific alignment guide.

3. The orthopedic device of claim 2, wherein the surgical kit includes reusable instruments.

4. The orthopedic device of claim 2, wherein the surgical kit includes a drill guide and a cutting block.

5. The orthopedic device of claim 2, wherein the surgical kit includes a tracking tag.

6. The orthopedic device of claim 2, wherein the patient-specific alignment guide includes a removable tracking tag.

7. An orthopedic device comprising:
a femoral implant having a central plane and an internal engagement surface that includes an anterior planar surface, an anterior chamfer surface, a distal planar surface, a posterior chamfer surface, and a posterior planar surface, wherein the internal bone engagement surface is standardized so as to be independent of an anatomy of a specific patient's joint and is one of a series of predetermined size increments for the femoral implant, each of the series of predetermined size increments varying by a set distance from others, the femoral implant further including three patient-specific lengths including a medial condyle width, a lateral condyle width, and a notch height located between the medial and lateral condyles, three patient specific medial angles and three patient-specific lateral angles, wherein each of the medial condyle width, the lateral condyle width, the notch height, the three medial angles and the three lateral angles are configured to be patient-specific based on an image of the specific patient's joint, wherein the medial condyle width, the lateral condyle width, the notch height, the three medial angles and the three lateral angles are designed using computer modeling to have a shape dependent upon an anatomy of the specific patient, and wherein one of the three lateral angles is defined by:
an angle between the central plane and a line connecting lateral-most points on the anterior edge of the distal planar surface and on the posterior edge of the distal planar surface,
an angle between the central plane and a line connecting lateral-most points on the distal edge of the anterior chamfer surface and the anterior edge of the distal planar surface, or
an angle between the central plane and a line connecting lateral-most points on the distal edge of the anterior chamfer surface and the proximal edge of the anterior planar surface.

8. The orthopedic device of claim 7, further comprising a surgical kit including the femoral implant and a patient-specific alignment guide including a removable tracking tag.

9. The orthopedic device of claim 7, further comprising a disposable instrument kit including only disposable instruments.

10. The orthopedic device of claim 9, wherein the instrument kit includes disposable patient-specific alignment guides.

11. An orthopedic device, comprising:
a semi-custom femoral implant having a central plane, and including a bone engagement surface that is standardized so as to be independent of an anatomy of a specific patient's joint and is one of a series of predetermined size increments for the femoral implant, each of the series of predetermined size increments varying by a set distance from others and an articulating surface,
wherein the non-patient-specific bone engagement surface includes an anterior planar surface, an anterior chamfer surface, a distal planar surface, a posterior chamfer surface, and a posterior planar surface;
the articulating surface includes a medial condyle and a lateral condyle separated by a notch, the notch being located along the central plane; and
the articulating surface includes plurality of patient-specific features configured to be patient-specific based on an image of the specific patient's joint and designed using computer modeling to have a shape dependent upon an anatomy of the specific patient including:
a medial condyle width;
a lateral condyle width;
a notch height defined by a distance between the posterior planar surface and the most anterior point of the notch;
a first medial angle defined by an angle between the central plane and a line connecting medial-most points on an anterior edge of the distal planar surface and on a posterior edge of the distal planar surface;
a second medial angle defined by an angle between the central plane and a line connecting medial-most points on a distal edge of the anterior chamfer surface and the anterior edge of the distal planar surface;

a third medial angle defined by an angle between the central plane and a line connecting medial-most points on the distal edge of the anterior chamfer surface and a proximal edge of the anterior planar surface;

a first lateral angle defined by an angle between the central plane and a line connecting lateral-most points on the anterior edge of the distal planar surface and on the posterior edge of the distal planar surface;

a second lateral angle defined by an angle between the central plane and a line connecting lateral-most points on the distal edge of the anterior chamfer surface and the anterior edge of the distal planar surface;

a third lateral angle defined by an angle between the central plane and a line connecting lateral-most points on the distal edge of the anterior chamfer surface and the proximal edge of the anterior planar surface.

12. The orthopedic device of claim 11, further comprising a surgical kit including the femoral implant and a patient-specific alignment guide.

13. The orthopedic device of claim 12, wherein the surgical kit includes reusable instruments.

14. The orthopedic device of claim 12, wherein the surgical kit includes a drill guide and a cutting block.

15. The orthopedic device of claim 12, wherein the surgical kit includes a tracking tag.

16. The orthopedic device of claim 12, wherein the patient-specific alignment guide includes a removable tracking tag.

* * * * *